United States Patent
Tearney et al.

(10) Patent No.: US 8,289,522 B2
(45) Date of Patent: Oct. 16, 2012

(54) ARRANGEMENTS AND METHODS FOR PROVIDING MULTIMODALITY MICROSCOPIC IMAGING OF ONE OR MORE BIOLOGICAL STRUCTURES

(75) Inventors: Guillermo J. Tearney, Cambridge, MA (US); Dvir Yelin, Brookline, MA (US); Benjamin J. Vakoc, Cambridge, MA (US); Wang-Yuhl Oh, Cambridge, MA (US); Brett E. Bouma, Quincy, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 12/943,762

(22) Filed: Nov. 10, 2010

(65) Prior Publication Data
US 2011/0058178 A1    Mar. 10, 2011

Related U.S. Application Data

(62) Division of application No. 11/537,343, filed on Sep. 29, 2006, now Pat. No. 7,872,759.

(60) Provisional application No. 60/721,802, filed on Sep. 29, 2005.

(51) Int. Cl.
*G01B 9/02* (2006.01)
(52) U.S. Cl. ...................................... 356/479
(58) Field of Classification Search .......... 356/477, 356/479, 497; 250/227.19, 227.27; 385/12
See application file for complete search history.

(56) References Cited

U.S. PATENT DOCUMENTS

| | | | |
|---|---|---|---|
| 2,339,754 | A | 1/1944 | Brace |
| 3,090,753 | A | 5/1963 | Matuszak et al. |
| 3,601,480 | A | 8/1971 | Randall |
| 3,856,000 | A | 12/1974 | Chikama |
| 3,872,407 | A | 3/1975 | Hughes |

(Continued)

FOREIGN PATENT DOCUMENTS

CN    1550203    12/2004

(Continued)

OTHER PUBLICATIONS

Fujimoto et al., "High Resolution in Vivo Intra-Arterial Imaging with Optical Coherence Tomography," *Official Journal of the British Cardiac Society*, vol. 82, pp. 128-133 Heart, 1999.

(Continued)

*Primary Examiner* — Michael A Lyons
(74) *Attorney, Agent, or Firm* — Dorsey & Whitney LLP

(57) ABSTRACT

Method and apparatus according to an exemplary embodiment of the present invention can be provided. For example, first data associated with a first signal received from at least one region of at least one sample can be provided based on a first modality, and second data associated with a second signal received from the at least one sample can be provided based on a second modality which is different from the first modality. Third data associated with a reference can be received. Further data can be generated based on the first, second and third data. In addition, third data associated with a second signal received from the at least one sample can be obtained. Each of the third data can be based on a further modality which is different from the first modality and the second modality, and the further data can be further determined based on the third data. Further, the first modality can be a spectral-encoded modality, and the second modality can be a non-spectral-encoding modality.

22 Claims, 22 Drawing Sheets

U.S. PATENT DOCUMENTS

| | | | |
|---|---|---|---|
| 3,941,121 A | 3/1976 | Olinger | |
| 3,973,219 A | 8/1976 | Tang et al. | |
| 3,983,507 A | 9/1976 | Tang et al. | |
| 4,030,827 A | 6/1977 | Delhaye et al. | |
| 4,030,831 A | 6/1977 | Gowrinathan | |
| 4,140,364 A | 2/1979 | Yamashita et al. | |
| 4,141,362 A | 2/1979 | Wurster | |
| 4,224,929 A | 9/1980 | Furihata | |
| 4,295,738 A | 10/1981 | Meltz et al. | |
| 4,300,816 A | 11/1981 | Snitzer et al. | |
| 4,303,300 A | 12/1981 | Pressiat et al. | |
| 4,428,643 A | 1/1984 | Kay | |
| 4,479,499 A | 10/1984 | Alfano | |
| 4,533,247 A | 8/1985 | Epworth | |
| 4,585,349 A | 4/1986 | Gross et al. | |
| 4,601,036 A | 7/1986 | Faxvog et al. | |
| 4,607,622 A | 8/1986 | Fritch et al. | |
| 4,631,498 A | 12/1986 | Cutler | |
| 4,639,999 A | 2/1987 | Daniele | |
| 4,650,327 A | 3/1987 | Ogi | |
| 4,734,578 A | 3/1988 | Horikawa | |
| 4,744,656 A | 5/1988 | Moran et al. | |
| 4,751,706 A | 6/1988 | Rohde et al. | |
| 4,763,977 A | 8/1988 | Kawasaki et al. | |
| 4,770,492 A | 9/1988 | Levin et al. | |
| 4,827,907 A | 5/1989 | Tashiro et al. | |
| 4,834,111 A | 5/1989 | Khanna et al. | |
| 4,868,834 A | 9/1989 | Fox et al. | |
| 4,890,901 A | 1/1990 | Cross, Jr. | |
| 4,892,406 A | 1/1990 | Waters | |
| 4,905,169 A | 2/1990 | Buican et al. | |
| 4,909,631 A | 3/1990 | Tan et al. | |
| 4,925,302 A | 5/1990 | Cutler | |
| 4,928,005 A | 5/1990 | Lefèvre et al. | |
| 4,940,328 A | 7/1990 | Hartman | |
| 4,965,441 A | 10/1990 | Picard | |
| 4,965,599 A | 10/1990 | Roddy et al. | |
| 4,966,589 A | 10/1990 | Kaufman | |
| 4,984,888 A | 1/1991 | Tobias et al. | |
| 4,993,834 A | 2/1991 | Carlhoff et al. | |
| 4,998,972 A | 3/1991 | Chin et al. | |
| 5,039,193 A | 8/1991 | Snow et al. | |
| 5,040,889 A | 8/1991 | Keane | |
| 5,045,936 A | 9/1991 | Lobb et al. | |
| 5,046,501 A | 9/1991 | Crilly | |
| 5,065,331 A | 11/1991 | Vachon et al. | |
| 5,085,496 A | 2/1992 | Yoshida et al. | |
| 5,120,953 A | 6/1992 | Harris | |
| 5,121,983 A | 6/1992 | Lee | |
| 5,127,730 A | 7/1992 | Brelje et al. | |
| 5,197,470 A | 3/1993 | Helfer et al. | |
| 5,202,745 A | 4/1993 | Sorin et al. | |
| 5,202,931 A | 4/1993 | Bacus et al. | |
| 5,208,651 A | 5/1993 | Buican | |
| 5,212,667 A | 5/1993 | Tomlinson et al. | |
| 5,214,538 A | 5/1993 | Lobb | |
| 5,217,456 A | 6/1993 | Narciso, Jr. | |
| 5,228,001 A | 7/1993 | Birge et al. | |
| 5,241,364 A | 8/1993 | Kimura et al. | |
| 5,248,876 A | 9/1993 | Kerstens et al. | |
| 5,250,186 A | 10/1993 | Dollinger et al. | |
| 5,251,009 A | 10/1993 | Bruno | |
| 5,262,644 A | 11/1993 | Maguire | |
| 5,275,594 A | 1/1994 | Baker | |
| 5,281,811 A | 1/1994 | Lewis | |
| 5,283,795 A | 2/1994 | Fink | |
| 5,291,885 A | 3/1994 | Taniji et al. | |
| 5,293,872 A | 3/1994 | Alfano et al. | |
| 5,293,873 A | 3/1994 | Fang | |
| 5,302,025 A | 4/1994 | Kleinerman | |
| 5,304,173 A | 4/1994 | Kittrell et al. | |
| 5,304,810 A | 4/1994 | Amos | |
| 5,305,759 A | 4/1994 | Kaneko et al. | |
| 5,317,389 A | 5/1994 | Hochberg et al. | |
| 5,318,024 A | 6/1994 | Kittrell et al. | |
| 5,321,501 A | 6/1994 | Swanson et al. | |
| 5,333,144 A | 7/1994 | Liedenbaum et al. | |
| 5,348,003 A | 9/1994 | Caro | |
| 5,353,790 A | 10/1994 | Jacques et al. | |
| 5,383,467 A | 1/1995 | Auer et al. | |
| 5,394,235 A | 2/1995 | Takeuchi et al. | |
| 5,404,415 A | 4/1995 | Mori et al. | |
| 5,411,016 A | 5/1995 | Kume et al. | |
| 5,419,323 A | 5/1995 | Kittrell et al. | |
| 5,424,827 A | 6/1995 | Horwitz et al. | |
| 5,439,000 A | 8/1995 | Gunderson et al. | |
| 5,441,053 A | 8/1995 | Lodder et al. | |
| 5,450,203 A | 9/1995 | Penkethman | |
| 5,454,807 A | 10/1995 | Lennox et al. | |
| 5,459,325 A | 10/1995 | Hueton et al. | |
| 5,459,570 A | 10/1995 | Swanson et al. | |
| 5,465,147 A | 11/1995 | Swanson | |
| 5,486,701 A | 1/1996 | Norton et al. | |
| 5,491,524 A | 2/1996 | Hellmuth et al. | |
| 5,491,552 A | 2/1996 | Knuttel | |
| 5,522,004 A | 5/1996 | Djupsjobacka et al. | |
| 5,526,338 A | 6/1996 | Hasman et al. | |
| 5,555,087 A | 9/1996 | Miyagawa et al. | |
| 5,562,100 A | 10/1996 | Kittrell et al. | |
| 5,565,983 A | 10/1996 | Barnard et al. | |
| 5,565,986 A | 10/1996 | Knuttel | |
| 5,566,267 A | 10/1996 | Neuberger | |
| 5,583,342 A | 12/1996 | Ichie | |
| 5,590,660 A | 1/1997 | MacAulay et al. | |
| 5,600,486 A | 2/1997 | Gal et al. | |
| 5,601,087 A | 2/1997 | Gunderson et al. | |
| 5,621,830 A | 4/1997 | Lucey et al. | |
| 5,623,336 A | 4/1997 | Raab | |
| 5,635,830 A | 6/1997 | Itoh | |
| 5,649,924 A | 7/1997 | Everett et al. | |
| 5,697,373 A | 12/1997 | Richards-Kortum et al. | |
| 5,698,397 A | 12/1997 | Zarling et al. | |
| 5,710,630 A | 1/1998 | Essenpreis et al. | |
| 5,716,324 A | 2/1998 | Toida | |
| 5,719,399 A | 2/1998 | Alfano et al. | |
| 5,730,731 A | 3/1998 | Mollenauer et al. | |
| 5,735,276 A | 4/1998 | Lemelson | |
| 5,740,808 A | 4/1998 | Panescu et al. | |
| 5,748,318 A | 5/1998 | Maris et al. | |
| 5,748,598 A | 5/1998 | Swanson et al. | |
| 5,752,518 A | 5/1998 | McGee et al. | |
| 5,784,352 A | 7/1998 | Swanson et al. | |
| 5,785,651 A | 7/1998 | Kuhn et al. | |
| 5,793,480 A * | 8/1998 | Lacey et al. | 356/73 |
| 5,795,295 A | 8/1998 | Hellmuth et al. | |
| 5,801,826 A | 9/1998 | Williams | |
| 5,801,831 A | 9/1998 | Sargoytchev et al. | |
| 5,803,082 A | 9/1998 | Stapleton et al. | |
| 5,807,261 A | 9/1998 | Benaron et al. | |
| 5,810,719 A | 9/1998 | Toida | |
| 5,817,144 A | 10/1998 | Gregory | |
| 5,836,877 A | 11/1998 | Zavislan et al. | |
| 5,840,023 A | 11/1998 | Oraevsky et al. | |
| 5,840,031 A | 11/1998 | Crowley | |
| 5,840,075 A | 11/1998 | Mueller et al. | |
| 5,842,995 A | 12/1998 | Mahadevan-Jansen et al. | |
| 5,843,000 A | 12/1998 | Nishioka et al. | |
| 5,843,052 A | 12/1998 | Benja-Athon | |
| 5,847,827 A | 12/1998 | Fercher | |
| 5,862,273 A | 1/1999 | Pelletier | |
| 5,865,754 A | 2/1999 | Sevick-Muraca et al. | |
| 5,867,268 A | 2/1999 | Gelikonov et al. | |
| 5,871,449 A | 2/1999 | Brown | |
| 5,872,879 A | 2/1999 | Hamm | |
| 5,877,856 A | 3/1999 | Fercher | |
| 5,887,009 A | 3/1999 | Mandella et al. | |
| 5,892,583 A | 4/1999 | Li | |
| 5,910,839 A | 6/1999 | Erskine et al. | |
| 5,912,764 A | 6/1999 | Togino | |
| 5,920,373 A | 7/1999 | Bille | |
| 5,920,390 A | 7/1999 | Farahi et al. | |
| 5,921,926 A | 7/1999 | Rolland et al. | |
| 5,926,592 A | 7/1999 | Harris et al. | |
| 5,949,929 A | 9/1999 | Hamm | |
| 5,951,482 A | 9/1999 | Winston et al. | |
| 5,955,737 A | 9/1999 | Hallidy et al. | |
| 5,956,355 A | 9/1999 | Swanson et al. | |

| | | |
|---|---|---|
| 5,968,064 A | 10/1999 | Selmon et al. |
| 5,975,697 A | 11/1999 | Podoleanu et al. |
| 5,983,125 A | 11/1999 | Alfano et al. |
| 5,987,346 A | 11/1999 | Benaron et al. |
| 5,991,697 A | 11/1999 | Nelson et al. |
| 5,994,690 A | 11/1999 | Kulkarni et al. |
| 5,995,223 A | 11/1999 | Power |
| 6,002,480 A | 12/1999 | Izatt et al. |
| 6,004,314 A | 12/1999 | Wei et al. |
| 6,006,128 A | 12/1999 | Izatt et al. |
| 6,007,996 A | 12/1999 | McNamara et al. |
| 6,010,449 A | 1/2000 | Selmon et al. |
| 6,014,214 A | 1/2000 | Li |
| 6,016,197 A | 1/2000 | Krivoshlykov |
| 6,020,963 A | 2/2000 | DiMarzio et al. |
| 6,025,956 A | 2/2000 | Nagano et al. |
| 6,033,721 A | 3/2000 | Nassuphis |
| 6,037,579 A | 3/2000 | Chan et al. |
| 6,044,288 A | 3/2000 | Wake et al. |
| 6,045,511 A | 4/2000 | Ott et al. |
| 6,048,742 A | 4/2000 | Weyburne et al. |
| 6,053,613 A | 4/2000 | Wei et al. |
| 6,069,698 A | 5/2000 | Ozawa et al. |
| 6,078,047 A | 6/2000 | Mittleman et al. |
| 6,091,496 A | 7/2000 | Hill |
| 6,091,984 A | 7/2000 | Perelman et al. |
| 6,094,274 A | 7/2000 | Yokoi |
| 6,107,048 A | 8/2000 | Goldenring et al. |
| 6,111,645 A | 8/2000 | Tearney et al. |
| 6,117,128 A | 9/2000 | Gregory |
| 6,120,516 A | 9/2000 | Selmon et al. |
| 6,134,003 A | 10/2000 | Tearney et al. |
| 6,134,010 A | 10/2000 | Zavislan |
| 6,134,033 A | 10/2000 | Bergano et al. |
| 6,141,577 A | 10/2000 | Rolland et al. |
| 6,151,522 A | 11/2000 | Alfano et al. |
| 6,159,445 A | 12/2000 | Klaveness et al. |
| 6,160,826 A | 12/2000 | Swanson et al. |
| 6,161,031 A | 12/2000 | Hochmann et al. |
| 6,166,373 A | 12/2000 | Mao |
| 6,174,291 B1 | 1/2001 | McMahon et al. |
| 6,175,669 B1 | 1/2001 | Colston et al. |
| 6,185,271 B1 | 2/2001 | Kinsinger |
| 6,191,862 B1 * | 2/2001 | Swanson et al. .............. 356/479 |
| 6,193,676 B1 | 2/2001 | Winston et al. |
| 6,198,956 B1 | 3/2001 | Dunne |
| 6,201,989 B1 | 3/2001 | Whitehead et al. |
| 6,208,415 B1 | 3/2001 | De Boer et al. |
| 6,208,887 B1 | 3/2001 | Clarke |
| 6,245,026 B1 | 6/2001 | Campbell et al. |
| 6,249,349 B1 | 6/2001 | Lauer |
| 6,249,381 B1 | 6/2001 | Suganuma |
| 6,249,630 B1 | 6/2001 | Stock et al. |
| 6,263,234 B1 | 7/2001 | Engelhardt et al. |
| 6,264,610 B1 | 7/2001 | Zhu |
| 6,272,268 B1 | 8/2001 | Miller et al. |
| 6,272,376 B1 | 8/2001 | Marcu et al. |
| 6,274,871 B1 | 8/2001 | Dukor et al. |
| 6,282,011 B1 | 8/2001 | Tearney et al. |
| 6,297,018 B1 | 10/2001 | French et al. |
| 6,301,048 B1 | 10/2001 | Cao et al. |
| 6,308,092 B1 | 10/2001 | Hoyns |
| 6,324,419 B1 | 11/2001 | Guzelsu et al. |
| 6,341,036 B1 | 1/2002 | Tearney et al. |
| 6,353,693 B1 | 3/2002 | Kano et al. |
| 6,359,692 B1 | 3/2002 | Groot |
| 6,374,128 B1 | 4/2002 | Toida et al. |
| 6,377,349 B1 | 4/2002 | Fercher |
| 6,384,915 B1 | 5/2002 | Everett et al. |
| 6,393,312 B1 | 5/2002 | Hoyns |
| 6,394,964 B1 | 5/2002 | Sievert, Jr. et al. |
| 6,396,941 B1 | 5/2002 | Bacus et al. |
| 6,421,164 B2 | 7/2002 | Tearney et al. |
| 6,437,867 B2 | 8/2002 | Zeylikovich et al. |
| 6,441,892 B2 | 8/2002 | Xiao et al. |
| 6,441,959 B1 | 8/2002 | Yang et al. |
| 6,445,485 B1 | 9/2002 | Frigo et al. |
| 6,445,939 B1 | 9/2002 | Swanson et al. |
| 6,445,944 B1 | 9/2002 | Ostrovsky |
| 6,459,487 B1 | 10/2002 | Chen et al. |
| 6,463,313 B1 | 10/2002 | Winston et al. |
| 6,469,846 B2 | 10/2002 | Ebizuka et al. |
| 6,475,159 B1 | 11/2002 | Casscells et al. |
| 6,475,210 B1 | 11/2002 | Phelps et al. |
| 6,477,403 B1 | 11/2002 | Eguchi et al. |
| 6,485,413 B1 | 11/2002 | Boppart et al. |
| 6,485,482 B1 | 11/2002 | Belef |
| 6,501,551 B1 | 12/2002 | Tearney et al. |
| 6,501,878 B2 | 12/2002 | Hughes et al. |
| 6,516,014 B1 | 2/2003 | Sellin et al. |
| 6,517,532 B1 | 2/2003 | Altshuler et al. |
| 6,538,817 B1 | 3/2003 | Farmer et al. |
| 6,540,391 B2 | 4/2003 | Lanzetta et al. |
| 6,549,801 B1 | 4/2003 | Chen et al. |
| 6,552,796 B2 | 4/2003 | Magnin et al. |
| 6,556,305 B1 | 4/2003 | Aziz et al. |
| 6,556,853 B1 | 4/2003 | Cabib et al. |
| 6,558,324 B1 | 5/2003 | Von Behren et al. |
| 6,560,259 B1 | 5/2003 | Hwang et al. |
| 6,564,087 B1 | 5/2003 | Pitris et al. |
| 6,564,089 B2 | 5/2003 | Izatt et al. |
| 6,567,585 B2 | 5/2003 | Harris |
| 6,593,101 B2 | 7/2003 | Richards-Kortum et al. |
| 6,611,833 B1 | 8/2003 | Johnson et al. |
| 6,615,071 B1 | 9/2003 | Casscells, III et al. |
| 6,622,732 B2 | 9/2003 | Constantz |
| 6,654,127 B2 | 11/2003 | Everett et al. |
| 6,657,730 B2 | 12/2003 | Pfau et al. |
| 6,658,278 B2 | 12/2003 | Gruhl |
| 6,680,780 B1 | 1/2004 | Fee |
| 6,685,885 B2 | 2/2004 | Varma et al. |
| 6,687,007 B1 | 2/2004 | Meigs |
| 6,687,010 B1 | 2/2004 | Horii et al. |
| 6,687,036 B2 | 2/2004 | Riza |
| 6,692,430 B2 | 2/2004 | Adler |
| 6,701,181 B2 | 3/2004 | Tang et al. |
| 6,721,094 B1 | 4/2004 | Sinclair et al. |
| 6,725,073 B1 | 4/2004 | Motamedi et al. |
| 6,738,144 B1 | 5/2004 | Dogariu et al. |
| 6,741,355 B2 | 5/2004 | Drabarek |
| 6,757,467 B1 | 6/2004 | Rogers |
| 6,790,175 B1 | 9/2004 | Furusawa et al. |
| 6,806,963 B1 | 10/2004 | Wälti et al. |
| 6,816,743 B2 | 11/2004 | Moreno et al. |
| 6,831,781 B2 | 12/2004 | Tearney et al. |
| 6,839,496 B1 | 1/2005 | Mills et al. |
| 6,856,384 B1 * | 2/2005 | Rovira ........................... 356/73 |
| 6,882,432 B2 | 4/2005 | Deck |
| 6,900,899 B2 | 5/2005 | Nevis |
| 6,903,820 B2 | 6/2005 | Wang |
| 6,909,105 B1 | 6/2005 | Heintzmann et al. |
| 6,949,072 B2 | 9/2005 | Furnish et al. |
| 6,961,123 B1 | 11/2005 | Wang et al. |
| 6,980,299 B1 | 12/2005 | de Boer |
| 6,996,549 B2 | 2/2006 | Zhang et al. |
| 7,006,231 B2 | 2/2006 | Ostrovsky et al. |
| 7,006,232 B2 | 2/2006 | Rollins et al. |
| 7,019,838 B2 * | 3/2006 | Izatt et al. ..................... 356/479 |
| 7,027,633 B2 | 4/2006 | Foran et al. |
| 7,061,622 B2 | 6/2006 | Rollins et al. |
| 7,072,047 B2 | 7/2006 | Westphal et al. |
| 7,075,658 B2 | 7/2006 | Izatt et al. |
| 7,099,358 B1 | 8/2006 | Chong et al. |
| 7,113,288 B2 | 9/2006 | Fercher |
| 7,113,625 B2 | 9/2006 | Watson et al. |
| 7,130,320 B2 | 10/2006 | Tobiason et al. |
| 7,139,598 B2 | 11/2006 | Hull et al. |
| 7,142,835 B2 | 11/2006 | Paulus |
| 7,148,970 B2 | 12/2006 | De Boer |
| 7,177,027 B2 | 2/2007 | Hirasawa et al. |
| 7,190,464 B2 | 3/2007 | Alphonse |
| 7,230,708 B2 | 6/2007 | Lapotko et al. |
| 7,231,243 B2 | 6/2007 | Tearney et al. |
| 7,236,637 B2 | 6/2007 | Sirohey et al. |
| 7,242,480 B2 | 7/2007 | Alphonse |
| 7,267,494 B2 | 9/2007 | Deng et al. |
| 7,272,252 B2 | 9/2007 | De La Torre-Bueno et al. |
| 7,304,798 B2 | 12/2007 | Izumi et al. |

| Patent No. | Date | Inventor |
|---|---|---|
| 7,310,150 B2 | 12/2007 | Guillermo et al. |
| 7,330,270 B2 | 2/2008 | O'Hara et al. |
| 7,336,366 B2 | 2/2008 | Choma et al. |
| 7,342,659 B2 | 3/2008 | Horn et al. |
| 7,355,716 B2 | 4/2008 | De Boer et al. |
| 7,355,721 B2 | 4/2008 | Quadling et al. |
| 7,359,062 B2 | 4/2008 | Chen et al. |
| 7,366,376 B2 | 4/2008 | Shishkov et al. |
| 7,382,809 B2 | 6/2008 | Chong et al. |
| 7,391,520 B2 | 6/2008 | Zhou et al. |
| 7,458,683 B2 | 12/2008 | Chernyak et al. |
| 7,530,948 B2 | 5/2009 | Seibel et al. |
| 7,539,530 B2 | 5/2009 | Caplan et al. |
| 7,609,391 B2 | 10/2009 | Betzig |
| 7,630,083 B2 | 12/2009 | de Boer et al. |
| 7,643,152 B2 | 1/2010 | de Boer et al. |
| 7,643,153 B2 | 1/2010 | de Boer et al. |
| 7,646,905 B2 | 1/2010 | Guittet et al. |
| 7,649,160 B2 | 1/2010 | Colomb et al. |
| 7,664,300 B2 | 2/2010 | Lange et al. |
| 7,733,497 B2 | 6/2010 | Yun et al. |
| 7,782,464 B2 | 8/2010 | Mujat et al. |
| 7,805,034 B2 | 9/2010 | Kato et al. |
| 7,872,759 B2 * | 1/2011 | Tearney et al. .............. 356/479 |
| 2001/0020126 A1 | 9/2001 | Swanson et al. |
| 2001/0036002 A1 | 11/2001 | Tearney et al. |
| 2001/0047137 A1 | 11/2001 | Moreno et al. |
| 2002/0016533 A1 | 2/2002 | Marchitto et al. |
| 2002/0024015 A1 | 2/2002 | Hoffmann et al. |
| 2002/0048025 A1 * | 4/2002 | Takaoka .................. 356/497 |
| 2002/0048026 A1 | 4/2002 | Isshiki et al. |
| 2002/0052547 A1 | 5/2002 | Toida |
| 2002/0057431 A1 | 5/2002 | Fateley et al. |
| 2002/0064341 A1 | 5/2002 | Fauver et al. |
| 2002/0076152 A1 | 6/2002 | Hughes et al. |
| 2002/0085209 A1 | 7/2002 | Mittleman et al. |
| 2002/0086347 A1 | 7/2002 | Johnson et al. |
| 2002/0091322 A1 | 7/2002 | Chaiken et al. |
| 2002/0093662 A1 | 7/2002 | Chen et al. |
| 2002/0109851 A1 | 8/2002 | Deck |
| 2002/0113965 A1 | 8/2002 | Roche et al. |
| 2002/0122182 A1 | 9/2002 | Everett et al. |
| 2002/0122246 A1 | 9/2002 | Tearney et al. |
| 2002/0140942 A1 | 10/2002 | Fee et al. |
| 2002/0158211 A1 | 10/2002 | Gillispie |
| 2002/0161357 A1 | 10/2002 | Anderson et al. |
| 2002/0163622 A1 | 11/2002 | Magnin et al. |
| 2002/0168158 A1 | 11/2002 | Furusawa et al. |
| 2002/0172485 A1 | 11/2002 | Keaton et al. |
| 2002/0183623 A1 | 12/2002 | Tang et al. |
| 2002/0188204 A1 | 12/2002 | McNamara et al. |
| 2002/0196446 A1 | 12/2002 | Roth et al. |
| 2002/0198457 A1 | 12/2002 | Tearney et al. |
| 2003/0001071 A1 | 1/2003 | Mandella et al. |
| 2003/0013973 A1 | 1/2003 | Georgakoudi et al. |
| 2003/0023153 A1 | 1/2003 | Izatt et al. |
| 2003/0026735 A1 | 2/2003 | Nolte et al. |
| 2003/0028114 A1 | 2/2003 | Casscells, III et al. |
| 2003/0030816 A1 | 2/2003 | Eom et al. |
| 2003/0043381 A1 | 3/2003 | Fercher |
| 2003/0053673 A1 | 3/2003 | Dewaele et al. |
| 2003/0067607 A1 | 4/2003 | Wolleschensky et al. |
| 2003/0082105 A1 | 5/2003 | Fischman et al. |
| 2003/0097048 A1 | 5/2003 | Ryan et al. |
| 2003/0108911 A1 | 6/2003 | Klimant et al. |
| 2003/0120137 A1 | 6/2003 | Pawluczyk et al. |
| 2003/0135101 A1 | 7/2003 | Webler |
| 2003/0137669 A1 | 7/2003 | Rollins et al. |
| 2003/0164952 A1 | 9/2003 | Deichmann et al. |
| 2003/0165263 A1 | 9/2003 | Hamer et al. |
| 2003/0171691 A1 | 9/2003 | Casscells, III et al. |
| 2003/0174339 A1 | 9/2003 | Feldchtein et al. |
| 2003/0199769 A1 | 10/2003 | Podoleanu et al. |
| 2003/0216719 A1 | 11/2003 | Debenedictis et al. |
| 2003/0218756 A1 | 11/2003 | Chen et al. |
| 2003/0220749 A1 | 11/2003 | Chen et al. |
| 2003/0236443 A1 | 12/2003 | Cespedes et al. |
| 2004/0002650 A1 | 1/2004 | Mandrusov et al. |
| 2004/0039298 A1 | 2/2004 | Abreu |
| 2004/0054268 A1 | 3/2004 | Esenaliev et al. |
| 2004/0072200 A1 | 4/2004 | Rigler et al. |
| 2004/0075841 A1 | 4/2004 | Van Neste et al. |
| 2004/0076940 A1 | 4/2004 | Alexander et al. |
| 2004/0077949 A1 | 4/2004 | Blofgett et al. |
| 2004/0085540 A1 | 5/2004 | Lapotko et al. |
| 2004/0086245 A1 | 5/2004 | Farroni et al. |
| 2004/0095464 A1 | 5/2004 | Miyagi et al. |
| 2004/0100631 A1 | 5/2004 | Bashkansky et al. |
| 2004/0100681 A1 | 5/2004 | Bjarklev et al. |
| 2004/0110206 A1 | 6/2004 | Wong et al. |
| 2004/0126048 A1 | 7/2004 | Dave et al. |
| 2004/0126120 A1 | 7/2004 | Cohen et al. |
| 2004/0133191 A1 | 7/2004 | Momiuchi et al. |
| 2004/0150829 A1 | 8/2004 | Koch et al. |
| 2004/0150830 A1 | 8/2004 | Chan |
| 2004/0152989 A1 | 8/2004 | Puttappa et al. |
| 2004/0165184 A1 | 8/2004 | Mizuno |
| 2004/0166593 A1 | 8/2004 | Nolte et al. |
| 2004/0189999 A1 | 9/2004 | De Groot et al. |
| 2004/0212808 A1 | 10/2004 | Okawa et al. |
| 2004/0239938 A1 | 12/2004 | Izatt et al. |
| 2004/0246490 A1 | 12/2004 | Wang |
| 2004/0246583 A1 | 12/2004 | Mueller et al. |
| 2004/0254474 A1 | 12/2004 | Seibel et al. |
| 2004/0258106 A1 | 12/2004 | Araujo et al. |
| 2004/0263843 A1 | 12/2004 | Knopp et al. |
| 2005/0004453 A1 | 1/2005 | Tearney et al. |
| 2005/0018133 A1 | 1/2005 | Huang et al. |
| 2005/0018201 A1 | 1/2005 | de Boer et al. |
| 2005/0035295 A1 | 2/2005 | Bouma et al. |
| 2005/0036150 A1 | 2/2005 | Izatt et al. |
| 2005/0046837 A1 | 3/2005 | Izumi et al. |
| 2005/0057680 A1 | 3/2005 | Agan |
| 2005/0057756 A1 | 3/2005 | Fang-Yen et al. |
| 2005/0059894 A1 | 3/2005 | Zeng et al. |
| 2005/0065421 A1 | 3/2005 | Burckhardt et al. |
| 2005/0075547 A1 | 4/2005 | Wang |
| 2005/0083534 A1 | 4/2005 | Riza et al. |
| 2005/0119567 A1 | 6/2005 | Choi et al. |
| 2005/0128488 A1 | 6/2005 | Yelin et al. |
| 2005/0165303 A1 | 7/2005 | Kleen et al. |
| 2005/0171438 A1 | 8/2005 | Chen et al. |
| 2005/0190372 A1 | 9/2005 | Dogariu et al. |
| 2005/0197530 A1 | 9/2005 | Wallace et al. |
| 2005/0221270 A1 | 10/2005 | Connelly et al. |
| 2005/0254061 A1 | 11/2005 | Alphonse |
| 2006/0020172 A1 | 1/2006 | Luerssen et al. |
| 2006/0033923 A1 | 2/2006 | Hirasawa et al. |
| 2006/0039004 A1 | 2/2006 | De Boer et al. |
| 2006/0093276 A1 | 5/2006 | Bouma et al. |
| 2006/0103850 A1 | 5/2006 | Alphonse et al. |
| 2006/0106375 A1 | 5/2006 | Werneth et al. |
| 2006/0146339 A1 | 7/2006 | Fujita et al. |
| 2006/0155193 A1 | 7/2006 | Leonardi et al. |
| 2006/0164639 A1 | 7/2006 | Horn et al. |
| 2006/0167363 A1 | 7/2006 | Bernstein et al. |
| 2006/0171503 A1 | 8/2006 | O'Hara et al. |
| 2006/0184048 A1 | 8/2006 | Saadat et al. |
| 2006/0224053 A1 | 10/2006 | Black et al. |
| 2006/0244973 A1 | 11/2006 | Yun et al. |
| 2006/0279742 A1 | 12/2006 | Tearney |
| 2007/0002435 A1 | 1/2007 | Ye et al. |
| 2007/0019208 A1 | 1/2007 | Toida et al. |
| 2007/0038040 A1 | 2/2007 | Cense et al. |
| 2007/0070496 A1 | 3/2007 | Gweon et al. |
| 2007/0076217 A1 | 4/2007 | Baker et al. |
| 2007/0086013 A1 | 4/2007 | De Lega et al. |
| 2007/0086017 A1 | 4/2007 | Buckland et al. |
| 2007/0091317 A1 | 4/2007 | Freischlad et al. |
| 2007/0133002 A1 | 6/2007 | Wax et al. |
| 2007/0188855 A1 | 8/2007 | Shishkov et al. |
| 2007/0208225 A1 | 9/2007 | Czaniera et al. |
| 2007/0223006 A1 | 9/2007 | Tearney et al. |
| 2007/0233056 A1 | 10/2007 | Yun |
| 2007/0233396 A1 | 10/2007 | Tearney et al. |
| 2007/0236700 A1 | 10/2007 | Yun et al. |
| 2007/0258094 A1 | 11/2007 | Izatt et al. |
| 2007/0291277 A1 | 12/2007 | Everett et al. |

| | | | | | | |
|---|---|---|---|---|---|---|
| 2008/0002197 | A1 | 1/2008 | Sun et al. | JP | 2005-195485 | 7/2005 |
| 2008/0007734 | A1 | 1/2008 | Park et al. | JP | 2007271761 | 10/2007 |
| 2008/0021275 | A1 | 1/2008 | Tearney et al. | WO | 7900841 | 10/1979 |
| 2008/0049220 | A1 | 2/2008 | Izzia et al. | WO | 9201966 | 2/1992 |
| 2008/0094613 | A1 | 4/2008 | de Boer et al. | WO | 9216865 | 10/1992 |
| 2008/0094637 | A1 | 4/2008 | de Boer et al. | WO | 9219930 | 11/1992 |
| 2008/0097225 | A1 | 4/2008 | Tearney et al. | WO | 9303672 | 3/1993 |
| 2008/0097709 | A1 | 4/2008 | de Boer et al. | WO | 9216865 | 10/1993 |
| 2008/0100837 | A1 | 5/2008 | de Boer et al. | WO | 9533971 | 12/1995 |
| 2008/0152353 | A1 | 6/2008 | de Boer et al. | WO | 9628212 | 9/1996 |
| 2008/0154090 | A1 | 6/2008 | Hashimshony | WO | 9732182 | 9/1997 |
| 2008/0192236 | A1 | 8/2008 | Smith et al. | WO | 9800057 | 1/1998 |
| 2008/0204762 | A1 | 8/2008 | Izatt et al. | WO | 9801074 | 1/1998 |
| 2008/0228086 | A1 | 9/2008 | Ilegbusi | WO | 9814132 | 4/1998 |
| 2008/0234560 | A1 | 9/2008 | Nomoto et al. | WO | 9835203 | 8/1998 |
| 2008/0265130 | A1 | 10/2008 | Colomb et al. | WO | 9838907 | 9/1998 |
| 2008/0308730 | A1 | 12/2008 | Vizi et al. | WO | 9846123 | 10/1998 |
| 2009/0005691 | A1 | 1/2009 | Huang | WO | 9848838 | 11/1998 |
| 2009/0011948 | A1 | 1/2009 | Unlu et al. | WO | 9848846 | 11/1998 |
| 2009/0051923 | A1 | 2/2009 | Zuluaga et al. | WO | 9905487 | 2/1999 |
| 2009/0131801 | A1 | 5/2009 | Suter et al. | WO | 9944089 | 2/1999 |
| 2009/0192358 | A1 | 7/2009 | Jaffer et al. | WO | 9944089 | 9/1999 |
| 2009/0196477 | A1 | 8/2009 | Cense et al. | WO | 99-45338 | 10/1999 |
| 2009/0273777 | A1 | 11/2009 | Yun et al. | WO | 9957507 | 11/1999 |
| 2009/0281390 | A1 | 11/2009 | Qiu et al. | WO | 00-42906 | 7/2000 |
| 2009/0290156 | A1 | 11/2009 | Popescu et al. | WO | 0058766 | 10/2000 |
| 2009/0305309 | A1 | 12/2009 | Chien et al. | WO | 0101111 | 1/2001 |
| 2010/0002241 | A1 | 1/2010 | Hirose | WO | 0108579 | 2/2001 |
| 2010/0086251 | A1 | 4/2010 | Xu et al. | WO | 0127679 | 4/2001 |
| 2010/0094576 | A1 | 4/2010 | de Boer et al. | WO | 0138820 | 5/2001 |
| 2010/0150467 | A1 | 6/2010 | Zhao et al. | WO | 0142735 | 6/2001 |
| | | | | WO | 0236015 | 5/2002 |
| | | | | WO | 0237075 | 5/2002 |

FOREIGN PATENT DOCUMENTS

| | | | | | |
|---|---|---|---|---|---|
| DE | 4105221 | 9/1991 | WO | 0238040 | 5/2002 |
| DE | 4309056 | 9/1994 | WO | 02053050 | 7/2002 |
| DE | 19542955 | 5/1997 | WO | 02054027 | 7/2002 |
| DE | 10351319 | 6/2005 | WO | 02-083003 | 10/2002 |
| EP | 0110201 | 6/1984 | WO | 02084263 | 10/2002 |
| EP | 0251062 | 1/1988 | WO | 03-012405 | 2/2003 |
| EP | 0617286 | 2/1994 | WO | 03013624 | 2/2003 |
| EP | 0590268 | 4/1994 | WO | 03020119 | 3/2003 |
| EP | 0728440 | 8/1996 | WO | 03046495 | 6/2003 |
| EP | 0933096 | 8/1999 | WO | 03046636 | 6/2003 |
| EP | 1324051 | 7/2003 | WO | 03052478 | 6/2003 |
| EP | 1426799 | 6/2004 | WO | 03053226 | 7/2003 |
| FR | 2738343 | 8/1995 | WO | 03062802 | 7/2003 |
| GB | 1257778 | 12/1971 | WO | 03-088826 | 10/2003 |
| GB | 2030313 | 4/1980 | WO | 03105678 | 12/2003 |
| GB | 2209221 | 5/1989 | WO | 2004034869 | 4/2004 |
| GB | 2298054 | 8/1996 | WO | 2004-043251 | 5/2004 |
| JP | 6073405 | 4/1985 | WO | 2004057266 | 7/2004 |
| JP | 62-188001 | 6/1989 | WO | 2004066824 | 8/2004 |
| JP | 04-056907 | 2/1992 | WO | 2004088361 | 10/2004 |
| JP | 20040056907 | 2/1992 | WO | 2004105598 | 12/2004 |
| JP | 4135550 | 5/1992 | WO | 2005000115 | 1/2005 |
| JP | 4135551 | 5/1992 | WO | 2005047813 | 5/2005 |
| JP | 5509417 | 11/1993 | WO | 2005054780 | 6/2005 |
| JP | 9-230248 | 9/1997 | WO | 2005082225 | 9/2005 |
| JP | 10-267631 | 10/1998 | WO | 2006004743 | 1/2006 |
| JP | 2000-046729 | 2/2000 | WO | 2006014392 | 2/2006 |
| JP | 2000-121961 | 4/2000 | WO | 2006038876 | 4/2006 |
| JP | 2000-504234 | 4/2000 | WO | 2006039091 | 4/2006 |
| JP | 2001-174404 | 6/2001 | WO | 2006059109 | 6/2006 |
| JP | 2001-174744 | 6/2001 | WO | 2006124860 | 11/2006 |
| JP | 2001-508340 | 6/2001 | WO | 2006130797 | 12/2006 |
| JP | 2007-539336 | 6/2001 | WO | 2007028531 | 3/2007 |
| JP | 2001-212086 | 8/2001 | WO | 2007038787 | 4/2007 |
| JP | 2001-525580 | 12/2001 | WO | 2007083138 | 7/2007 |
| JP | 2002-205434 | 2/2002 | WO | 2007084995 | 7/2007 |
| JP | 2002-095663 | 4/2002 | WO | 2009153929 | 12/2009 |
| JP | 2002214127 | 7/2002 | WO | 2011-055376 | 5/2011 |
| JP | 2003-014585 | 1/2003 | | | |
| JP | 2003-504627 | 2/2003 | | | |
| JP | 20030035659 | 2/2003 | | | |
| JP | 2003-512085 | 4/2003 | | | |
| JP | 2003-513278 | 4/2003 | | | |
| JP | 2003-516531 | 5/2003 | | | |
| JP | 2005-062850 | 3/2005 | | | |
| JP | 2005-110208 | 4/2005 | | | |

OTHER PUBLICATIONS

D. Huang et al., "Optical Coherence Tomography," *Science*, vol. 254, pp. 1178-1181, Nov. 1991.

Tearney et al., "High-Speed Phase -and Delay Scanning with a Grating Based Phase Control Delay Line," *Optics Letters*, vol. 22, pp. 1811-1813, Dec. 1997.

Rollins, et al., "In Vivo Video Rate Optical Coherence Tomography," *Optics Express*, vol. 3, pp. 219-229, Sep. 1998.

Saxer, et al., High Speed Fiber-Based Polarization-Sensitive Optical Coherence Tomography of in Vivo Human Skin, *Optical Society of America*, vol. 25, pp. 1355-1357, Sep. 2000.

Oscar Eduardo Martinez, "3000 Times Grating Compress or with Positive Group Velocity Dispersion," *IEEE*, vol. QE-23, pp. 59-64, Jan. 1987.

Kulkarni, et al., "Image Enhancement in Optical Coherence Tomography Using Deconvolution," *Electronics Letters*, vol. 33, pp. 1365-1367, Jul. 1997.

Bashkansky, et al., "Signal Processing for Improving Field Cross-Correlation Function in Optical Coherence Tomography," *Optics & Photonics News*, vol. 9, pp. 8137-8138, May 1998.

Yung et al., "Phase-Domain Processing Journal of Optical Coherence Tomography Images," *Journal of Biomedical Optics*, vol. 4, pp. 125-136, Jan. 1999.

Tearney, et al., "In Vivo Endoscopic Optical Biopsy with Optical Coherence Tomography," *Science*, vol. 276, Jun. 1997.

W. Drexler et al., "In Vivo Ultrahigh-Resolution Optical Coherence Tomography," *Optics Letters* vol. 24, pp. 1221-1223, Sep. 1999.

Nicusor V. Iftimia et al., (2005) "A Portable, Low Coherence Interferometry Based Instrument for Fine Needle Aspiration Biopsy Guidance," Accepted to Review of Scientific Instruments, published May 23, 2005.

Abbas, G.L., V.W.S. Chan et al., "Local-Oscillator Excess-Noise Suppression for Homodyne and Heterodyne-Detection," *Optics Letters*, vol. 8, pp. 419-421, Aug. 1983 issue.

Agrawal, G.P., "Population Pulsations and Nondegenerate 4-Wave Mixing in Semiconductor-Lasers and Amplifiers," *Journal of the Optical Society of America B-Optical Physics*, vol. 5, pp. 147-159, Jan. 1998.

Andretzky, P. et al., "Optical Coherence Tomography by Spectral Radar: Improvement of Signal-to-Noise Ratio," *The International Society for Optical Engineering*, USA, vol. 3915, 2000.

Ballif, J. et al., "Rapid and Scalable Scans at 21 m/s in optical Low-Coherence Reflectometry," *Optics Letters*, vol. 22, pp. 757-759, Jun. 1997.

Barfuss H. et al., "Modified Optical Frequency-Domain Reflectometry with High Spatial-Resolution for Components of Integrated Optic Systems," *Journal of Lightwave Technology*, vol. 7, pp. 3-10, Jan. 1989.

Beaud, P. et al., "Optical Reflectometry with Micrometer Resolution for the Investigation of Integrated Optical-Devices," *Leee Journal of Quantum Electronics*, vol. 25, pp. 755-759, Apr. 1989.

Bouma, Brett et al., "Power-Efficient Nonreciprocal Interferometer and Linear-Scanning Fiber-Optic Catheter for Optical Coherence Tomography," *Optics Letters*, vol. 24, pp. 531-533, Apr. 1999.

Brinkmeyer, E. et al., "Efficient Algorithm for Non-Equidistant Interpolation of Sampled Data," *Electronics Letters*, vol. 28, p. 693, Mar. 1992.

Brinkmeyer, E. et al., "High-Resolution OCDR in Dispersive Wave-Guides," *Electronics Letters*, vol. 26, pp. 413-414, Mar. 1990.

Chinn, S.R. et al., "Optical Coherence Tomography Using a Frequency-Tunable Optical Source," *Optics Letters*, vol. 22, pp. 340-342, Mar. 1997.

Danielson, B.L. et al., "Absolute Optical Ranging Using Low Coherence Interferometry," *Applied Optics*, vol. 30, p. 2975, Jul. 1991.

Dorrer, C. et al., "Spectral Resolution and Sampling Issues in Fourier-Transform Spectral Interferometry," *Journal of the Optical Society of America B-Optical Physics*, vol. 17, pp. 1795-1802, Oct. 2000.

Dudley, J.M. et al., "Cross-Correlation Frequency Resolved Optical Gating Analysis of Broadband Continuum Generation in Photonic Crystal Fiber: Simulations and Experiments," *Optics Express*, vol. 10, p. 1215, Oct. 2002.

Eickhoff, W. et al., "Optical Frequency-Domain Reflectometry in Single-Mode Fiber," *Applied Physics Letters*, vol. 39, pp. 693-695, 1981.

Fercher, Adolf "Optical Coherence Tomography," *Journal of Biomedical Optics*, vol. 1, pp. 157-173, Apr. 1996.

Ferreira, L.A. et al., "Polarization-Insensitive Fiberoptic White-Light Interferometry," *Optics Communications*, vol. 114, pp. 386-392, Feb. 1995.

Fujii, Yohji, "High-Isolation Polarization-Independent Optical Circulator", *Journal of Lightwave Technology*, vol. 9, pp. 1239-1243, Oct. 1991.

Glance, B., "Polarization Independent Coherent Optical Receiver," *Journal of Lightwave Technology*, vol. LT-5, p. 274, Feb. 1987.

Glombitza, U., "Coherent Frequency—Domain Reflectometry for Characterization of Single-Mode Integrated-Optical Wave-Guides," *Journal of Lightwave Technology*, vol. 11, pp. 1377-1384, Aug. 1993.

Golubovic, B. et al., "Optical Frequency-Domain Reflectometry Using Rapid Wavelength Tuning of a Cr4+:Forsterite Laser," *Optics Letters*, vol. 11, pp. 1704-1706, Nov. 1997.

Haberland, U. H. P. et al., "Chirp Optical Coherence Tomography of Layered Scattering Media," *Journal of Biomedical Optics*, vol. 3, pp. 259-266, Jul. 1998.

Hammer, Daniel X. et al., "Spectrally Resolved White-Light Interferometry for Measurement of Ocular Dispersion," *Journal of the Optical Society of America A-Optics Image Science and Vision*, vol. 16, pp. 2092-2102, Sep. 1999.

Harvey, K. C. et al., "External-Cavity Diode-Laser Using a Grazing-Incidence Diffraction Grating," *Optics Letters*, vol. 16, pp. 910-912, Jun. 1991.

Hausler, Gerd et al., "'Coherence Radar' and 'Spectral Radar' New Tools for Dermatological Diagnosis," *Journal of Biomedical Optics*, vol. 3, pp. 21-31, Jan. 1998.

Hee, Michael R. et al., "Polarization-Sensitive Low-Coherence Reflectometer for Birefringence Characterization and Ranging," *Journal of the Optical Society of American B (Optical Physics)*, vol. 9, p. 903-908, Jun. 1992.

Hotate Kazuo et al., "Optical Coherence Domain Reflectometry by Synthesis of Coherence Function," *Journal of Lightwave Technology*, vol. 11, pp. 1701-1710, Oct. 1993.

Inoue, Kyo et al., "Nearly Degenerate 4-Wave-Mixing in a Traveling-Wave Semiconductor-Laser Amplifier," *Applied Physics Letters*, vol. 51, pp. 1051-1053, 1987.

Ivanov, A. P. et al., "New Method for High-Range Resolution Measurements Of light Scattering in Optically Dense Inhomogenous Media," *Optics Letters*, vol. 1, pp. 226-228, Dec. 1977.

Ivanov, A. P. et al., "Interferometric Study of the Spatial Structure of a Light-Scattering Medium," *Journal of Applied Spectroscopy*, vol. 28, pp. 518-525, 1978.

Kazovsky, L. G. et al., "Heterodyne Detection Through Rain, Snow, and Turbid Media: Effective Receiver Size at Optical Through Millimeter Wavelenghths," *Applied Optics*, vol. 22, pp. 706-710, Mar. 1983.

Kersey, A. D. et al., "Adaptive Polarization Diversity Receiver Configuration for Coherent Optical Fiber Communications," *Electronics Letters*, vol. 25, pp. 275-277, Feb. 1989.

Kohlhaas, Andreas et al., "High-Resolution OCDR for Testing Integrated-Optical Waveguides: Dispersion-Corrupted Experimental Data Corrected by a Numerical Algorithm," *Journal of Lightwave Technology*, vol. 9, pp. 1493-1502, Nov. 1991.

Larkin, Kieran G., "Efficient Nonlinear Algorithm for Envelope Detection in White Light Interferometry," *Journal of the Optical Society of America A-Optics Image Science and Vision*, vol. 13, pp. 832-843, Apr. 1996.

Leitgeb, R. et al., "Spectral measurement of Absorption by Spectroscopic Frequency-Domain Optical Coherence Tomography," *Optics Letters*, vol. 25, pp. 820-822, Jun. 2000.

Lexer, F. et al., "Wavelength-Tuning Interferometry of Intraocular Distances," *Applied Optics*, vol. 36, pp. 6548-6553, Sep. 1997.

Mitsui, Takahisa, "Dynamic Range of Optical Reflectometry with Spectral Interferometry," *Japanese Journal of Applied Physics Part 1—Regular Papers Short Notes & Review Papers*, vol. 38, pp. 6133-6137, 1999.

Naganuma, Kazunori et al., "Group-Delay Measurement Using the Fourier-Transform of an Interferometric Cross-Correlation Generated by White Light," *Optics Letters*, vol. 15, pp. 393-395, Apr. 1990.

Okoshi,Takanori, "Polarization-State Control Schemes for Heterodyne or Homodyne Optical Fiber Communications," *Journal of Lightwave Technology*, vol. LT-3, pp. 1232-1237, Dec. 1995.

Passy, R. et al., "Experimental and Theoretical Investigations of Coherent OFDR with Semiconductor-Laser Sources," *Journal of Lightwave Technology*, vol. 12, pp. 1622-1630, Sep. 1994.

Podoleanu, Adrian G., "Unbalanced Versus Balanced Operation in an Optical Coherence Tomography System," *Applied Optics*, vol. 39, pp. 173-182, Jan. 2000.

Price, J. H. V. et al., "Tunable, Femtosecond Pulse Source Operating in the Range 1.06-1.33 mu m Based on an Yb3+-doped Holey Fiber Amplifier," *Journal of the Optical Society of America B-Optical Physics*, vol. 19, pp. 1286-1294, Jun. 2002.

Schmitt, J. M. et al, "Measurement of Optical-Properties of Biological Tissues by Low-Coherence Reflectometry," *Applied Optics*, vol. 32, pp. 6032-6042, Oct. 1993.

Silberberg, Y. et al., "Passive-Mode Locking of a Semiconductor Diode-Laser," *Optics Letters*, vol. 9, pp. 507-509, Nov. 1984.

Smith, L. Montgomery et al., "Absolute Displacement Measurements Using Modulation of the Spectrum of White-Light in a Michelson Interferometer," *Applied Optics*, vol. 28, pp. 3339-3342, Aug. 1989.

Sonnenschein, C. M. et al., "Signal-To-Noise Relationships for Coaxial Systems that Heterodyne Backscatter from Atmosphere," *Applied Optics*, vol. 10, pp. 1600-1604, Jul. 1971.

Sorin, W. V. et al., "Measurement of Rayleigh Backscattering at 1.55 mu m with 32 mu m Spatial Resolution," *IEEE Photonics Technology Letters*, vol. 4, pp. 374-376, Apr. 1992.

Sorin, W. V. et al., "A Simple Intensity Noise-Reduction Technique for Optical Low-Coherence Reflectometry," *IEEE Photonics Technology Letters*, vol. 4, pp. 1404-1406, Dec. 1992.

Swanson, E. A. et al., "High-Speed Optical Coherence Domain Reflectometry," *Optics Letters*, vol. 17, pp. 151-153, Jan. 1992.

Takada, K. et al., "High-Resolution OFDR with Incorporated Fiberoptic Frequency Encoder," *IEEE Photonics Technology Letters*, vol. 4, pp. 1069-1072, Sep. 1992.

Takada, Kazumasa et al., "Narrow-Band light Source with Acoustooptic Tunable Filter for Optical Low-Coherence Reflectometry," *IEEE Photonics Technology Letters*, vol. 8, pp. 658-660, May 1996.

Takada, Kazumasa et al., "New Measurement System for Fault Location in Optical Wave-Guide Devices Based on an Interometric-Technique," *Applied Optics*, vol. 26, pp. 1603-1606, May 1987.

Tateda, Mitsuhiro et al., "Interferometric Method for Chromatic Dispersion Measurement in a Single-Mode Optical Fiber," *IEEE Journal of Quantum Electronics*, vol. 17, pp. 404-407, Mar. 1981.

Toide, M. et al., "Two-Dimensional Coherent Detection Imaging in Multiple Scattering Media Based the Directional Resolution Capability of the Optical Heterodyne Method," *Applied Physics B (Photophysics and Laser Chemistry)*, vol. B52, pp. 391-394, 1991.

Trutna, W. R. et al., "Continuously Tuned External-Cavity Semiconductor-Laser," *Journal of Lightwave Technology*, vol. 11, pp. 1279-1286, Aug. 1993.

Uttam, Deepak et al., "Precision Time Domain Reflectometry in Optical Fiber Systems Using a Frequency Modualted Continuous Wave Ranging Technique," *Journal of Lightwave Technology*, vol. 3, pp. 971-977, Oct. 1985.

Von Der Weid, J. P. et al., "On the Characterization of Optical Fiber Network Components with Optical Frequency Domain Reflectometry," *Journal of Lightwave Technology*, vol. 15, pp. 1131-1141, Jul. 1997.

Wysocki, P.F. et al., "Broad-Spectrum, Wavelength-Swept, Erbium-Doped Fiber Laser at 1.55-Mu-M," *Optics Letters*, vol. 15, pp. 879-881, Aug. 1990.

Youngquist, Robert C. et al., "Optical Coherence-Domain Reflectometry—A New Optical Evaluation Technique," *Optics Letters*, vol. 12, pp. 158-160, Mar. 1987.

Yun, S. H. et al., "Wavelength-Swept Fiber Laser with Frequency Shifted Feedback and Resonantly Swept Intra-Cavity Acoustooptic Tunable Filter," *IEEE Journal of Selected Topics in Quantum Electronics*, vol. 3, pp. 1087-1096, Aug. 1997.

Yun, S. H. et al., "Interrogation of Fiber Grating Sensor Arrays with a Wavelength-Swept Fiber Laser," *Optics Letters*, vol. 23, pp. 843-845, Jun. 1998.

Yung, K. M., "Phase-Domain Processing of Optical Coherence Tomography Images," *Journal of Biomedical Optics*, vol. 4, pp. 125-136, Jan. 1999.

Zhou, Xiao-Qun et al., "Extended-Range FMCW Reflectometry Using an optical Loop with a Frequency Shifter," *IEEE Photonics Technology Letters*, vol. 8, pp. 248-250, Feb. 1996.

Zorabedian, Paul et al., "Tuning Fidelity of Acoustooptically Controlled External Cavity Semiconductor-Lasers," *Journal of Lightwave Technology*, vol. 13, pp. 62-66, Jan. 1995.

Victor S. Y. Lin et al., "A Porous Silicon-Based Optical Interferometric Biosensor," *Science Magazine*, vol. 278, pp. 840-843, Oct. 31, 1997.

De Boer, Johannes F. et al., "Review of Polarization Sensitive Optical Coherence Tomography and Stokes Vector Determination," *Journal of Biomedical Optics*, vol. 7, No. 3, Jul. 2002, pp. 359-371.

Jiao, Shuliang et al., "Depth-Resolved Two-Dimensional Stokes Vectors of Backscattered Light and Mueller Matrices of Biological Tissue Measured with Optical Coherence Tomography," *Applied Optics*, vol. 39, No. 34, Dec. 1, 2000, pp. 6318-6324.

Park, B. Hyle et al., "In Vivo Burn Depth Determination by High-Speed Fiber-Based Polarization Sensitive Optical Coherence Tomography," *Journal of Biomedical Optics*, vol. 6 No. 4, Oct. 2001, pp. 474-479.

Roth, Jonathan E. et al., "Simplified Method for Polarization-Sensitive Optical Coherence Tomography," *Optics Letters*, vol. 26, No. 14, Jul. 15, 2001, pp. 1069-1071.

Hitzenberger, Christopher K. et al., "Measurement and Imaging of Birefringence and Optic Axis Orientation by Phase Resolved Polarization Sensitive Optical Coherence Tomography," *Optics Express*, vol. 9, No. 13, Dec. 17, 2001, pp. 780-790.

Wang, Xuedong et al., (2001) "Propagation of Polarized Light in Birefringent Turbid Media: Time-Resolved Simulations," Optical Imaging Laboratory, Biomedical Engineering Program, Texas A&M University, Aug. 27, 2001, pp. 254-259.

Wong, Brian J.F. et al., "Optical Coherence Tomography of the Rat Cochlea," Journal of *Biomedical Optics*, vol. 5, No. 4, Oct. 2000, pp. 367-370.

Yao, Gang et al., "Propagation of Polarized Light in Turbid Media: Simulated Animation Sequences," *Optics Express*, vol. 7, No. 5, Aug. 28, 2000, pp. 198-203.

Wang, Xiao-Jun et al., "Characterization of Dentin and Enamel by Use of Optical Coherence Tomography," *Applied Optics*, vol. 38, No. 10, Apr. 1, 1999, pp. 2092-2096.

De Boer, Johannes F. et al., "Determination of the Depth-Resolved Stokes Parameters of Light Backscattered from Turbid Media by use of Polarization-Sensitive Optical Coherence Tomography," *Optics Letters*, vol. 24, No. 5, Mar. 1, 1999, pp. 300-302.

Ducros, Mathieu G. et al., "Polarization Sensitive Optical Coherence Tomography of the Rabbit Eye," *IEEE Journal of Selected Topcis in Quantum Electronics*, vol. 5, No. 4, Jul./Aug. 1999, pp. 1159-1167.

Groner, Warren et al., "Orthogonal Polarization Spectral Imaging: A New Method for Study of the Microcirculation," *Nature Medicine Inc.*, vol. 5 No. 10, Oct. 1999, pp. 1209-1213.

De Boer, Johannes F. et al., "Polarization Effects in Optical Coherence Tomography of Various Viological Tissues," *IEEE Journal of Selected Topics in Quantum Electronics*, vol. 5, No. 4, Jul./Aug. 1999, pp. 1200-1204.

Yao, Gang et al., "Two-Dimensional Depth-Resolved Mueller Matrix Characterization of Biological Tissue by Optical Coherence Tomography," *Optics Letters*, Apr. 15, 1999, vol. 24, No. 8, pp. 537-539.

Lu, Shih-Yau et al., "Homogeneous and Inhomogeneous Jones Matrices," *J. Opt. Soc. Am. A.*, vol. 11, No. 2, Feb. 1994, pp. 766-773.

Bickel, S. William et al., "Stokes Vectors, Mueller Matrices, and Polarized Scattered Light," *Am. J. Phys.*, vol. 53, No. 5, May 1985 pp. 468-478.

Bréhonnet, F. Le Roy et al., "Optical Media and Target Characterization by Mueller Matrix Decomposition," *J. Phys. D: Appl. Phys.* 29, 1996, pp. 34-38.

Cameron, Brent D. et al., "Measurement and Calculation of the Two-Dimensional Backscattering Mueller Matrix of a Turbid Medium," *Optics Letters*, vol. 23, No. 7, Apr. 1, 1998, pp. 485-487.

De Boer, Johannes F. et al., "Two-Dimensional Birefringence Imaging in Biological Tissue by Polarization-Sensitive Optical Coherence Tomography," *Optics Letters*, vol. 22, No. 12, Jun. 15, 1997, pp. 934-936.

De Boer, Johannes F. et al., "Imaging Thermally Damaged Tissue by Polarization Sensitive Optical Coherence Tomography," *Optics Express*, vol. 3, No. 6, Sep. 14, 1998, pp. 212-218.

Everett, M.J. et al., "Birefringence Characterization of Biological Tissue by Use of Optical Coherence Tomography," *Optics Letters*, vol. 23, No. 3, Feb. 1, 1998, pp. 228-230.

Hee, Michael R. et al., "Polarization-Sensitive Low-Coherence Reflectometer for Birefringence Characterization and Ranging," *J. Opt. Soc. Am. B.*, vol. 9, No. 6, Jun. 1992, pp. 903-908.

Barakat, Richard, "Statistics of the Stokes Parameters," *J. Opt. Soc. Am. B.*, vol. 4, No. 7, Jul. 1987, pp. 1256-1263.

Schmitt, J.M. et al., "Cross-Polarized Backscatter in Optical Coherence Tomography of Biological Tissue," *Optics Letters*, vol. 23, No. 13, Jul. 1, 1998, pp. 1060-1062.

Schoenenberger, Klaus et al., "Mapping of Birefringence and Thermal Damage in Tissue by use of Polarization-Sensitive Optical Coherence Tomography," *Applied Optics*, vol. 37, No. 25, Sep. 1, 1998, pp. 6026-6036.

Pierce, Mark C. et al., "Simultaneous Intensity, Birefringence, and Flow Measurements with High-Speed Fiber-Based Optical Coherence Tomography," *Optics Letters*, vol. 27, No. 17, Sep. 1, 2002, pp. 1534-1536.

De Boer, Johannes F. et al., "Review of Polarization Sensitive Optical Coherence Tomography and Stokes Vector Determination," *Journal of Biomedical Optics*, Jul. 2002, vol. 7, No. 3, pp. 359-371.

Fried, Daniel et al., "Imaging Caries Lesions and Lesion Progression with Polarization Sensitive Optical Coherence Tomography," *Journal of Biomedical Optics*, vol. 7, No. 4, Oct. 2002, pp. 618-627.

Jiao, Shuliang et al., "Two-Dimensional Depth-Resolved Mueller Matrix of Biological Tissue Measured with Double-Beam Polarization-Sensitive Optical Coherence Tomography," *Optics Letters*, vol. 27, No. 2, Jan. 15, 2002, pp. 101-103.

Jiao, Shuliang et al., "Jones-Matrix Imaging of Biological Tissues with Quadruple-Channel Optical Coherence Tomography," *Journal of Biomedical Optics*, vol. 7, No. 3, Jul. 2002, pp. 350-358.

Kuranov, R.V. et al., "Complementary Use of Cross-Polarization and Standard OCT for Differential Diagnosis of Pathological Tissues," *Optics Express*, vol. 10, No. 15, Jul. 29, 2002, pp. 707-713.

Cense, Barry et al., "In Vivo Depth-Resolved Birefringence Measurements of the Human Retinal Nerve Fiber Layer by Polarization-Sensitive Optical Coherence Tomography," *Optics Letters*, vol. 27, No. 18, Sep. 15, 2002, pp. 1610-1612.

Ren, Hongwu et al., "Phase-Resolved Functional Optical Coherence Tomography: Simultaneous Imaging of In Situ Tissue Structure, Blood Flow Velocity, Standard Deviation, Birefringence, and Stokes Vectors in Human Skin," *Optics Letters*, vol. 27, No. 19, Oct. 1, 2002, pp. 1702-1704.

Tripathi, Renu et al., "Spectral Shaping for Non-Gaussian Source Spectra in Optical Coherence Tomography," *Optics Letters*, vol. 27, No. 6, Mar. 15, 2002, pp. 406-408.

Yasuno, Y. et al., "Birefringence Imaging of Human Skin by Polarization-Sensitive Spectral Interferometric Optical Coherence Tomography," *Optics Letters*, vol. 27, No. 20, Oct. 15, 2002 pp. 1803-1805.

White, Brian R. et al., "In Vivo Dynamic Human Retinal Blood Flow Imaging Using Ultra-High Speed Spectral Domain Optical Doppler Tomography," *Optics Express*, vol. 11, No. 25, Dec. 15, 2003, pp. 3490-3497.

De Boer, Johannes F. et al., "Improved Signal-to-Noise Ratio in Spectral-Domain Compared with Time-Domain Optical Coherence Tomography," *Optics Letters*, vol. 28, No. 21, Nov. 1, 2003, pp. 2067-2069.

Jiao, Shuliang et al., "Optical-Fiber-Based Mueller Optical Coherence Tomography," *Optics Letters*, vol. 28, No. 14, Jul. 15, 2003, pp. 1206-1208.

Jiao, Shuliang et al., "Contrast Mechanisms in Polarization-Sensitive Mueller-Matrix Optical Coherence Tomography and Application in Burn Imaging," *Applied Optics*, vol. 42, No. 25, Sep. 1, 2003, pp. 5191-5197.

Moreau, Julien et al., "Full-Field Birefringence Imaging by Thermal-Light Polarization-Sensitive Optical Coherence Tompgrahy. I. Theory," *Applied Optics*, vol. 42, No. 19, Jul. 1, 2003, pp. 3800-3810.

Moreau, Julien et al., "Full-Field Birefringence Imaging by Thermal-Light Polarization-Sensitive Optical Coherence Tomography. II. Instrument and Results," *Applied Optics*, vol. 42, No. 19, Jul. 1, 2003, pp. 3811-3818.

Morgan, Stephen P. et al., "Surface-Reflection Elimination in Polarization Imaging of Superficial Tissue," *Optics Letters*, vol. 28, No. 2, Jan. 15, 2003, pp. 114-116.

Oh, Jung-Taek et al., "Polarization-Sensitive Optical Coherence Tomography for Photoelasticity Testing of Glass/Epoxy Composites," *Optics Express*, vol. 11, No. 14, Jul. 14, 2003, pp. 1669-1676.

Park, B. Hyle et al., "Real-Time Multi-Functiona Optical Coherence Tomography," *Optics Express*, vol. 11, No. 7, Apr. 7, 2003, pp. 782-793.

Shribak, Michael et al., "Techniques for Fast and Sensitive Measurements of Two-Dimensional Birefringence Distributions," *Applied Optics*, vol. 42, No. 16, Jun. 1, 2003, pp. 3009-3017.

Somervell, A.R.D. et al., "Direct Measurement of Fringe Amplitude and Phase Using a Heterodyne Interferometer Operating in Broadband Light," *Elsevier, Optics Communications*, Oct. 2003.

Stiffer, D. et al., "Polarisation-Sensitive Optical Coherence Tomography for Material Characterisation and Strain-Field Mapping," Applied Physics A 76, Materials Science & Processing, Jan. 2003, pp. 947-951.

Davé, Digant P. et al., "Polarization-Maintaining Fiber-Based Optical Low-Coherence Reflectometer for Characterization and Ranging of Birefringence," *Optics Letters*, vol. 28, No. 19, Oct. 1, 2003, pp. 1775-1777.

Yang, Ying et al., "Observations of Birefringence in Tissues from Optic-Fibre-Based Optical Coherence Tomography," *Measurement Science and Technology*, Nov. 2002, pp. 41-46.

Yun, S.H. et al., "High-Speed Optical Frequency-Domain Imaging," *Optics Express*, vol. 11, No. 22, Nov. 3, 2003, pp. 2953-2963.

Yun, S.H. et al., "High-Speed Spectral-Domain Optical Coherence Tomography at 1.3 µm Wavelength," *Optics Express*, vol. 11, No. 26, Dec. 29, 2003, pp. 3598-3604.

Zhang, Jun et al., "Determination of Birefringence and Absolute Optic Axis Orientation Using Polarization-Sensitive Optical Coherence Tomography with PM Fibers," *Optics Express*, vol. 11, No. 24, Dec. 1, 2003, pp. 3262-3270.

Pircher, Michael et al., "Three Dimensional Polarization Sensitive OCT of Human Skin In Vivo," *Optical Society of America*.

Götzinger, Erich et al., "Measurement and Imaging of Birefringent Properties of the Human Cornea with Phase-Resolved, Polarization-Sensitive Optical Coherence Tomography," *Journal of Biomedical Optics*, vol. 9, No. 1, Jan./Feb. 2004, pp. 94-102.

Guo, Shuguang et al., "Depth-Resolved Birefringence and Differential Optical Axis Orientation Measurements with Finer-based Polarization-Sensitive Optical Coeherence Tomography," *Optics Letters*, vol. 29, No. 17, Sep. 1, 2004, pp. 2025-2027.

Huang, Xiang-Run et al.,"Variation of Peripapillary Retinal Nerve Fiber Layer Birefringence in Normal Human Subjects," *Investigative Ophthalmology & Visual Science*, vol. 45, No. 9, Sep. 2004, pp. 3073-3080.

Matcher, Stephen J. et al., "The Collagen Structure of Bovine Intervertebral Disc Studied Using Polarization-Sensitive Optical Coherence Tomography," *Physics in Medicine and Biology*, 2004, pp. 1295-1306.

Nassif, Nader et al., "In Vivo Human Retinal Imaging by Ultrahigh-Speed Spectral Domain Optical Coherence Tomography," *Optics Letters*, vol. 29, No. 5, Mar. 1, 2004, pp. 480-482.

Nassif, N.A. et al., "In Vivo High-Resolution Video-Rate Spectral-Domain Optic Coherence Tomography of the Human Retina and Optic Nerve," *Optics Express*, vol. 12, No. 3, Feb. 9, 2004, pp. 367-376.

Park, B. Hyle et al., "Comment on Optical-Fiber-Based Mueller Optical Coherence Tomography," *Optics Letters*, vol. 29, No. 24, Dec. 15, 2004, pp. 2873-2874.

Park, B. Hyle et al., "Jones Matrix Analysis for a Polarization-Sensitive Optical Coherence Tomography System Using Fiber-Optic Components," *Optics Letters*, vol. 29, No. 21, Nov. 1, 2004, pp. 2512-2514.

Pierce, Mark C. et al., "Collagen Denaturation can be Quantified in Burned Human Skin Using Polarization-Sensitive Optical Coherence Tomography," *Elsevier, Burns*, 2004, pp. 511-517.

Pierce, Mark C. et al., "Advances in Optical Coherence Tomography Imaging for Dermatology," *The Society for Investigative Dermatology, Inc.* 2004, pp. 458-463.

Pierce, Mark C. et al., "Birefringence Measurements in Human Skin Using Polarization-Sensitive Optical Coherence Tomography," *Journal of Biomedical Optics*, vol. 9, No. 2, Mar./Apr. 2004, pp. 287-291.

Cense, Barry et al., "In Vivo Birefringence and Thickness Measurements of the Human Retinal Nerve Fiber Layer Using Polarization-Sensitive Optical Coherence Tomography," *Journal of Biomedical Optics*, vol. 9, No. 1, Jan./Feb. 2004, pp. 121-125.

Pircher, Michael et al., "Imaging of Polarization Properties of Human Retina in Vivo with Phase Resolved Transversal PS-OCT," *Optics Express*, vol. 12, No. 24, Nov. 29, 2004 pp. 5940-5951.

Pircher, Michael et al., "Transversal Phase Resolved Polarization Sensitive Optical Coherence Tomography," *Physics in Medicine & Biology*, 2004, pp. 1257-1263.

Srinivas, Shyam M. et al., "Determination of Burn Depth by Polarization-Sensitive Optical Coherence Tomography," *Journal of Biomedical Optics*, vol. 9, No. 1, Jan./Feb. 2004, pp. 207-212.

Strasswimmer, John et al., "Polarization-Sensitive Optical Coherence Tomography of Invasive Basal Cell Carcinoma," *Journal of Biomedical Optics*, vol. 9, No. 2, Mar./Apr. 2004, pp. 292-298.

Todorović, Miloš et al., "Determination of Local Polarization Properties of Biological Samples in the Presence of Diattenuation by use of Mueller Optical Coherence Tomography," *Optics Letters*, vol. 29, No. 20, Oct. 15, 2004, pp. 2402-2404.

Yasuno, Yoshiaki et al., "Polarization-Sensitive Complex Fourier Domain Optical Coherence Tomography for Jones Matrix Imaging of Biological Samples," Applied Physics Letters, vol. 85, No. 15, Oct. 11, 2004, pp. 3023-3025.

Acioli, L. H., M. Ulman, et al. (1991). "Femtosecond Temporal Encoding in Barium-Titanate." *Optics Letters* 16(24): 1984-1986.

Aigouy, L., A. Lahrech, et al. (1999). "Polarization effects in apertureless scanning near-field optical microscopy: an experimental study." *Optics Letters* 24(4): 187-189.

Akiba, M., K. P. Chan, et al. (2003). "Full-field optical coherence tomography by two-dimensional heterodyne detection with a pair of CCD cameras." *Optics Letters* 28(10): 816-818.

Akkin, T., D. P. Dave, et al. (2004). "Detection of neural activity using phase-sensitive optical low-coherence reflectometry." *Optics Express* 12(11):2377-2386.

Akkin, T., D. P. Dave, et al. (2003). "Surface analysis using phase sensitive optical low coherence reflectometry." *Lasers in Surgery and Medicine*, 4-4.

Akkin, T., D. P. Dave, et al. (2003). "Imaging tissue response to electrical and photothermal stimulation with nanometer sensitivity." *Lasers in Surgery and Medicine* 33(4): 219-225.

Akkin, T., T. E. Milner, et al. (2002). "Phase-sensitive measurement of birefringence change as an indication of neural functionality and diseases." *Lasers in Surgery and Medicine*: 6-6.

Andretzky, P., Lindner, M.W., Herrmann, J.M., Schultz, A., Konzog, M., Kiesewetter, F., Haeusler, G. (1999). "Optical coherence tomography by 'spectral radar': Dynamic range estimation and in vivo measurements of skin." *Proceedings of SPIE—The International Society for Optical Engineering* 3567: pp. 78-87.

Antcliff, R. J., T. J. ffytche, et al. (2000). "Optical coherence tomography of melanocytoma." *American Journal of Ophthalmology* 130(6): 845-7.

Antcliff, R. J., M. R. Stanford, et al. (2000). "Comparison between optical coherence tomography and fundus fluorescein angiography for the detection of cystoid macular edema in patients with uveitis." *Ophthalmology* 107(3): 593-9.

Anvari, B., T. E. Milner, et al. (1995). "Selective Cooling of Biological Tissues—Application for Thermally Mediated Therapeutic Procedures." *Physics in Medicine and Biology* 40(2): 241-252.

Anvari, B., B. S. Tanenbaum, et al. (1995). "A Theoretical-Study of the Thermal Response of Skin to Cryogen Spray Cooling and Pulsed-Laser Irradiation—Implications for Treatmetn of Port-Wine Stain Birthmarks." *Physics in Medicine and Biology* 40(9): 1451-1465.

Arend, O., M. Ruffer, et al. (2000). "Macular circulation in patients with diabetes mellitus with and without arterial hypertension." *British Journal of Ophthalmology* 84(12): 1392-1396.

Arimoto, H. and Y. Ohtsuka (1997). "Measurements of the complex degree of spectral coherence by use of a wave-front-folded interferometer." *Optics Letters* 22(13): 958-960.

Azzolini, C., F. Patelli, et al. (2001). "Correlation between optical coherence tomography data and biomicroscopic interpretation of idiopathic macular hole." *American Journal of Ophthalmology* 132(3): 348-55.

Baba, T., K. Ohno-Matsui, et al. (2002). "Optical coherence tomography of choroidal neovascularization in high myopia." *Acta Ophthalmoloqica Scandinavica* 80(1): 82-7.

Bail, M. A. H., Gerd; Herrmann, Juergen M.; Lindner, Michael W.; Ringler, R. (1996). "Optical coherence tomography with the "spectral radar": fast optical analysis in volume scatterers by short-coherence interferometry." *Proc. SPIE*, 2925: p. 298-303.

Baney, D. M. and W. V. Sorin (1993)."Extended-Range Optical Low-Coherence Reflectometry Using a Recirculating Delay Technique." *Ieee Photonics Technology Letters* 5(9): 1109-1112.

Baney, D. M., B. Szafraniec, et al. (2002). "Coherent optical spectrum analyzer." *Ieee Photonics Technology Letters* 14(3): 355-357.

Barakat, R. (1981). "Bilinear Constraints between Elements of the 4by4 Mueller-Jones Transfer-Matrix of Polarization Theory." *Optics Communications* 38(3): 159-161.

Barakat, R. (1993). "Analytic Proofs of the Arago-Fresnel Laws for the Interference of Polarized-Light." *Journal of the Optical Society of America a-Optics Image Science and Vision* 10(1): 180-185.

Barbastathis, G. and D. J. Brady (1999). "Multidimensional tomographic imaging using volume holography." *Proceedings of the Ieee* 87(12):2098-2120.

Bardal, S., A. Kamal, et al. (1992). "Photoinduced Birefringence in Optical Fibers—a Comparative-Study of Low-Birefringence and High-Birefringence Fibers." *Optics Letters* 17(6): 411-413.

Barsky, S. H., S. Rosen, et al. (1980). "Nature and Evolution of Port Wine Stains—Computer-Assisted Study." *Journal of Investigative Dermatology* 74(3): 154-157.

Barton, J. K., J. A. Izatt, et al. (1999). "Three-dimensional reconstruction of blood vessels from in vivo color Doppler optical coherence tomography images." *Dermatology* 198(4): 355-361.

Barton, J. K., A. Rollins, et al. (2001). "Photothermal coagulation of blood vessels: a comparison of high-speed optical coherence tomography and numerical modelling." *Physics in Medicine and Biology* 46.

Barton, J. K., A. J. Welch, et al. (1998). "Investigating pulsed dye laser-blood vessel interaction with color Doppler optical coherence tomography." *Optics Express* 3.

Bashkansky, M., M. D. Duncan, et al. "Subsurface defect detection in ceramics by high-speed high-resolution optical coherent tomography." *Optics Letters* 22 (1):61-63.

Bashkansky, M. and J. Reintjes (2000). tomography."Statistics and reduction of speckle in optical coherence tomography." *Optics Letters* 25(8): 545-547.

Baumgartner, A., S. Dichtl, et al. (2000). "Polarization-sensitive optical coherence tomography of dental Structures." *Caries Research* 34(1): 59-69.

Baumgartner, A., C. K. Hitzenberger, et al. (2000). "Resolution-improved dual-beam and standard optical coherence tomography: a comparison." *Graefes Archive for Clincial and Experimental Ophthalmology* 238(5): 385-392.

Baumgartner, A., C. K. Hitzenberger, et al. (1998). "Signal and resolution enhancements in dual beam optical coherence tomography of the human eye." *Journal of Biomedical Optics* 3(1): 45-54.

Beaurepaire, E., P. Gleyzes, et at. (1998). *Optical coherence microscopy for the in-depth study of biological structures: System based on a parallel detection scheme*, Proceedings of SPIE—The International Society for Optical Engineering.

Beaurepaire, E., L. Moreaux, et al. (1999). "Combined scanning optical coherence and two-photon-excited fluorescence microscopy." *Optics Letters* 24(14): 969-971.

Bechara, F. G., T. Gambichler, et al. (2004). "Histomorphologic correlation with routine histology and optical coherence tomography." *Skin Research and Technology* 10 (3): 169-173.

Bechmann, M., M. J. Thiel, et al. (2000). "Central corneal thickness determined with optical coherence tomography in various types of glaucoma. [see comments]." *British Journal of Ophthalmology* 84(11): 1233-7.

Bek, T. and M. Kandi (2000). "Quantitative anomaloscopy and optical coherence tomography scanning in central serous chorioretinopathy." *Acta Ophthalmologica Scandinavica* 78(6): 632-7.

Benoit, A. M., K. Naoun, et al. (2001). "Linear dichroism of the retinal nerve fiber layer expressed with Mueller matrices." *Applied Optics* 40(4): 565-569.

Bicout, D., C. Brosseau, et al. (1994). "Depolarization of Multiply Scattered Waves by Spherical Diffusers—Influence of the Size Parameter." *Physical Review* E 49(2): 1767-1770.

Blanchot, L., M. Lebec, et al. (1997). *Low-coherence in depth microscopy for biological tissues imaging: Design of a real time control system*. Proceedings of SPIE—The International Society for Optical Engineering.

Blumenthal, E. Z. and R. N. Weinreb (2001). "Assessment of the retinal nerve fiber layer in clinical trials of glaucoma neuroprotection. [Review] [36 refs]." *Survey of Ophthalmology* 45(Suppl 3): S305-12; discussion S332-4.

Blumenthal, E. Z., J. M. Williams, et al. "Reproducibility of nerve fiber layer thickness measurements by use of optical coherence tomography." *Ophthalmology* 107(12): 2278-82.

Boppart, S. A., B. E. Bouma, et al. (1996). "Imaging developing neural morphology using optical coherence tomography." *Journal of Neuroscience Methods* 70.

Boppart, S. A., B. E. Bouma, et al. (1997). "Forward-imaging instruments for optical coherence tomography." *Optics Letters* 22.

Boppart, S. A., B. E. Bouma, et al. (1998). "Intraoperative assessment of microsurgery with three-dimensional optical coherence tomography." *Radiology* 208: 81-86.

Boppart, S. A., J. Herrmann, et al. (1999). "High-resolution optical coherence tomography-guided laser ablation of surgical tissue." *Journal of Surgical Research* 82(2): 275-84.

Bouma, B. E. and J. G. Fujimoto (1996). "Compact Kerr-lens mode-locked resonators." *Optics Letters* 21. 134-136.

Bouma, B. E., L. E. Nelson, et al. (1998). "Optical coherence tomographic imaging of human tissue at 1.55 mu m and 1.81 mu m using Er and Tm-doped fiber sources." *Journal of Biomedical Optics* 3. 76-79.

Bouma, B. E., M. Ramaswamy-Paye, et al. (1997). "Compact resonator designs for mode-locked solid-state lasers." *Applied Physics B (Lasers and Optics)* B65. 213-220.

Bouma, B. E. and G. J. Tearney (2002). "Clinical imaging with optical coherence tomography." *Academic Radiology* 9(8): 942-953.

Bouma, B. E., G. J. Tearney, et al. (1996). "Self-phase-modulated Kerr-lens mode-locked Cr:forsterite laser source for optical coherence tomography." *Optics Letters* 21(22): 1839.

Bouma, B. E., G. J. Tearney, et al. (2000). "High-resolution imaging of the human esophagus and stomach in vivo using optical coherence tomography." *Gastrointestinal Endoscopy* 51(4): 467-474.

Bouma, B. E., G. J. Tearney, et al. (2003). "Evaluation of intracoronary stenting by intravascular optical coherence tomography." *Heart* 89(3): 317-320.

Bourquin, S., V. Monterosso, et al. (2000). "Video-rate optical low-coherence reflectometry based on a linear smart detector array." *Optics Letters* 25(2): 102-104.

Bourquin, S., P. Seitz, et al. (2001). "Optical coherence topography based on a two-dimensional smart detector array." *Optics Letters* 26(8): 512-514.

Bouzid, A., M. A. G. Abushagur, et al. (1995). "Fiber-optic four-detector polarimeter." *Optics Communications* 118(3-4): 329-334.

Bowd, C., R. N. Weinreb, et al. (2000). "The retinal nerve fiber layer thickness in ocular hypertensive, normal, and glaucomatous eyes with optical coherence tomography." *Archives of Ophthalmology* 118(1): 22-6.

Bowd, C., L. M. Zangwill, et al. (2001) "Detecting early glaucoma by assessment of retinal nerve fiber layer thickness and visual function." *Investigative Ophthalmology & Visual Science* 42(9): 1993-2003.

Bowd, C., L. M. Zangwill, et al. (2002). "Imaging of the optic disc and retinal nerve fiber layer: the effects of age, optic disc area, refractive error, and gender." *Journal of the Optical Society of America, A, Optics, Image Science, & Vision* 19(1): 197-207.

Brand, S., J. M. Poneros, et al. (2000). "Optical coherence tomography in the gastrointestinal tract." *Endoscopy* 32(10): 796-803.

Brezinski, M. E. and J. G. Fujimoto (1999). "Optical coherence tomography: high-resolution imaging in nontransparent tissue." *IEEE Journal of Selected Topics in Quantum Electronics* 5(4): 1185-1192.

Brezinski, M. E., G. J. Tearney, et al. (1996). "Imaging of coronary artery microstruture (in vitro) with optical coherence tomography." *American Journal of Cardiology* 77 (1): 92-93.

Brezinski, M. E., G. J. Tearney, et al. (1996). "Optical coherence tomography for optical biopsy—Properties and demonstration of vascular pathology." *Circulation* 93(6): 1206-1213.

Brezinski, M. E., G. J. Tearney, et al. (1997). "Assessing atherosclerotic plaque morphology: Comparison of optical coherence tomography and high frequency intravascular ultrasound." *Heart* 77(5): 397-403.

Brink, H. B. K. and G. J. Vanblokland (1988). "Birefringence of the Human Foveal Area Assessed Invivo with Mueller-Matrix Ellipsometry." *Journal of the Optical Society of America a-Optics Image Science and Vision* 5(1): 49-57.

Brosseau, C. and D. Bicout (1994). "Entropy Production in Multiple-Scattering of Light by a Spatially Random Medium." *Physical Review* E 50(6): 4997-5005.

Burgoyne, C. F., D. E. Mercante, et al. (2002). "Change detection in regional and volumetric disc parameters using longitudinal confocal scanning laser tomography." *Ophthalmology* 109(3): 455-66.

Candido, R. and T. J. Allen (2002). "Haemodynamics in microvascular complications in type 1 diabetes." *Diabetes-Metabolism Research and Reviews* 18(4): 286-304.

Cense, B., T. C. Chen, et al. (2004). "Thickness and birefringence of healthy retinal nerve fiber layer tissue measured with polarization-sensitive optical coherence tomography." *Investigative Ophthalmology & Visual Science* 45(8): 2606-2612.

Cense, B., N. Nassif, et al. (2004). "Ultrahigh-Resolution High-Speed Retinal Imaging Using Spectral-Domain Optical Coherence Tomography." *Optics Express* 12(11): 2435-2447.

Chance, B., J. S. Leigh, et al. (1988). "Comparison of Time-Resolved and Time-Unresolved Measurements of Deoxyhemoglobin in Brain." *Proceedings of the National Academy of Sciences of the United States of America* 85(14): 4971-4975.

Chang, E. P., D. A. Keedy, et al. (1974). "Ultrastructures of Rabbit Corneal Stroma—Mapping of Optical and Morphological Anisotropies." *Biochimica Et Biophysica Acta* 343(3): 615-626.

Chartier, T., A. Hideur, et al. (2001). "Measurement of the elliptical birefringence of single-mode optical fibers." *Applied Optics* 40(30): 5343-5353.

Chauhan, B. C., J. W. Blanchard, et al. "Technique for Detecting Serial Topographic Changes in the Optic Disc and Peripapilary Retina Using Scanning Laser Tomograph." *Invest Ophthalmol Vis Sci* 41: 775-782.

Chen, Z. P., T. E. Milner, et al. (1997). "Optical Doppler tomographic imaging of fluid flow velocity in highly scattering media." *Optics Letters* 22(1): 64-66.

Chen, Z. P., T. E. Milner, et al. (1997). "Noninvasive imaging of in vivo blood flow velocity using optical Doppler tomography." *Optics Letters* 22(14): 1119-1121.

Chen, Z. P., Y. H. Zhao, et al. (1999). "Optical Doppler tomography." *Ieee Journal of Selected Topics in Quantum Electronics* 5(4): 1134-1142.

Cheong, W. F., S. A. Prahl, et al. (1990). "A Review of the Optical-Properties of Biological Tissues." *Ieee Journal of Quantum Electronics* 26(12): 2166-2185.

Chernikov, S. V., Y. Zhu, et al. (1997). "Supercontinuum self-Q-switched ytterbium fiber laser." *Optics Letters* 22(5): 298-300.

Cho, S. H., B. E. Bouma, et al. (1999). "Low-repetition-rate high-peak-power Kerr-lens mode-locked Ti:Al/sub 2/0/sub 3/ laser with a multiple-pass cavity." *Optics Letters* 24(6): 417-419.

Choma, M. A., M. V. Sarunic, et al. (2003). "Sensitivity advantage of swept source and Fourier domain optical coherence tomography." *Optics Express* 11(18): 2183-2189.

Choma, M. A., C. H. Yang, et al. (2003). "Instantaneous quadrature low-coherence interferometry with 3 × 3 fiber-optic couplers." *Optics Letters* 28(22): 2162-2164.

Choplin, N. T. and D. C. Lundy (2001). "The sensitivity and specificity of scanning laser polarimetry in the detection of glaucoma in a clinical setting." *Ophthalmology* 108 (5): 899-904.

Christens Barry, W. A., W. J. Green, et al. (1996). "Spatial mapping of polarized light transmission in the central rabbit cornea." *Experimental Eye Research* 62(6): 651-662.

Chvapil, M., D. P. Speer, et al. (1984). "Identification of the depth of burn injury by collagen stainability." *Plastic & Reconstructive Surgery* 73(3): 438-41.

Cioffi, G. A. (2001). "Three common assumptions about ocular blood flow and glaucoma." *Survey of Ophthalmology* 45: S325-S331.

Coleman, A. L. (1999). "Glaucoma." *Lancet* 354(9192): 1803-10.

Collaborative Normal-Tension Glaucoma Study Group (1998). "Comparison of Glaucomatous Progression Between Untreated Patients With Normal Tension Glaucoma and Patients with Therapeutically Reduced Intraocular Pressures." *Am J Ophthalmol* 126: 487-97.

Collaborative Normal-Tension Glaucoma Study Group (1998). "The effectiveness of intraocular pressure reduction in the treatment of normal-tension glaucoma." *Am J Ophthalmol* 126: 498-505.

Collaborative Normal-Tension Glaucoma Study Group (2001). "Natural History of Normal-Tension Glaucoma." *Ophthalmology* 108: 247-253.

Colston, B. W., M. J. Everett, et al. (1998). "Imaging of hard- and soft-tissue structure in the oral cavity by optical coherence tomography." *Applied Optics* 37(16): 3582-3585.

Colston, B. W., U. S. Sathyam, et al. (1998). "Dental OCT." *Optics Express* 3(6): 230-238.

Congdon, N. G., D. S. Friedman, et al. (2003). "Important causes of visual impairment in the world today." *Jama—Journal of the American Medical Association* 290(15): 2057-2060.

Cregan, R. F., B. J. Mangan, et al. (1999). "Single-mode photonic band gap guidance of light in air." *Science* 285(5433): 1537-1539.

DalMolin, M., A. Galtarossa, et al. (1997). "Experimental investigation of linear polarization in high-birefringence single-mode fibers." *Applied Optics* 36(12): 2526-2528.

Danielson, B. L. and C. D. Whittenberg Resolution. "Guided-Wave Reflectometry with Micrometer Resolution." *Applied Optics* 26(14): 2836-2842.

Dave, D. P. and T. E. Milner (2000). "Doppler-angle measurement in highly scattering media." *Optics Letters* 25(20): 1523-1525.

de Boer, J. F., T. E. Milner, et al. (1998). *Two dimensional birefringence imaging in biological tissue using phase and polarization sensitive optical coherence tomography*. Trends in Optics and Photonics (TOPS): Advances in Optical Imaging and Photon Migration, Orlando, USA, Optical Society of America, Washington, DC 1998.

de Boer, J. F., C. E. Saxer, et al. (2001). "Stable carrier generation and phase-resolved digital data processing in optical coherence tomography." *Applied Optics* 40(31): 5787-5790.

Degroot, P. and L. Deck (1993). "3-Dimensional Imaging by Sub-Nyquist Sampling of White-Light Interferograms." *Optics Letters* 18(17): 1462-1464.

Denk, W., J. H. Strickler, et al. (1990). "2-Photon Laser Scanning Fluorescence Microscopy." *Science* 248(4951): 73-76.

Descour, M. R., A. H. O. Karkkainen, et al. (2002). "Toward the development of miniaturized Imaging systems for detection of pre-cancer." *Ieee Journal of Quantum Electronics* 38(2): 122-130.

Dettwiller, L. (1997). "Polarization state interference: A general investigation." *Pure and Applied Optics* 6(1): 41-53.

DiCarlo, C. D., W. P. Roach, et al. (1999). "Comparison of optical coherence tomography imaging of cataracts with histopathology." *Journal of Biomedical Optics* 4.

Ding, Z., Y. Zhao, et al. (2002). "Real-time phase-resolved optical coherence tomography and optical Doppler tomography and optical Doppler tomography." *Optics Express* 10(5): 236-245.

Dobrin, P. B. (1996). "Effect of histologic preparation on the cross-sectional area of arterial rings." *Journal of Surgical Research* 61(2): 413-5.

Donohue, D. J., B. J. Stoyanov, et al. (1995). "Numerical Modeling of the Corneas Lamellar Structure and Birefringence Properties." *Journal of the Optical Society of America a-Optics Image Science and Vision* 12(7): 1425-1438.

Doornbos, R. M. P., R. Lang, et al. (1999). "The determination of in vivo human tissue optical properties and absolute chromophore concentrations using spatially resolved steady-state diffuse reflectance spectroscopy." *Physics in Medicine and Biology* 44(4): 967-981.

Drexler, W., A. Baumgartner, et al. (1997). "Biometric investigation of changes in the anterior eye segment during accommodation." *Vision Research* 37(19): 2789-2800.

Drexler, W., A. Baumgartner, et al. (1997). "Submicrometer precision biometry of the anterior segment of the human eye." *Investigative Ophthalmology & Visual Science* 38(7): 1304-1313.

Drexler, W., A. Baumgartner, et al. (1998). "Dual beam optical coherence tomography: signal identification for ophthalmologic diagnosis." *Journal of Biomedical Optics* 3 (1): 55-65.

Drexler, W., O. Findl, et al. (1998). "Partial coherence interferometry: A novel approach to biometry in cataract surgery." *American Journal of Ophthalmology* 126(4): 524-534.

Drexler, W., O. Findl, et al. (1997). "Clinical feasibility of dual beam optical coherence topography and tomography for ophthalmologic diagnosis." *Investigative Ophthalmology & Visual Science* 38(4): 1038-1038.

Drexler, W., C. K. Hitzenberger, et al. "Investigation of dispersion effects in ocular media by multiple wavelength partial coherence interferometry." *Experimental Eye Research* 66(1): 25-33.

Drexler, W., C. K. Hitzenberger, et al. (1996). "(Sub)micrometer precision biometry of the human eye by optical coherence tomography and topography." *Investigative Ophthalmology & Visual Science* 37(3): 4374-4374.

Drexler, W., C. K. Hitzenberger, et al. (1995). "Measurement of the Thickness of Fundus Layers by Partial Coherence Tomography." *Optical Engineering* 34(3): 701-710.

Drexler, W., U. Morgner, et al. (2001). "Ultrahigh-resolution ophthalmic optical coherence tomography." *Nature Medicine* 7(4): 502-507.

Drexler, W., U. Morgner, et al. (2001). "Ultrahigh-resolution ophthalmic optical coherence tomography. [erratum appears in Nat Med May 2001;7(5):636.]." *Nature Medicine* 7(4): 502-7

Drexler, W., H. Sattmann, et al. (2003). "Enhanced visualization of macular pathology with the use of ultrahigh-resolution optical coherence tomography." *Archives of Ophthalmology* 121(5): 695-706.

Drexler, W., D. Stamper, et al. (2001). "Correlation of collagen organization with polarization sensitive imaging of in vitro cartilage: implications for osteoarthritis." *Journal of Rheumatology* 28(6): 1311-8.

Droog, E. J., W. Steenbergen, et al. (2001). "Measurement of depth of burns by laser Doppler perfusion imaging." *Burns* 27(6): 561-8.

Dubois, A., K. Grieve, et al. (2004). "Ultrahigh-resolution full-field optical coherence tomography." *Applied Optics* 43(14): 2874-2883.

Dubois, A., L. Vabre, et al. (2002). "High-resolution full-field optical coherence tomography with a Linnik microscope." *Applied Optics* 41(4): 805-812.

Ducros, M., M. Laubscher, et al. (2002). "Parallel optical coherence tomography in scattering samples using a two-dimensional smart-pixel detector array." *Optics Communications* 202(1-3): 29-35.

Ducros, M. G., J. D. Marsack, et al. (2001). "Primate retina imaging with polarization-sensitive optical coherence tomography." *Journal of the Optical Society of America a-Optics Image Science and Vision* 18(12): 2945-2956.

Duncan, A., J. H. Meek, et al. (1995). "Optical Pathlength Measurements on Adult Head, Calf and Forearm and the Head of the Newborn-Infant Using Phase-Resolved Optical Spectroscopy." *Physics in Medicine and Biology* 40(2): 295-304.

Eigensee, A., G. Haeusler, et al. (1996). "New method of short-coherence interferometry in human skin (in vivo) and in solid volume scatterers." *Proceedings of SPIE—The International Society for Optical Engineering* 2925: 169-178.

Eisenbeiss, W., J. Marotz, et al. (1999). "Reflection-optical multispectral imaging method for objective determination of burn depth." *Burns* 25(8): 697-704.

Elbaum, M., M. King, et al. (1972). "Wavelength-Diversity Technique for Reduction of Speckle Size." *Journal of the Optical Society of America* 62(5): 732-&.

Ervin, J. C., H. G. Lemij, et al. (2002). "Clinician change detection viewing longitudinal stereophotographs compared to confocal scanning laser tomography in the LSU Experimental Glaucoma (LEG) Study." *Ophthalmology* 109(3): 467-81.

Essenpreis, M., C. E. Elwell, et al. (1993). "Spectral Dependence of Temporal Point Spread Functions in Human Tissues." *Applied Optics* 32(4): 418-425.

Eun, H. C. (1995). "Evaluation of skin blood flow by laser Doppler flowmetry. [Review] [151 refs]." *Clincis in Dermatology* 13(4): 337-47.

Evans, J. A., J. M. Poneros, et al. (2004). "Application of a histopathologic scoring system to optical coherence tomography (OCT) images to identify high-grade dysplasia in Barrett's esophagus." *Gastroenterology* 126(4): A51-A51.

Feldchtein, F. I., G. V. Gelikonov, et al. (1998). "In vivo OCT imaging of hard and soft tissue of the oral cavity." *Optics Express* 3(6): 239-250.

Feldchtein, F. I., G. V. Gelikonov, et al. (1998). "Endoscopic applications of optical coherence tomography." *Optics Express* 3(6): 257-270.

Fercher, A. F., W. Drexler, et al. (1997). "Optical ocular tomography." *Neuro-Ophthalmology* 18(2): 39-49.

Fercher, A. F., W. Drexler, et al. (1994). *Measurement of optical distances by optical spectrum modulation*. Proceedings of SPIE—The International Society for Optical Engineering.

Fercher, A. F., W. Drexler, et al. (2003). "Optical coherence tomography—principles and applications." *Reports on Progress in Physics* 66(2): 239-303.

Fercher, A. F., C. Hitzenberger, et al. (1991). "Measurement of Intraocular Optical Distances Using Partially Coherent Laser-Light." *Journal of Modern Optics* 38(7): 1327-1333.

Fercher, A. F., C. K. Hitzenberger, et al. (1996). *Ocular partial coherence interferometry*. Proceedings of SPIE—The International Society for Optical Engineering.

Fercher, A. F., C. K. Hitzenberger, et al. (1993). "In-Vivo Optical Coherence Tomography." *American Journal of Ophthalmology* 116(1): 113-115.

Fercher, A. F., C. K. Hitzenberger, et al. (1994). *In-vivo dual-beam optical coherence tomography*. Proceedings of SPIE—The International Society for Optical Engineering.

Fercher, A. F., C. K. Hitzenberger, et al. (1995). "Measurement of Intraocular Distances by Backscattering Spectral Interferometry." *Optics Communications* 117(1-2): 43-48.

Fercher, A. F., C. K. Hitzenberger, et al. (2000). "A thermal light source technique for optical coherence tomography." *Optics Communications* 185(1-3): 57-64.

Fercher, A. F., C. K. Hitzenberger, et al. "Numerical dispersion compensation for Partial Coherence Interferometry and Optical Coherence Tomography." *Optics Express* 9(12): 610-615.

Fercher, A. F., C. K. Hitzenberger, et al. (2002). "Dispersion compensation for optical coherence tomography depth-scan signals by a numerical technique." *Optics Communications* 204(1-6): 67-74.

Fercher, A. F., H. C. Li, et al. (1993). "Slit Lamp Laser-Doppler Interferometer." *Lasers in Surgery and Medicine* 13(4): 447-452.

Fercher, A. F., K. Mengedoht, et at. (1988). "Eye-Length Measurement by Interferometry with Partially Coherent-Light." *Optics Letters* 13(3): 186-188.

Ferro, P., M. Haelterman, et al. (1991). "All-Optical Polarization Switch with Long Low-Birefringence Fiber." *Electronics Letters* 27(16): 1407-1408.

Fetterman, M. R., D. Goswami, et al. (1998). "Ultrafast pulse shaping: amplification and characterization." *Optics Express* 3(10): 366-375.

Findl, O., W. Drexler, et al. (2001). "Improved prediction of intraocular lens power using partial coherence interferometry." *Journal of Cataract and Refractive Surgery* 27 (6): 861-867.

Fork, R. L., C. H. B. Cruz, et al. (1987). "Compression of Optical Pulses to 6 Femtoseconds by Using Cubic Phase Compensation." *Optics Letters* 12(7): 483-485.

Foschini, G. J. and C. D. Poole (1991). "Statistical-Theory of Polarization Dispersion in Single-Mode Fibers." *Journal of Lightwave Technology* 9(11): 1439-1456.

Francia, C., F. Bruyere, et al. (1998). "PMD second-order effects on pulse propagation in single-mode optical fibers." *Ieee Photonics Technology Letters* 10(12): 1739-1741.

Fried, D., R. E. Glena, et al. (1995). "Nature of Light-Scattering in Dental Enamel and Dentin at Visible and near-Infrared Wavelengths." *Applied Optics* 34(7): 1278-1285.

Fujimoto, J. G., M. E. Brezinski, et al. (1995). "Optical Biopsy and Imaging Using Optical Coherence Tomography." *Nature Medicine* 1(9): 970-972.

Fukasawa, A. and H. Iijima (2002). "Optical coherence tomography of choroidal osteoma." *American Journal of Ophthalmology* 133(3): 419-21.

Fymat, A. L. (1981). "High-Resolution Interferometric Spectrophotopolarimetry." *Optical Engineering* 20(1): 25-30.

Galtarossa, A., L. Palmieri, et al. (2000). "Statistical characterization of fiber random birefringence." *Optics Letters* 25(18): 1322-1324.

Galtarossa, A., L. Palmieri, et al. (2000). "Measurements of beat length and perturbation length in long single-mode fibers." *Optics Letters* 25(6): 384-386.

Gandjbakhche, A. H., P. Mills, et al. (1994). "Light-Scattering Technique for the Study of Orientation and Deformation of Red-Blood-Cells in a Concentrated Suspension." *Applied Optics* 33(6): 1070-1078.

Garcia, N. and M. Nieto-Vesperinas (2002). "Left-handed materials do not make a perfect lens." *Physical Review Letters* 88(20).

Gelikonov, V. M., G. V. Gelikonov, et al. (1995). "Coherent Optical Tomography of Microscopic Inhomogeneities in Biological Tissues." *Jetp Letters* 61(2): 158-162.

George, N. and A. Jain (1973). "Speckle Reduction Using Multiple Tones of Illumination." *Applied Optics* 12(6): 1202-1212.

Gibson, G. N., R. Klank, et al. (1996). "Electro-optically cavity-dumped ultrashort-pulse Ti:sapphire oscillator." *Optics Letters* 21(14): 1055.

Gil, J. J. (2000). "Characteristic properties of Mueller matrices." *Journal of the Optical Society of America a-Optics Image Science and Vision* 17(2): 328-334.

Gil, J. J. and E. Bernabeu (1987). "Obtainment of the Polarizing and Retardation Parameters of a Nondepolarizing Optical-System from the Polar Decomposition of Its Mueller Matrix." *Optik* 76(2): 67-71.

Gladkova, N. D., G. A. Petrova, et al. (2000). "In vivo optical coherence tomography imaging of human skin: norm and pathology." *Skin Research and Technology* 6 (1): 6-16.

Glaessl, A., A. G. Schreyer, et al. (2001). "Laser surgical planning with magnetic resonance imaging-based 3-dimensional reconstructions for intralesional Nd:YAG laser therapy of a venous malformation of the neck." *Archives of Dermatology* 137(10): 1331-1335.

Gloesmann, M., B. Hermann, et al. (2003). "Histologic correlation of pig retina radial stratification with ultrahigh-resolution optical coherence tomography." *Investigative Ophthalmology & Visual Science* 44(4): 1696-1703.

Goldberg, L. and D. Mehuys (1994). "High-Power Superluminescent Diode Source." *Electronics Letters* 30(20): 1682-1684.

Goldsmith, J. A., Y. Li, et al. (2005). "Anterior chamber width measurement by high speed optical coherence tomography." *Ophthalmology* 112(2): 238-244.

Goldstein, L. E., J. A. Muffat, et al. (2003). "Cytosolic beta-amyloid deposition and supranuclear cataracts in lenses from people with Alzheimer's disease." *Lancet* 361(9365): 1258-1265.

Golubovic, B., B. E. Bouma, et al. (1996). "Thin crystal, room-temperature Cr/sup 4 +/:forstefite laser using near-infrared pumping." *Optics Letters* 21(24): 1993-1995.

Gonzalez, S. and Z. Tannous (2002). "Real-time, in vivo confocal reflectance microscopy of basal cell carcinoma." *Journal of the American Academy of Dermatology* 47(6): 869-874.

Gordon, M. O. and M. A. Kass (1999). "The Ocular Hypertension Treatment Study: design and baseline description of the participants." *Archives of Ophthalmology* 117(5): 573-83.

Grayson, T. P., J. R. Torgerson, et al. (1994). "Observation of a Nonlocal Pancharatnam Phase-Shift in the Process of Induced Coherence without Induced Emission." *Physical Review* A 49(1): 626-628.

Greaney, M. J., D. C. Hoffman, et al. (2002). "Comparison of optic nerve imaging methods to distinguish nomral eyes from those with glaucoma." *Investigative Ophthalmology & Visual Science* 43(1): 140-5.

Greenfield, D. S., H. Bagga, et al. (2003). "Macular thickness changes in glaucomatous optic neuropathy detected using optical coherence tomography." *Archives of Ophthalmology* 121(1): 41-46.

Greenfield, D. S., R. W. Knighton, et al. "Effect of corneal polarization axis on assessment of retinal nerve fiber layer thickness by scanning laser polarimetry." *American Journal of Ophthalmology* 129(6): 715-722.

Griffin, R. A., D. D. Sampson, et al. (1995). "Coherence Coding for Photonic Code-Division Multiple-Access Networks." *Journal of Lightwave Technology* 13(9): 1826-1837.

Guedes, V., J. S. Schuman, et al. (2003). "Optical coherence tomography measurement of macular and nerve fiber layer thickness in normal and glaucomatous human eyes." *Ophthalmology* 110(1): 177-189.

Gueugniaud, P. Y., H. Carsin, et al. (2000). "Current advances in the initial management of major thermal burns. [Review] [76 refs]." *Intensive Care Medicine* 26(7): 848-56.

Guido, S. and R. T. Tranquillo (1993). "A Methodology for the Systematic and Quantitative Study of Cell Contact Guidance in Oriented Collagen Gels—Correlation of Fibroblast Orientation and Gel Birefringence." *Journal of Cell Science* 105: 317-331.

Gurses-Ozden, R., H. Ishikawa, et al. (1999). "Increasing sampling density improves reproducibility of optical coherence tomography measurements." *Journal of Glaucoma* 8(4): 238-41.

Guzzi, R. (1998). "Scattering Theory from Homogeneous and Coated Spheres." 1-11.

Haberland, U. B., Vladimir; Schmitt, Hans J. (1996). "Optical coherent tomography of scattering media using electrically tunable near-infrared semiconductor laser." *Applied Optics*.

Haberland, U. R., Walter; Blazek, Vladimir; Schmitt, Hans J. (1995). "Investigation of highly scattering media using near-infrared continuous wave tunable semiconductor laser." *Proc. SPIE*, 2389: 503-512.

Hale, G. M. and M. R. Querry (1973). "Optical-Constants of Water in 200-Nm to 200-Mum Wavelength Region." *Applied Optics* 12(3): 555-563.

Hammer, D. X., R. D. Ferguson, et al. ophthalmoscopy."Image stabilization for scanning laser ophthalmoscopy." *Optics Express* 10(26): 1542.

Hara, T., Y. Ooi, et al. (1989). "Transfer Characteristics of the Microchannel Spatial Light-Modulator." *Applied Optics* 28(22): 4781-4786.

Harland, C. C., S. G. Kale, et al. (2000). "Differentiation of common benign pigmented skin lesions from melanoma by high-resolution ultrasound." *British Journal of Dermatology* 143(2): 281-289.

Hartl, I., X. D. Li, et al. (2001). "Ultrahigh-resolution optical coherence tomography using continuum generation in an air-silica microstructure optical fiber." *Optics Letters* 26(9): 608-610.

Hassenstein, A., A. A. Bialasiewicz, et al. (2000). "Optical coherence tomography in uveitis patients." *American Journal of Ophthalmology* 130(5): 669-70.

Hattenhauer, M. G., D. H. Johnson, et al. (1998). "The probability of blindness from open-angle glaucoma. [see comments]." *Ophthalmology* 105(11): 2099-104.

Hausler, G., J. M. Herrmann, et al. (1996). "Observation of light propagation in volume scatterers with 10(11)-fold slow motion." *Optics Letters* 21(14): 1087-1089.

Hazebroek, H. F. and A. A. Holscher (1973). "Interferometric Ellipsometry." *Journal of Physics E-Scientific Instruments* 6(9): 822-826.

Hazebroek, H. F. and W. M. Visser (1983). "Automated Laser Interferometric Ellipsometry and Precision Reflectometry." *Journal of Physics E-Scientific Instruments* 16(7): 654-661.

He, Z. Y., N. Mukohzaka, et al. (1997). "Selective image extraction by synthesis of the coherence function using two-dimensional optical lock-in amplifier with microchannel spatial light modulator." *Ieee Photonics Technology Letters* 9(4): 514-516.

Hee, M. R., J. A. Izatt, et al. (1993). "Femtosecond Transillumination Optical Coherence Tomography." *Optics Letters* 18(12): 950-952.

Hee, M. R., J. A. Izatt, et al. (1995). "Optical coherence tomography of the human retina." *Archives of Ophthalmology* 113(3): 325-32.

Hee, M. R., C. A. Puliafito, et al. (1998). "Topography of diabetic macular edema with optical coherence tomography." *Ophthalmology* 105(2): 360-70.

Hee, M. R., C. A. Puliafito, et al. (1995). "Quantitative assessment of macular edema with optical coherence tomography." *Archives of Ophthalmology* 113(8): 1019-29.

Hellmuth, T. and M. Welle (1998). "Simultaneous measurement of dispersion, spectrum, and distance with a fourier transform spectrometer." *Journal of Biomedical Optics* 3(1): 7-11.

Hemenger, R. P. (1989). "Birefringence of a medium of tenuous parallel cylinders." *Applied Optics* 28(18): 4030-4034.

Henry, M. (1981). "Fresnel-Arago Laws for Interference in Polarized-Light—Demonstration Experiment." *American Journal of Physics* 49(7): 690-691.

Herz, P. R., Y. Chen, et al. (2004). "Micromotor endoscope catheter for in vivo, ultrahigh-resolution optical coherence tomography." *Optics Letters* 29(19): 2261-2263.

Hirakawa, H., H. Iijima, et al. (1999). "Optical coherence tomography of cystoid macular edema associated with retinitis pigmentosa." *American Journal of Ophthalmology* 128(2): 185-91.

Hitzenberger, C. K., A. Baumgartner, et al. (1994). "Interferometric Measurement of Corneal Thickness with Micrometer Precision." *American Journal of Ophthalmology* 118(4): 468-476.

Hitzenberger, C. K., A. Baumgartner, et al. (1999). "Dispersion effects in partial coherence interferometry: Implications for intraocular ranging." *Journal of Biomedical Optics* 4(1): 144-151.

Hitzenberger, C. K., A. Baumgartner, et al. (1998). "Dispersion induced multiple signal peak splitting in partial coherence interferometry." *Optics Communications* 154 (4): 179-185.

Hitzenberger, C. K., M. Danner, et al. (1999). "Measurement of the spatial coherence of superluminescent diodes." *Journal of Modern Optics* 46(12): 1763-1774.

Hitzenberger, C. K. and A. F. Fercher (1999). "Differential phase contrast in optical coherence tomography." *Optics Letters* 24(9): 622-624.

Hitzenberger, C. K., M. Sticker, et al. (2001). "Differential phase measurements in low-coherence interferometry without 2 pi ambiguity." *Optics Letters* 26(23): 1864-1866.

Hoeling, B. M., A. D. Fernandez, et al. (2000). "An optical coherence microscope for 3-dimensional imaging in developmental biology." *Optics Express* 6(7): 136-146.

Hoerauf, H., C. Scholz, et al. (2002). "Transscleral optical coherence tomography: a new imaging method for the anterior segment of the eye." *Archives of Ophthalmology* 120(6): 816-9.

Hoffmann, K., M. Happe, et al. (1998). "Optical coherence tomography (OCT) in dermatology." *Journal of Investigative Dermatology* 110(4): 583-583.

Hoh, S. T., D. S. Greenfield, et al. (2000). "Optical coherence tomography and scanning laser polarimetry in normal, ocular hypertensive, and glaucomatous eyes." *American Journal of Ophthalmology* 129(2): 129-35.

Hohenleutner, U., M. Hilbert, et al. (1995). "Epidermal Damage and Limited Coagulation Depth with the Flashlamp-Pumped Pulsed Dye-Laser—a Histochemical-Study." *Journal of Investigative Dermatology* 104(5): 798-802.

Holland, A. J. A., H. C. O. Martin, et al. "Laser Doppler imaging prediction of burn wound outcome in children." *Burns* 28(1): 11-17.

Notate, K. and T. Okugawa (1994). "Optical Information-Processing by Synthesis of the Coherence Function." *Journal of Lightwave Technology* 12(7): 1247-1255.

Hourdakis, C. J. and A. Perris (1995). "A Monte-Carlo Estimation of Tissue Optical-Properties for Use in Laser Dosimetry." *Physics in Medicine and Biology* 40(3): 351-364.

Hu, Z., F. Li, et al. (2000). "Wavelength-tunable narrow-linewidth semiconductor fiber-ring laser." *IEEE Photonics Techology Letters* 12(8): 977-979.

Huang, F., W. Yang, et al. (2001). "Quadrature spectral interferometric detection and pulse shaping." *Optics Letters* 26(6): 382-384.

Huang, X. R. and R. W. Knighton (2002)."Linear birefringence of the retinal nerve fiber layer measured in vitro with a multispectral imaging micropolarimeter." *Journal of Biomedical Optics* 7(2): 199-204.

Huber, R., M. Wojtkowski, et al. (2005). "Amplified, frequency swept lasers for frequency domain reflectometry and OCT imaging: design and scaling principles." *Optics Express* 13(9): 3513-3528.

Hunter, D. G., J. C. Sandruck, et al. (1999). "Mathematical modeling of retinal birefringence scanning." *Journal of the Optical Society of America a-Optics Image Science and Vision* 16(9): 2103-2111.

Hurwitz, H. H. and R. C. Jones (1941). "A new calculus for the treatment of optical systems II. Proof of three general equivalence theorems." *Journal of the Optical Society of America* 31(7): 493-499.

Huttner, B., C. De Banos, et al. (1999). "Polarization-induced pulse spreading in birefringent optical fibers with zero differential group delay." *Optics Letters* 24(6): 370-372.

Huttner, B., B. Gisin, et al. (1999). "Distributed PMD measurement with a polarization-OTDR in optical fibers." *Journal of Lightwave Technology* 17(10): 1843-1848.

Huttner, B., J. Reecht, et al. (1998). "Local birefringence measurements in single-mode fibers with coherent optical frequency-domain reflectometry." *Ieee Photonics Technology Letters* 10(10): 1458-1460.

Hyde, S. C. W., N. P. Barry, et al. (1995). "Sub-100-Mu-M Depth-Resolved Holographic Imaging through Scattering Media in the near-Infrared." *Optics Letters* 20(22): 2330-2332.

Hyde, S. C. W., N. P. Barry, et al. (1995). "Depth-Resolved Holographic Imaging through Scattering Media by Photorefraction." *Optics Letters* 20(11): 1331-1333.

Iftimia, N. V., B. E. Bouma, et al. (2004). "Adaptive ranging for optical coherence tomography." *Optics Express* 12(17): 4025-4034.

Iida, T., N. Hagimura, et al. (2000). "Evaluation of central serous chorioretinopathy with optical coherence tomography." *American Journal of Ophthalmology* 129(1): 16-20.

Imai, M., H. Iijima, et al. (2001). "Optical coherence tomography of tractional macular elevations in eyes with proliferative diabetic retinopathy. [republished in Am J Ophthalmol. Sep. 2001;132(3):458-61 ; 11530091.]." *American Journal of Ophthalmology* 132(1): 81-4.

Indebetouw, G. and P. Klysubun (2000). "Imaging through scattering media with depth resolution by use of low-coherence gating in spatiotemporal digital holography." *Optics Letters* 25(4): 212-214.

Ip, M. S., B. J. Baker, et al. (2002). "Anatomical outcomes of surgery for idiopathic macular hole as determined by optical coherence tomography." *Archives of Ophthalmology* 120(1): 29-35.

Ismail, R., V. Tanner, et al. (2002). "Optical coherence tomography imaging of severe commotio retinae and associated macular hole." *British Journal of Ophthalmology* 86(4): 473-4.

Izatt, J. A., M. R. Hee, et al. (1994). "Optical Coherence Microscopy in Scattering Media." *Optics Letters* 19(8): 590-592.

Izatt, J. A., M. R. Hee, et al. (1994). "Micrometer-scale resolution imaging of the anterior eye in vivo with optical coherence tomography." *Archives of Ophthalmology* 112 (12): 1584-9.

Izatt, J. A., M. D. Kulkarni, et al. (1997). "In vivo bidirectional color Doppler flow imaging of picoliter blood volumes using optical coherence tomography." *Optics Letters* 22(18): 1439-1441.

Izatt, J. A., M. D. Kulkarni, et al. (1996). "Optical coherence tomography and microscopy in gastrointestinal tissues." *IEEE Journal of Selected Topics in Quantum Electronics* 2(4): 1017.

Jacques, S. L., J. S. Nelson, et al. (1993). "Pulsed Photothermal Radiometry of Port-Wine-Stain Lesions." *Applied Optics* 32(13): 2439-2446.

Jacques, S. L., J. R. Roman, et al. (2000). "Imaging superficial tissues with polarized light." *Lasers in Surgery and Medicine* 26(2): 119-129.

Jang, I. K., B. E. Bouma, et al. (2002). "Visualization of coronary atherosclerotic plaques in patients using optical coherence tomography: Comparison with intravascular ultrasound." *Journal of the American College of Cardiology* 39(4): 604-609.

Jang, I. K., B. D. MacNeill, et al. (2002). "In-vivo characterization of coronary plaques in patients with ST elevation acute myocardial infarction using optical coherence tomography (OCT)." *Circulation* 106(19): 698-698 3440 Suppl. S,.

Jang, I. K., G. J. Tearney, et al. (2000). "Comparison of optical coherence tomography and intravascular ultrasound for detection of coronary plaques with large lipid-core in living patients." *Circulation* 102(18): 509-509.

Jeng, J. C., A. Bridgeman, et al. (2003). "Laser Doppler imaging determines need for excision and grafting in advance of clinical judgment: a prospective blinded trial." *Burns* 29(7): 665-670.

Jesser, C. A., S. A. Boppart, et al. (1999). "High resolution imaging of transitional cell carcinoma with optical coherence tomography: feasibility for the evaluation of bladder pathology." *British Journal of Radiology* 72: 1170-1176.

Johnson, C. A., J. L. Keltner, et al. (2002). "Baseline visual field characteristics in the ocular hypertension treatment study." *Ophthalmology* 109(3): 432-7.

Jones, R. C. (1941). "A new calculus for the treatment of optical systems III. The Sohncke theory of optical activity." *Journal of the Optical Society of America* 31 (7): 500-503.

Jones, R. C. (1941). "A new calculus for the treatment of optical systems I. Description and discussion of the calculus." *Journal of the Optical Society of America* 31(7): 488-493.

Jones, R. C. (1942). "A new calculus for the treatment of optical systems. IV." Journal of the *Optical Society of America* 32(8): 486-493.

Jones, R. C. (1947). "A New Calculus for the Treatment of Optical Systems .6. Experimental Determination of the Matrix." *Journal of the Optical Society of America* 37(2): 110-112.

Jones, R. C. (1947). "A New Calculus for the Treatment of Optical Systems . 5. A More General Formulation, and Description of Another Calculus." *Journal of the Optical Society of America* 37(2): 107-110.

Jones, R. C. (1948). "A New Calculus for the Treatment of Optical Systems .7. Properties of the N-Matrices." *Journal of the Optical Society of America* 38(8): 671-685.

Jones, R. C. (1956). "New Calculus for the Treatment of Optical Systems .8. Electromagnetic Theory." *Journal of the Optical Society of America* 46(2): 126-131.

Jopson, R. MThe ., L. E. Nelson, et al. (1999). "Measurement of second-order polarization-mode dispersion vectors in optical fibers." *Ieee Photonics Technology Letters* 11 (9): 1153-1155.

Jost, B. M., A. V. Sergienko, et al. (1998). "Spatial correlations of spontaneously down-converted photon pairs detected with a single-photon-sensitive CCD camera." *Optics Express* 3(2): 81-88.

Kaplan, B., E. Compain, et al. (2000). "Phase-modulated Mueller ellipsometry characterization of scattering by latex sphere euspensions." *Applied Optics* 39 (4): 629-636.

Kass, M. A., D. K. Heuer, et al. (2002). "The Ocular Hypertension Treatment Study: a randomized trial determines that topical ocular hypotensive medication delays or prevents the onset of primary open-angle glaucoma." *Archives of Ophthalmology* 120(6): 701-13; discussion 829-30.

Kasuga, Y., J. Arai, et al. (2000). "Optical coherence tomograghy to confirm early closure of macular holes." *American Journal of Ophthalmology* 130(5): 675-6.

Kaufman, T., S. N. Lusthaus, et al. (1990). "Deep Partial Skin Thickness Burns—a Reproducible Animal-Model to Study Burn Wound-Healing." *Burns* 16(1): 13-16.

Kemp, N. J., J. Park, et al. (2005). "High-sensitivity determination of birefringence in turbid media coherence with enhanced polar-sensitive optical coherence tomography." *Journal of the Optical Society of America a-Optics Image Science and Vision* 22(3): 552-560.

Kerrigan-Baumrind, L. A., H. A. Quigley, et al. (2000). "Number of ganglion cells in glaucoma eyes compared with threshold visual field tests in teh same persons." *Investigative Ophthalmology & Visual Science* 41(3): 741-8.

Kesen, M. R., G. L. Spaeth, et al. (2002). "The Heidelberg Retina Tomograph vs clinical impression in the diagnosis of glaucoma." *American Journal of Ophthalmology* 133(5): 613-6.

Kienle, A. and R. Hibst (1995). "A New Optimal Wavelength for Treatment of Port-Wine Stains." *Physics in Medicine and Biology* 40(10): 1559-1576.

Kienle, A., L. Lilge, et al. (1996). "Spatially resolved absolute diffuse reflectance measurements for noninvasive determination of the optical scattering and absorption coefficients of biological tissue." *Applied Optics* 35(13): 2304-2314.

Kim, B. Y. and S. S. Choi (1981). "Analysis and Measurement of Birefringence in Single-Mode Fibers Using the Backscattering Method." *Optics Letters* 6(11): 578-580.

Kimel, S., L. O. Svaasand, et al. (1994). "Differential Vascular-Response to Laser Photothermolysis." *Journal of Investigative Dermatology* 103(5): 693-700.

Kloppenberg, F. W. H., G. Beerthuizen, et al. (2001). "Perfusion of burn wounds assessed by Laser Doppler Imaging is related to burn depth and healing time." *Burns* 27(4): 359-363.

Knighton, R. W. and X. R. Huang (2002). "Analytical methods for scanning laser polarimetry." *Optics Express* 10(21): 1179-1189.

Knighton, R. W., X. R. Huang, et al. (2002). "Analytical model of scanning laser polarimetry for retinal nerve fiber layer assessment." *Investigative Ophthalmology & Visual Science* 43(2): 383-392.

Knuettel, A. R. S., Joseph M.: Shay, M.; Knutson, Jay R. (1994). "Stationary low-coherence light imaging and spectroscopy using a CCD camera." *Proc. SPIE*, vol. 2135: p. 239-250.

Knuttel, A. and M. Boehlau-Godau (2000). "Spatially confined and temporally resolved refractive index and scattering evaluation in human skin performed with optical coherence tomography." *Journal of Biomedical Optics* 5(1): 83-92.

Knuttel, A. and J. M. Schmitt (1993). "Stationary Depth-Profiling Reflectometer Based on Low-Coherence Interferometry." *Optics Communications* 102(3-4): 193-198.

Knuttel, A., J. M. Schmitt, et al. (1994). "Low-Coherence Reflectometry for Stationary Lateral and Depth Profiling with Acoustooptic Deflectors and a Ccd Camera." *Optics Letters* 19(4): 302-304.

Kobayashi, M., H. Hanafusa, et al. (1991). "Polarization-Independent Interferometric Optical-Time-Domain Reflectometer." *Journal of Lightwave Technology* 9(5): 623-628.

Kolios, M. C., M. D. Sherar, et al. (1995). "Large Blood-Vessel Cooling in Heated Tissues—a Numerical Study." *Physics in Medicine and Biology* 40(4): 477-494.

Koozekanani, D., K. Boyer, et al. (2001). "Retinal thickness measurements from optical coherence model tomopgrahy using a Markov boundary model." *Ieee Transactions on Medical Imaging* 20(9): 900-916.

Kop, R. H. J. and R. Sprik (1995). "Phase-sensitive interferometry with ultrashort optical pulses." *Review of Scientific Instruments* 66(12): 5459-5463.

Kramer, R. Z., J. Bella, et al. (1999). "Sequence dependent conformational variations of collagen triple-helical structure." *Nature Structural Biology* 6(5): 454-7.

Kulkarni, M. D., T. G. van Leeuwen, et al. (1998). "Velocity-estimation accuracy and frame-rate limitations in color Doppler optical coherence tomography." *Optics letters* 23(13): 1057-1059.

Kwon, Y. H., C. S. Kim, et al. (2001). "Rate of visual field loss and long-term visual outcome in primary open-angle glaucoma." *American Journal of Ophthalmology* 132(1): 47-56.

Kwong, K. F., D. Yankelevich, et al. (1993). "400-Hz Mechanical Scanning Optical Delay-Line." *Optics Letters* 18(7): 558-560.

Landers, J., I. Goldberg, et al. (2002). "Analysis of risk factors that may be associated with progression from ocular hypertension to primary open angle glaucoma." *Clin Experiment Ophthalmogy* 30(4): 242-7.

Laszlo, A. and A. Venetianer (1998). Heat Stress resistance in mammalian cells: Lessons and challenges. *Stress of Life*. 851: 169-178.

Laszlo, A. and A. Venetianer (1998). "Heat resistance in mammalian cells: lessons and challenges. [Review] [52 refs]." *Annals of the New York Academy of Sciences* 851: 169-78.

Laufer, J., R. Simpson, et al. (1998). "Effect of temperature on the optical properties of ex vivo human dermis and subdermis." *Physics in Medicine and Biology* 43(9): 2479-2489.

Lederer, D. E., J. S. Schuman, et al. (2003). "Analysis of macular volume in normal and glaucomatous eyes using optical coherence tomography." *American Journal of Ophthalmology* 135(6): 838-843.

Lee, P. P., Z. W. Feldman, et al. (2003). "Longitudinal prevalence of major eye diseases." *Archives of Ophthalmology* 121(9): 1303-1310.

Lehrer, M. S., T. T. Sun, et al. (1998). "Strategies of epithelial repair: modulation of stem cell and transit amplifying cell proliferation." *Journal of Cell Science* 111(Pt 19): 2867-75.

Leibowitz, H. M., D. E. Krueger, et al. (1980). "The Framingham Eye Study monograph: An ophthalmological and epidemiological study of cataract, glaucoma, diabetic retinopathy, macular degeneration, and visual acuity in a general population of 2631 adults, 1973-1975." *Survey of Ophthalmology* 24(Suppl): 335-610.

Leitgeb, R., C. K. Hitzenberger, et al. (2003). "Performance of fourier domain vs. time domain optical coherence tomography." *Optics Express* 11(8): 889-894.

Leitgeb, R., L. F. Schmetterer, et al. (2002). "Flow velocity measurements by frequency domain short coherence interferometry." *Proc. SPIE* 4619: 16-21.

Leitgeb, R. A., W. Drexler, et al. (2004). "Ultrahigh resolution Fourier domain optical coherence tomography." *Optics Express* 12(10): 2156-2165.

Leitgeb, R. A., C. K. Hitzenberger, et al. (2003). "Phase-shifting algorithm to achieve high-speed long-depth-rang probing by frequency-domain optical coherence tomography." *Optics Letters* 28(22): 2201-2203.

Leitgeb, R. A., L. Schmetterer, et al. (2003). "Real-time assessment of retinal blood flow with ultrafast acquisition by color Doppler Fourier domain optical coherence tomography." *Optics Express* 11(23): 3116-3121.

Leitgeb, R. A., L. Schmetterer, et al. (2004). "Real-time measurement of in vitro flow by Fourier-domain color Doppler optical coherence tomography." *Optics Letters* 29 (2): 171-173.

LeRoyBrehonnet, F. and B. LeJeune (1997). "Utilization of Mueller matrix formalism to obtain optical targets depolarization and polarization properites." *Progress in Quantum Electronics* 21(2): 109-151.

Leske, M. C., A. M. Connell, et al. (1995). "Risk factors for open-angle glaucoma. The Barbados Eye Study. [see comments]." *Archives of Ophthalmology* 113(7): 918-24.

Leske, M. C., A. M. Connell, et al. (2001). "Incidence of open-angle glaucoma: the Barbados Eye Studies. The Barbados Eye Studies Group. [see comments]." *Archives of Ophthalmology* 119(1): 89-95.

Leske, M. C., A. Heijl, et al. (1999). "Early Manifest Glaucoma Trial. Design and Baseline Data." *Ophthalmology* 106(11): 2144-2153.

Lewis, S. E., J. R. DeBoer, et al. (2005). "Sensitive, selective, and analytical improvements to a porous silicon gas sensor." *Sensors and Actuators B: Chemical* 110(1): 54-65.

Lexer, F., C. K. Hitzenberger, et al. (1999). "Dynamic coherent focus OCT with depth-independent transversal resolution." *Journal of Modern Optics* 46(3): 541-553.

Li, X., C. Chudoba, et al. (2000). "Imaging needle for optical coherence tomography." *Optics Letters* 25: 1520-1522.

Li, X., T. H. Ko, et al. (2001). "Intraluminal fiber-optic Doppler imaging catheter for structural and functional optical coherence tomography." *Optics Letters* 26: 1906-1908.

Liddington, M. I. and P. G. Shakespeare (1996). "Timing of the thermographic assessment of burns." *Burns* 22(1): 26-8.

Lindmo, T., D. J. Smithies, et al. (1998). "Accuracy and noise in optical Doppler tomography studied by Monte Carlo simulation." *Physics in Medicine and Biology* 43(10): 3045-3064.

Liu, J., X. Chen, et al. (1999). "New thermal wave aspects on burn evaluation of skin subjected to instantaneous heating." *IEEE Transactions on Biomedical Engineering* 46(4): 420-8.

Luke, D. G., R. McBride, et al. (1995). "Polarization mode dispersion minimization in fiber-wound piezoelectric cylinders." *Optics Letters* 20(24): 2550-2552.

MacNeill, B. D., I. K. Jang, et al. (2004). "Focal and multi-focal plaque distributions in patients with macrophage acute and stable presentations of coronary artery disease." *Journal of the American College of Cardiology* 44(5): 972-979.

Mahgerefteh, D. and C. R. Menyuk (1999). "Effect of first-order PMD compensation on the statistics of pulse broadening in a fiber with randomly varying birefringence." *Ieee Photonics Technology Letters* 11(3): 340-342.

Maitland, D. J. and J. T. Walsh, Jr. (1997). "Quantitative measurements of linear birefringence during heating of native collagen." *Lasers in Surgery & Medicine* 20 (3): 310-8.

Majaron, B., S. M. Srinivas, et al. (2000). "Deep coagulation of dermal collagen with repetitive Er : YAG laser irradiation." *Lasers in Surgery and Medicine* 26(2): 215-222.

Mansuripur, M. (1991). "Effects of High-Numerical-Aperture Focusing on the State of Polarization in Optical and Magnetooptic Data-Storage Systems." *Appled Optics* 30(22): 3154-3162.

Marshall, G. W., S. J. Marshall, et al. (1997). "The dentin substrate: structure and properties related to bonding." *Journal of Dentistry* 25(6): 441-458.

Martin, P. (1997). "Wound healing—Aiming for perfect skin regeneration." *Science* 276 (5309): 75-81.

Martinez, O. E. (1987). "3000 Times Grating Compressor with Positive Group-Velocity Dispersion—Application to Fiber Compensation in 1.3-1.6 Mu-M Region." *Ieee Journal of Quantum Electronics* 23(1): 59-64.

Martinez, O. E., J. P. Gordon, et al. (1984). "Negative Group-Velocity Dispersion Using Refraction." *Journal of the Optical Society of America a-Optics Image Science and Vision* 1(10): 1003-1006.

McKinney, J. D., M. A. Webster, et al. "Characterization and imaging in optically scattering media by use of laser speckle and a variable-coherence scource." *Optics Letters* 25(1): 4-6.

Miglior, S., M. Casula, et al. (2001). "Clinical ability of Heidelberg retinal tomograph examination to detect glaucomatous visual field changes." *Ophthalmology* 108 (9): 1621-7.

Milner, T. E., D. M. Goodman, et al. (1996). "Imaging laser heated subsurface chromophores in biological materials: Determination of lateral physical dimensions." *Physics in Medicine and Biology* 41(1): 31-44.

Milner, T. E., D. M. Goodman, et al. (1995)."Depth Profiling of Laser-Heated Chromophores in Biological Tissues by Pulsed Photothermal Radiometry." *Journal of the Optical Society of America a-Optics Image Science and Vision* 12 (7): 1479-1488.

Milner, T. E., D. J. Smithies, et al. (1996). "Depth determination of chromophores in human skin by pulsed photothermal radiometry." *Applied Optics* 35(19): 3379-3385.

Mishchenko, M. I. and J. W. Hovenier (1995). "Depolarization of Light Backscattered by Randomly Oriented Nonspherical Particles." *Optics Letters* 20(12): 1356-&.

Mistlberger, A., J. M. Liebmann, et al. (1999). "Heidelberg retina tomography and optical coherence tomography in normal, ocular-hypertensive, and glaucomatous eyes." *Ophthalmology* 106(10): 2027-32.

Mitsui, T. (1999). "High-speed detection of ballistic photons propagating through suspensions using spectral interferometry." *Japanese Journal of Applied Physics Part 1—Reuglar Papers Short Notes & Review Papers* 38(5A): 2978-2982.

Molteno, A. C., N. J. Bosma, et al. (1999). "Otago glaucoma surgery outcome study: long-term results of trabeculectomy—1976 to 1995." *Ophthalmology* 106(9): 1742-50.

Morgner, U., W. Drexler, et al. (2000). "Spectroscopic optical coherence tomography." *Optics Letters* 25(2): 111-113.

Morgner, U., F. X. Kartner, et al. (1999). "Sub-two-cycle pulses from a Kerr-lens mode-locked Ti : sapphire laser (vol. 24, p. 411, 1999)." *Optics Letters* 24(13): 920-920.

Mourant, J. R., A. H. Hielscher, et al. (1998). "Evidence of intrinsic differences in the light scattering properites of tumorigenic and nontumorigenic cells." *Cancer Cytopathology* 84(6): 366-374.

Muller, M., J. Squier, et al. (1998). "Dispersion pre-compensation of 15 femtosecond optical pulses for high-numerical-aperture objectives." *Journal of Microscopy-Oxford* 191: 141-150.

Muscat, S., N. McKay, et al. (2002). "Repeatability and reproducibility of corneal thickness measurements by optical coherence tomography." *Investigative Ophthalmology & Visual Science* 43(6): 1791-5.

Musch, D. C., P. R. Lichter, et al. (1999). "The Collaborative Initial Glaucoma Treatment Study. Study Design, MethodsR, and Baseline Characteristics of Enrolled Patients." *Ophthalmology_* 106: 653-662.

Neerken, S., Lucassen, G.W., Bisschop, M.A., Lenderink, E., Nuijs, T.A.M. (2004). "Characterization of age-related effects in human skin: A comparative study that applies confocal lasser scanning microscopy and optical coherence tomography." *Journal of Biomedical Optics* 9(2): 274-281.

Nelson, J. S., K. M. Kelly, et al. (2001). "Imaging blood flow in human port-wine stain in situ and in real time using optical Doppler tomography." *Archives of Dermatology* 137(6): 741-744.

Newson, T. P., F. Farahi, et al. (1988). "Combined Interferometric and Polarimetric Fiber Optic Temperature Sensor with a Short Coherence Length Source." *Optics Communications* 68(3): 161-165.

November, L. J. (1993). "Recovery of the Matrix Operators in the Similarity and Congruency Transformations—Applications in Polarimetry." *Journal of the Optical Society of America a-Optics Image Science and Vision* 10(4): 719-739.

Oh, W. Y., S. H. Yun, et al. (2005). "Wide tuning range wavelength-swept laser with two semiconductor optical amplifers." *Ieee Photonics Technology Letters* 17(3): 678-680.

Oka, K. and T. Kato (1999). "Spectroscopic polarimetry with a channeled spectrum." *Optics Letters* 24(21): 1475-1477.

Okugawa, T. and K. Rotate (1996). "Real-time optical image processing by synthesis of the coherence function using real-time holography." *Ieee Photonics Technology Letters* 8(2): 257-259.

Oshima, M., R. Torii, et al. (2001). "Finite element simulation of blood flow in the cerebral artery." *Computer Methods in Applied Mechanics and Engineering* 191 (6-7): 661-671.

Pan, Y. T., H. K. Xie, et al. (2001). "Endoscopic optical coherence tomography based on a microelectromechanical mirror." *Optics Letters* 26(24): 1966-1968.

Parisi, V., G. Manni, et al. (2001). "Correlation between optical coherence tomography, pattern electroretinogram, and visual evoked potentials in open-angle glaucoma patients." *Ophthalmology* 108(5): 905-12.

Park, B. H., M. C. Pierce, et al. (2005). "Real-time fiber-based multi-functional spectral-domain optical coherence tomography at 1.3 mu m." *Optics Express* 13(11): 3931-3944.

Park, D. H., J. W. Hwang, et al. (1998). "Use of laser Doppler flowmetry for estimation of the depth of burns." *Plastic and Reconstructive Surgery* 101(6): 1516-1523.

Pendry, J. B., A. J. Holden, et al. (1999). "Magnetism from conductors and enhanced nonlinear phenomena." *Ieee Transactions on Microwave Theory and Techniques* 47(11): 2075-2084.

Penninckx, D. and V. Morenas (1999). "Jones matrix of polarization mode dispersion." *Optics Letters* 24(13): 875-877.

Pierce, M. C., M. Shishkov, et al. (2005). "Effects of sample arm motion in endoscopic polarization-sensitive optical coherence tomography." *Optics Express* 13(15): 5739-5749.

Pircher, M., E. Gotzinger, et al. (2003). "Measurement and imaging of water concentration in human cornea with different absorption optical coherence tomography." *Optics Express* 11(18): 2190-2197.

Pircher, M., E. Gotzinger, et al. (2003). "Speckle reduction in optical coherence tomography by frequency compounding." *Journal of Biomedical Optics* 8(3): 565-569.

Podoleanu, A. G., G. M. Dobre, et al. (1998). "En-face coherence imaging using galvanometer scanner modulation." *Opitcs Letters* 23(3): 147-149.

Podoleanu, A. G. and D. A. Jackson (1999). "Noise analysis of a combined optical coherence tomograph and a confocal scanning ophthalmoscope." *Applied Optics* 38(10): 2116-2127.

Podoleanu, A. G., J. A. Rogers, et al. (2000). "Three dimensional OCT images from retina and skin." *Optics Express* 7(9): 292-298.

Podoleanu, A. G., M. Seeger, et al. (1998). "Transversal and longitudinal images from the retina of the living eye using low coherence reflectometry." *Journal of Biomedical Optics* 3(1): 12-20.

Poole, C. D. (1988). "Statistical Treatment of Polarization Dispersion in Single-Mode Fiber." *Optics Letters* 13(8): 687-689.

Povazay, B., K. Bizheva, et al. (2002). "Submicrometer axial resolution optical coherence tomography." *Optics Letters* 27(20): 1800-1802.

Qi, B., A. P. Himmer, et al. (2004). "Dynamic focus control in high-speed optical coherence tomography based on a microelectromechanical mirror." *Optics Communications* 232(1-6): 123-128.

Radhakrishnan, S., A. M. Rollins, et al. (2001). "Real-time optical coherence tomography of the anterior segment at 1310 nm." *Archives of Ophthalmology* 119(8): 1179-1185.

Rogers, A. J. (1981). "Polarization-Optical Time Domain Reflectometry—a Technique for the Measurement of Field Distributions." Applied Optics 20(6): 1060-1074.

Rollins, A. M. and J. A. Izatt (1999). "Optimal interferometer designs for optical coherence tomography." *Optics Letters* 24(21): 1484-1486.

Rollins, A. M., R. Ung-arunyawee, et al. (1999). "Real-time in vivo imaging of human gastrointestinal ultrastructure by use of endoscopic optical coherence tomography with a novel efficient interferometer design." *Optics Letters* 24(19): 1358-1360.

Rollins, A. M., S. Yazdanfar, et al. (2002). "Real-time in vivo colors Doppler optical coherence tomography." *Journal of Biomedical Optics* 7(1): 123-129.

Rollins, A. M., S. Yazdanfar, et al. (2000). "Imaging of human retinal hemodynamics using color Doppler optical coherence tomography." *Investigative Ophthalmology & Visual Science* 41(4): S548-S548.

Sandoz, P. (1997). "Wavelet transform as a processing tool in white-light interferometry." *Optics Letters* 22(14): 1065-1067.

Sankaran, V., M. J. Everett, et al. (1999). "Comparison of polarized-light propagation in biological tissue and phantoms." *Optics Letters* 24(15): 1044-1046.

Sankaran, V., J. T. Walsh, et al. (2000). "Polarized light propagation through tissue phanto, ehms containing densely packed scatterers." *Optics Letters* 25(4): 239-241.

Sarunic, M. V., M. A. Choma, et al. (2005). "Instantaneous complex conjugate resolved spectral domain and swept-source OCT using 3×3 fiber couplers." *Optics Express* 13(3): 957-967.

Sathyam, U. S., B. W. Colston, et al. (1999). "Evaluation of optical coherence quantitation of analytes in turbid media by use of two wavelenths." *Applied Optics* 38(10): 2097-2104.

Schmitt, J. M. (1997). "Array detection for speckle reduction in optical coherence microscopy." *Physics in Medicine and Biology* 42(7): 1427-1439.

Schmitt, J. M. (1999). "Optical coherence tomography (OCT): A review." *Ieee Journal of Selected Topics in Quantum Electronics* 5(4): 1205-1215.

Schmitt, J. M. and A. Knuttel (1997). "Model of optical coherence tomography of heterogeneous tissue." *Journal of the Optical Society of America a-Optics Image Science and Vision* 14(6): 1231-1242.

Schmitt, J. M., S. L. Lee, et al. (1997). "An optical coherence microscope with enhanced resolving power in thick tissue." *Optics Communications* 142(4-6): 203-207.

Schmitt, J. M., S. H. Xiang, et al. (1998). "Differential absorption imaging with optical coherence tomography." *Journal of the Optical Society of America a-Optics Image Science and Vision* 15(9): 2288-2296.

Schmitt, J. M., S. H. Xiang, et al. (1999). "Speckle in optical coherence tomography." *Journal of Biomedical Optics* 4(1): 95-105.

Schmitt, J. M., M. J. Yadlowsky, et al. (1995). "Subsurface Imaging of Living Skin with Optical Coherence Microscopy." *Dermatology* 191(2): 93-98.

Shi, H., J. Finlay, et al. (1997). "Multiwavelength 10-GHz picosecond pulse generation from a single-stripe semiconductor diode laser." *Ieee Photonics Technology Letters* 9(11): 1439-1441.

Shi, H., I. Nitta, et al. (1999). "Demonstration of phase correlation in multiwavelength mode-locked semiconductor diode lasers." *Optics Letters* 24(4): 238-240.

Simon, R. (1982). "The Connection between Mueller and Jones Matrices of Polarization Optics." *Optics Communications* 42(5): 293-297.

Smith, P. J. M., (2000) "Variable-Focus Microlenses as a Potential Technology for Endoscopy." SPIE (vol. 3919), USA pp. 187-192.

Smithies, D. J., T. Lindmo, et al. (1998). "Signal attenuation and localization in optical coherence tomography studied by Monte Carlo simulation." *Physics in Medicine and Biology* 43(10): 3025-3044.

Sorin, W. V. and D. F. Gray (1992). "Simultaneous Thickness and Group Index Measurement Using Optical Low-Coherence Reflectometry." *Ieee Photonics Technology Letters* 4(1): 105-107.

Sticker, M., C. K. Hitzenberger, et al. (2001). "Quantitative differential phase measurement and imaging in transparent and turbid media by optical coherence tomography." *Optics Letters* 26(8): 518-520.

Sticker, M., M. Pircher, et al. (2002). "En face imaging of single cell layers by differential phase-contrast optical coherence microscopy." *Optics Letters* 27(13): 1126-1128.

Stoller, P., B. M. Kim, et al. (2002). "Polarization-dependent optical second-harmonic imaging of a rat-tail tendon." *Journal of Biomedical Optics* 7(2): 205-214.

Sun, C. S. (2003). "Multiplexing of fiber-optic acoustic sensors in a Michelson interferometer configuration." *Optics Letters* 28(12): 1001-1003.

Swanson, E. A., J. A. Izatt, et al. (1993). "In-Vivo Retinal Imaging by Optical Coherence Tomography." *Optics Letters* 18(21): 1864-1866.

Takada, K., A. Himeno, et al. (1991). "Phase-Noise and Shot-Noise Limited Operations of Low Coherence Optical-Time Domain Reflectometry." *Applied Physics Letters* 59(20): 2483-2485.

Takenaka, H. (1973). "Unified Formalism for Polarization Optics by Using Group-Theory I (Theory)." *Japanese Journal of Applied Physics* 12(2): 226-231.

Tanno, N., T. Ichimura, et al. (1994). "Optical Multimode Frequency-Domain Reflectometer." *Optics Letters* 19(8): 587-589.

Tan-no, N., T. Ichimura, et al. (1994). "Optical Multimode Frequency-Domain Reflectometer." *Optics Letters* 19(8): 587-589.

Targowski, P., M. Wojtkowski, et al. (2004). "Complex spectral OCT in human eye imaging in vivo." *Optics Communications* 229(1-6): 79-84.

Tearney, G. J., S. A. Boppart, et al. (1996). "Scanning single-mode fiber optic catheter-endoscope for optical cocherence tomography (vol. 21, p. 543, 1996)." *Optics Letters* 21(12): 912-912.

Tearney, G. J., B. E. Bouma, et al. (1996). "Rapid acquisition of in vivo biological images by use of optical coherence tomography." *Optics Letters* 21(17): 1408-1410.

Tearney, G. J., B. E. Bouma, et al. (1997). "In vivo endoscopic optical biopsy with optical coherence tomography." *Science* 276(5321): 2037-2039.

Tearney, G. J., M. E. Brezinski, et al. (1996). "Catheter-based optical imaging of a human coronary artery." *Circulation* 94(11): 3013-3013.

Tearney, G. J., M. E. Brezinski, et al. (1997). "In vivo endoscopic optical biopsy with optical coherence tomography." *Science* 276(5321): 2037-9.

Tearney, G. J., M. E. Brezinski, et al. (1997). "Optical biopsy in human gastrointestinal tissue using optical coherence tomography." *American Journal of Gastroenterology* 92(10): 1800-1804.

Tearney, G. J., M. E. Brezinski, et al. (1995). "Determination of the refractive index of highly scattering human tissue by optical coherence tomography." *Optics Letters* 20(21): 2258-2260.

Tearney, G. J., I. K. Jang, et al. (2000). "Porcine coronary imaging in vivo by optical coherence tomography." *Acta Cardiologica* 55(4): 233-237.

Tearney, G. J., R. H. Webb, et al. (1998). "Spectrally encoded confocal microscopy." *Optics Letters* 23(15): 1152-1154.

Tearney, G. J., H. Yabushita, et al. (2003). "Quantification of macrophage content in atherosclerotic plaques by optical coherence tomography." *Circulation* 107(1): 113-119.

Tower, T. T. and R. T. Tranquillo (2001). "Alignment maps of tissues: I. Microscopic elliptical polarimetry." *Biophysical Journal* 81(5): 2954-2963.

Tower, T. T. and R. T. Tranquillo (2001). "Alignment maps of tissues: II. Fast harmonic analysis for imaging." *Biophysical Jouranl* 81(5): 2964-2971.

Troy, T. L. and S. N. Thennadil (2001). "Optical properties of human skin in the near infrared wavelength rang of 1000 to 2200 nm." *Journal of Biomedical Optics* 6 (2): 167-176.

Vabre, L., A. Dubois, et al. (2002). "Thermal-light full-field optical coherence tomography." *Optics Letters* 27(7): 530-532.

Vakhtin, A. B., D. J. Kane, et al. (2003). "Common-path interferometer for frequency-domain optical coherence tomography." *Applied Optics* 42(34): 6953-6958.

Vakhtin, A. B., K. A. Peterson, et al. (2003). "Differential spectral interferometry:an imaging technique for biomedical applications." *Optics Letters* 28(15): 1332-1334.

Vakoc, B. J., S. H. Yun, et al. (2005). "Phase-resolved optical frequency domain imaging." *Optics Express* 13(14): 5483-5493.

van Leeuwen, T. G., M. D. Kulkarni, et al. (1999). "High-flow-velocity and shear-rate imaging by use of color Doppler optical coherence tomography." *Optics Letters* 24(22): 1584-1586.

Vansteenkiste, N., P. Vignolo, et al. (1993). "Optical Reversibility Theorems for Polarization—Application to Remote-Control of Polarization." *Journal of the Optical Society of America a-Optics Image Science and Vision* 10(10): 2240-2245.

Vargas, O., E. K. Chan, et al. (1999). "Use of an agent to reduce scattering in skin." *Lasers in Surgery and Medicine* 24(2): 133-141.

Wang, R. K. (1999). "Resolution improved optical coherence-gated tomography for imaging through biological tissues." *Journal of Modern Optics* 46(13): 1905-1912.

Wang, X. J., T. E. Milner, et al. (1997). "Measurement of fluid-flow-velocity profile in turbid media by the use of optical Doppler tomography." *Applied Optics* 36(1): 144-149.

Wang, X. J., T. E. Milner, et al. (1995). "Characterization of Fluid-Flow Velocity by Optical Doppler Tomography." *Optics Letters* 20(11): 1337-1339.

Wang, Y. M., J. S. Nelson, et al. (2003). "Optimal wavelength for ultrahigh-resolution optical coherence tomography." *Optics Express* 11(12): 1411-1417.

Wang, Y. M., Y. H. Zhao, et al. (2003). "Ultrahigh-resolution optical coherence tomography by broadband continuum generation from a photonic crystal fiber." *Optics Letters* 28(3): 182-184.

Watkins, L. R., S. M. Tan, et al. (1999). "Determination of interferometer phase distributions by use of wavelets." *Optics Letters* 24(11): 905-907.

Wetzel, J. (2001). "Optical coherence tomography in dermatology: a review." *Skin Research and Technology* 7(1): 1-9.

Wentworth, R. H. (1989). "Theoretical Noise Performance of Coherence-Multiplexed Interferometric Sensors." *Journal of Lightwave Technology* 7(6): 941-956.

Westphal, V., A. M. Rollins, et al. (2002). "Correction of geometric and refractive image distortions in optical coherence tomography applying Fermat's principle." *Optics Express* 10(9): 397-404.

Westphal, V., S. Yazdanfar, et al. (2002). "Real-time, high velocity-resolution color Doppler optical coherence tomography." *Optics Letters* 27(1): 34-36.

Williams, P. A. (1999). "Rotating-wave-plate Stokes polarimeter for differential group delay measurements of polarization-mode dispersion." *Applied Optics* 38(31): 6508-6515.

Wojtkowski, M., T. Bajraszewski, et al. (2003). "Real-time in vivo imaging by high-speed spectral optical coherence tomography." *Optics Letters* 28(19): 1745-1747.

Wojtkowski, M., A. Kowalczyk, et al. "Full range complex spectral optical coherence tomography technique in eye imaging." *Optics Letters* 27(16): 1415-1417.

Wojtkowski, M., R. Leitgeb, et al. (2002). "In vivo human retinal imaging by Fourier domain optical coherence tomography." *Journal of Biomedical Optics* 7(3): 457-463.

Wojtkowski, M., R. Leitgeb, et al. (2002). "Fourier domain OCT imaging of the human eye in vivo." *Proc. SPIE* 4619: 230-236.

Wojtkowski, M., V. J. Srinivasan, et al. (2004). "Ultrahigh-resolution, high-speed, Fourier domain optical coherence tomography and methods for dispersion compensation." *Optics Express* 12(11): 2404-2422.

Wong, B. J. F., Y. H. Zhao, et al. (2004). "Imaging the internal structure of the rat cochlea using optical coherence tomography at 0.827 mu m and 1.3 mu m." *Otolaryngology—Head and Neck Surgery* 130(3): 334-338.

Yabushita, H. B., et al. (2002) "Measurement of Thin Fibrous Caps in Atherosclerotic Plaques by Optical Coherence Tomography." American Heart Association, INC, Circulation 2002;106;1640.

Yang, C., A. Wax, et al. (2001). "Phase-dispersion optical tomography." *Optics Letters* 26(10): 686-688.

Yang, C., A. Wax, et al. (2001). "Phase-referenced interferometer with subwavelength and subhertz senisitivity applied to the study of cell membrane dynamics." *Optics Letters* 26(16): 1271-1273.

Yang, C. H., A. Wax, et al. (2001). "Phase-dispersion optical tomography." *Optics Letters* 26(10): 686-688.

Yang, C. H., A. Wax, et al. (2000). "Interferometric phase-dispersion microscopy." *Optics Letters* 25(20): 1526-1528.

Yang, V. X. D., M. L. Gordon, et al. (2002). "Improved phase-resolved optical Doppler tomography using the Kasai velocity estimator and histogram segmentation." Optics Communications 208(4-6): 209-214.

Yang, V. X. D., M. L. Gordon, et al. (2003). "High speed, wide velocity dynamic range Doppler optical coherence tomography (Part I): System design, signal processing, and performance." *Optics Express* 11(7): 794-809.

Yang, V. X. D., M. L. Gordon, et al. (2003). "High speed, wide velocity dynamic range Doppler optical coherence tomography (Part II): Imaging in vivo cardiac dynamics of *Xenopus laevis*." *Optics Express* 11(14): 1650-1658.

Yang, V. X. D., M. L. Gordon, et al. (2003). "High speed, wide velocity dynamic range Doppler optical coherence tomography (Part III): in vivo endoscopic imaging of blood flow in the rat and human gastrointestinal tracts." *Optics Express* 11(19): 2416-2424.

Yang, V. X. D., B. Qi, et al. (2003). "In vivo feasibility of endoscopic catheter-based Doppler optical coherence tomography." *Gastroenterology* 124(4): A49-A50.

Yao, G. and L. H. V. Wang (2000). "Theoretical and experimental studies of ultrasound-modulated optical tomography in biological tissue." *Applied Optics* 39(4): 659-664.

Yazdanfar, S. and J. A. Izatt (2002). "Self-referenced Doppler optical coherence tomography." *Optics Letters* 27(23): 2085-2087.

Yazdanfar, S., M. D. Kulkarni, et al. (1997). "High resolution imaging of in vivo cardiac dynamics using color Doppler optical coherence tomography." *Optics Express* 1 (13): 424-431.

Yazdanfar, S., A. M. Rollins, et al. (2000). "Imaging and velocimetry of the human retinal circulation with color Doppler optical coherence tomography." *Optics Letters* 25(19): 1448-1450.

Yazdanfar, S., A. M. Rollins, et al. (2000). "Noninvasive imaging and velocimetry of human retinal blood flow using color Doppler optical coherence tomography." *Investigative Ophthalmology & Visual Science* 41(4): S548-S548.

Yazdanfar, S., A. M. Rollins, et al. (2003). "In vivo imaging of human retinal flow dynamics by color Doppler optical coherence tomography." *Archives of Ophthalmology* 121(2): 235-239.

Yazdanfar, S., C. H. Yang, et al. (2005). "Frequency estimation precision in Doppler optical coherence tomography using the Cramer-Rao lower bound." *Optics Express* 13(2): 410-416.

Yun, S. H., C. Boudoux, et al. (2004). "Extended-cavity semiconductor wavelength-swept laser for biomedical imaging." *Ieee Photonics Technology Letters* 16(1): 293-295.

Yun, S. H., C. Boudoux, et al. (2003). "High-speed wavelength-swept semiconductor laser with a polygon-scanner-based wavelength filter." *Optics Letters* 28(20): 1981-1983.

Yun, S. H., G. J. Tearney, et al. (2004). "Pulsed-source and swept-source spectral-domain optical coherence tomography with reduced motion artifacts." *Optics Express* 12(23): 5614-5624.

Yun, S. H., G. J. Tearney, et al. (2004). "Removing the depth-degeneracy in optical frequency domain imaging with frequency shifting." *Optics Express* 12(20): 4822-4828.

Yun, S. H., G. J. Tearney, et al. (2004). "Motion artifacts in optical coherence tomography with frequency-domain ranging." *Optics Express* 12(13): 2977-2998.

Zhang, J., J. S. Nelson, et al. (2005). "Removal of a mirror image and enhancement of the signal-to-noise ratio in Fourier-domain optical coherence tomography using an electro-optic phase modulator." *Optics Letters* 30(2): 147-149.

Zhang, Y., M. Sato, et al. (2001). "Numerical investigations of optimal synthesis of several low coherence sources for resolution improvement." *Optics Communications* 192(3-6): 183-192.

Zhang, Y., M. Sato, et al. (2001). "Resolution improvement in optical coherence tomography by optimal synthesis of light-emitting diodes." *Optics Letters* 26(4): 205-207.

Zhao, Y., Z. Chen, et al. (2002). "Real-time phase-resolved functional optical coherence tomography by use of optical Hilbert transformation." *Optics Letters* 27(2): 98-100.

Zhao, Y. H., Z. P. Chen, et al. (2000). "Doppler standard deviation imaging for clinical monitoring of in vivo human skin blood flow." *Optics Letters* 25(18): 1358-1360.

Zhao, Y. H., Z. P. Chen, et al. (2000). "Phase-resolved optical coherence tomography and optical Doppler tomography for imaging blood flow in human skin with fast scanning speed and high velocity sensitivity." *Optics Letters* 25(2): 114-116.

Zhou, D., P. R. Prucnal, et al. (1998). "A widely tunable narrow linewidth semiconductor fiber ring laser." *IEEE Photonics Technology Letters* 10(6): 781-783.

Zuluaga, A. F. and R. Richards-Kortum (1999). "Spatially resolved spectral interferometry for determination of subsurface structure." *Optics Letters* 24(8): 519-521.

Zvyagin, A. V., J. B. FitzGerald, et al. (2000). "Real-time detection technique for Doppler optical coherence tomography." *Optics Letters* 25(22): 1645-1647.

Marc Nikles et al., "Brillouin gain spectrum characterization in single-mode optical fibers", *Journal of Lightwave Technology* 1997, 15 (10): 1842-1851.

Tsuyoshi Sonehara et al., "Forced Brillouin Spectroscopy Using Frequency-Tunable Continuous-Wave Lasers", *Physical Review Letters* 1995, 75 (23): 4234-4237.

Hajime Tanaka et al., "New Method of Superheterodyne Light Beating Spectroscopy for Brillouin-Scattering Using Frequency-Tunable Lasers", *Physical Review Letters* 1995, 74 (9): 1609-1612.

Webb RH et al. "Confocal Scanning Laser Ophthalmoscope", *Applied Optics* 1987, 26 (8): 1492-1499.

Andreas Zumbusch et al. "Three-dimensional vibrational imaging by coherent anti-Stokes Raman scattering", *Physical Review Letters* 1999, 82 (20): 4142-4145.

Katrin Kneipp et al., "Single molecule detection using surface-enhanced Raman scattering (SERS)", *Physical Review Letters* 1997, 78 (9): 1667-1670.

K.J. Koski et al., "Brillouin imaging" *Applied Physics Letters* 87, 2005.

Boas et al., "Diffusing temporal light correlation for burn diagnosis", *SPIE*, 1999, 2979:468-477.

David J. Briers, "Speckle fluctuations and biomedical optics: implications and applications", *Optical Engineering*, 1993, 32(2):277-283.

Clark et al., "Tracking Speckle Patterns with Optical Correlation", *SPIE*, 1992, 1772:77-87.

Facchini et al., "An endoscopic system for DSPI", *Optik*, 1993, 95(1):27-30.

Hrabovsky, M., "Theory of speckle dispacement and decorrelation: application in mechanics", *SPIE*, 1998, 3479:345-354.

Sean J. Kirkpatrick et al., "Micromechanical behavior of cortical bone as inferred from laser speckle data", *Journal of Biomedical Materials Research*, 1998, 39(3):373-379.

Sean J. Kirkpatrick et al., "Laser speckle microstrain measurements in vascular tissue", *SPIE*, 1999, 3598:121-129.

Loree et al., "Mechanical Properties of Model Atherosclerotic Lesion Lipid Pools", *Arteriosclerosis and Thrombosis*, 1994, 14(2):230-234.

Podbielska, H. "Interferometric Methods and Biomedical Research", *SPIE*, 1999, 2732:134-141.

Richards-Kortum et al., "Spectral diagnosis of atherosclerosis using an optical fiber laser catheter", *Ameican Heart Journal*, 1989, 118(2):381-391.

Ruth, B. "blood flow determination by the laser speckle method", *Int J Microcirc: Clin Exp*, 1990, 9:21-45.

Shapo et al., "Intravascular strain imaging: Experiments on an Inhomogeneous Phantom", *IEEE Ultrasonics Symposium* 1996, 2:1177-1180.

Shapo et al., "Ultrasonic displacement and strain imaging of coronary arteries with a catheter array", *IEEE Ultrasonics Symposium* 1995, 2:1511-1514.

Thompson et al., "Imaging in scattering media by use of laser speckle", *Opt. Soc. Am. A.*, 1997, 14(9):2269-2277.

Thompson et al., "Diffusive media characterization with laser speckle", *Applied Optics*, 1997, 36(16):3726-3734.

Tuchin, Valery V., "Coherent Optical Techniques for the Analysis of Tissue Structure and Dynamics," *Journal of Biomedical Optics*, 1999, 4(1):106-124.

M. Wussling et al., "Laser diffraction and speckling studies in skeletal and heart muscle", *Biomed, Biochim, Acta*, 1986, 45(1/2):S 23-S 27.

T. Yoshimura et al., "Statistical properties of dynamic speckles", *J. Opt. Soc. Am A*. 1986, 3(7):1032-1054.

Zimnyakov et al., "Spatial speckle correlometry in applications to tissue structure monitoring", *Applied Optics* 1997, 36(22): 5594-5607.

Zimnyakov et al., "A study of statistical properties of partially developed speckle fields as applied to the diagnosis of structural changes in human skin", *Optics and Spectroscopy*, 1994, 76(5): 747-753.

Zimnyakov et al., "Speckle patterns polarization analysis as an approach to turbid tissue structure monitoring", *SPIE* 1999, 2981:172-180.

Ramasamy Manoharan et al., "Biochemical analysis and mapping of atherosclerotic human artery using FT-IR microspectroscopy", *Atherosclerosis*, May 1993, 181-1930.

N.V. Salunke et al., "Biomechanics of Atherosclerotic Plaque" *Critical Reviews™ in Biomedical Engineering* 1997, 25(3):243-285.

D. Fu et al., "Non-invasive quantitative reconstruction of tissue elasticity using an iterative forward approach", *Phys. Med. Biol.* 2000 (45): 1495-1509.

S.B. Adams Jr. et al., "The use of polarization sensitive optical coherence tomography and elastography to assess connective tissue", Optical Soc. of American Washington 2002, p. 3.

International Search Report for International Patent application No. PCT/US2005/039740 published Feb. 21, 2006.

International Written Opinion for International Patent application No. PCT/US2005/039740 published Feb. 21, 2006.

International Search Report for International Patent application No. PCT/US2005/030294 published Aug. 22, 2006.

International Written Opinion for International Patent application No. PCT/US2005/043951 published Apr. 6, 2006.

International Search Report for International Patent application No. PCT/US2005/043951 published Apr. 6, 2006.

Erdelyi et al. "Generation of diffraction-free beams for applications in optical microlithography", J. Vac. Sci. Technol. B 15 (12), Mar./Apr. 1997, pp. 287-292.

International Search Report for International Patent application No. PCT/US2005/023664 published Oct. 12, 2005.

International Written Opinion for International Patent application No. PCT/US2005/023664 published Oct. 12, 2005.

Tearney et al., "Spectrally encoded miniature endoscopy" Optical Society of America; Optical Letters vol. 27, No. 6, Mar. 15, 2002; pp. 412-414.

Yelin et al., "Double-clad Fiber for Endoscopy" Optical Society of America; Optical Letters vol. 29, No. 20, Oct. 16, 2005; pp. 2408-2410.

International Search Report for International Patent application No. PCT/US2001/049704 published Dec. 10, 2002.

International Search Report for International Patent application No. PCT/US2004/039454 published May 11, 2005.

International Written Opinion for International Patent application No. PCT/US2004/039454 published May 11, 2005.

PCT International Preliminary Report on Patentability for International Application No. PCT/US2004/038404 dated Jun. 2, 2006.

Notice of Reasons for Rejection and English translation for Japanese Patent Application No. 2002538830 dated May 12, 2008.

Office Action dated Aug. 24, 2006 for U.S. Appl. No. 10/137,749.

Barry Cense et al., "Spectral-domain polarization-sensitive optical coherence tomography at 850nm", Coherence Domain Optical Methods and Optical Coherence Tomography in Biomedicine IX, 2005, pp. 159-162.

A. Ymeti et al., "Integration of microfluidics with a four-channel integrated optical Young interferometer immunosensor", Biosensors and Bioelectronics, Elsevier Science Publishers, 2005, pp. 1417-1421.

PCT International Search Report for Application No. PCT/US2006/018865 filed May 5, 2006.

International Written Opinion for International Patent application No. PCT/US2006/018865 filed May 5, 2006.

John M. Poneros, "Diagnosis of Barrett's esophagus using optical coherence tomography", Gastrointestinal Endoscopy clinics of North America, 14 (2004) pp. 573-588.

P.F. Escobar et al., "Diagnostic efficacy of optical coherence tomography in the management of preinvasive and invasive cancer of uterine cervix and vulva", Int. Journal of Gynecological Cancer 2004, 14, pp. 470-474.

Ko T et al., "Ultrahigh resolution in vivo versus ex vivo OCT imaging and tissue preservation", Conference on Lasers and electro-optics, 2001, pp. 252-253.

Paul M. Ripley et al., "A comparison of Artificial Intelligence techniques for spectral classification in the diagnosis of human pathologies based upon optical biopsy", Journal of Optical Society of America, 2000, pp. 217-219.

Wolfgang Drexler et al., "Ultrahigh-resolution optical coherence tomography", Journal of Biomedical Optics Spie USA, 2004, pp. 47-74.

PCT International Search Report for Application No. PCT/US2006/016677 filed Apr. 28, 2006.

International Written Opinion for International Patent application No. PCT/US2006/016677 filed Apr. 28, 2006.

Office Action dated Nov. 13, 2006 for U.S. Appl. No. 10/501,268.

Office Action dated Nov. 20, 2006 for U.S. Appl. No. 09/709,162.

PCT International Search Report and Written Opinion for Application No. PCT/US2004/023585 filed Jul. 23, 2004.

Office Action dated Dec. 6, 2006 for U.S. Appl. No. 10/997,789.

Elliott, K. H. "The use of commercial CCD cameras as linear detectors in the physics undergraduate teaching laboratory", European Journal of Physics, 1998, pp. 107-117.

Lauer, V. "New approach to optical diffraction tomography yielding a vector equation of diffraction tomography and a novel tomographic microscope", Journal of Microscopy vol. 205, Issue 2, 2002, pp. 165-176.

Yu, P. et al. "Imaging of tumor necroses using full-frame optical coherence imaging", Proceedings of SPIE vol. 4956, 2003, pp. 34-41.

Zhao, Y. et al. "Three-dimensional reconstruction of in vivo blood vessels in human skin using phase-resolved optical Doppler tomography", IEEE Journal of Selected Topics in Quantum Electronics 7.6 (2001): 931-935.

Office Action dated Dec. 18, 2006 for U.S. Appl. No. 10/501,276.

Devesa, Susan S. et al. (1998) "Changing Patterns in the Incidence of Esophegeal and Gastric Carcinoma in the United States." American Cancer Society vol. 83, No. 10 pp. 2049-2053.

Barr, H et al. (2005) "Endoscopic Therapy for Barrett's Oesophaugs" Gut vol. 54:875-884.

Johnston, Mark H.(2005) "Technology Insight: Ablative Techniques for Barrett's Esophagus—Current and Emerging Trends" www.Nature.com/clinicalpractice/gasthep.

Falk, Gary W. et al. (1997) "Surveillance of Patients with Barrett's Esophagus for Dysplasia and Cancer with Ballon Cytology" Gastrorenterology vol. 112, pp. 1787-1797.

Sepchler, Stuart Jon. (1997) "Barrett's Esophagus: Should We Brush off this Balloning Problem?" Gastroenterology vol. 112, pp. 2138-2152.

Froehly, J. et al. (2003) "Multiplexed 3D Imaging Using Wavelength Encoded Spectral Interferometry: A Proof of Principle" Optics Communications vol. 222, pp. 127-136.

Kubba A.K. et al. (1999) "Role of p53 Assessment in Management of Barrett's Esophagus" Digestive Disease and Sciences vol. 44, No. 4. pp. 659-667.

Reid, Brian J. (2001) "p53 and Neoplastic Progression in Barrett's Esophagus" The American Journal of Gastroenterology vol. 96, No. 5, pp. 1321-1323.

Sharma, P. et al.(2003) "Magnification Chromoendoscopy for the Detection of Intestinal Metaplasia and Dysplasia in Barrett's Oesophagus" Gut vol. 52, pp. 24-27.

Kuipers E.J et al. (2005) "Diagnostic and Therapeutic Endoscopy" Journal of Surgical Oncology vol. 92, pp. 203-209.

Georgakoudi, Irene et al. (2001) "Fluorescence, Reflectance, and Light-Scattering Spectroscopy for Evaluating Dysplasia in Patients with Barrett's Esophagus" Gastroenterology vol. 120, pp. 1620-1629.

Adrain, Alyn L. et al. (1997) "High-Resolution Endoluminal Sonography is a Sensitive Modality for the Identification of Barrett's Meaplasia" Gastrointestinal Endoscopy vol. 46, No. 2, pp. 147-151.

Canto, Marcia Irene et al (1999) "Vital Staining and Barrett's Esophagus" Gastrointestinal Endoscopy vol. 49, No. 3, part 2, pp. 12-16.

Evans, John A. et al. (2006) "Optical Coherence Tomography to Identify Intramucosal Carcinoma and High-Grade Dysplasia in Barrett's Esophagus" Clincial Gastroenterology and Hepatology vol. 4, pp. 38-3.

Poneros, John M. et al. (2001) "Diagnosis of Specialized Intestinal Metaplasia by Optical Coherence Tomography" Gastroenterology vol. 120, pp. 7-12.

Ho, W. Y. et al. (2005) "115 KHz Tuning Repetition Rate Ultrahigh-Speed Wavelength-Swept Semiconductor Laser" Optics Letters col. 30, No. 23, pp. 3159-3161.

Brown, Stanley B. et al. (2004) "The Present and Future Role of Photodynamic Therapy in Cancer Treatment" The Lancet Oncology vol. 5, pp. 497-508.

Boogert, Jolanda Van Den et al. (1999)"Endoscopic Ablation Therapy for Barrett's Esophagua with High-Grade Dysplasia: A Review" The American Journal of Gastroenterology vol. 94, No. 5, pp. 1153-1160.

Sampliner, Richard E. et al. (1996) "Reversal of Barrett's Esophagus with Acid Suppression and Multipolar Electrocoagulation: Preliminary Results" Gastrointestinal Endoscopy vol. 44, No. 5, pp. 532-535.

Sampliner, Richard E. (2004) "Endoscopic Ablative Therapy for Barrett's Esophagus: Current Status" Gastrointestinal Endoscopy vol. 59, No. 1, pp. 66-69.

Soetikno, Roy M. et al. (2003) "Endoscopic Mucosal resection" Gastrointestinal Endoscopy vol. 57, No. 4, pp. 567-579.

Ganz, Robert A. et al. (2004) "Complete Ablation of Esophageal Epithelium with a Balloon-based Bipolar Electrode: A Phased Evaluation in the Porcine and in the Human Esophagus" Gastrointestinal Endoscopy vol. 60, No. 6, pp. 1002-1010.

Pfefer, Jorje at al. (2006) "Performance of the Aer-O-Scope, A Pneumatic, Self Propelling, Self Navigating Colonoscope in Animal Experiements" Gastrointestinal Endoscopy vol. 63, No. 5, pp. AB223.

Overholt, Bergein F. et al. (1999) "Photodynamic Therapy for Barrett's Esophagus: Follow-Up in 100 Patients" Gastrointestinal Endoscopy vol. 49, No. 1, pp. 1-7.

Vogel, Alfred et al. (2003) "Mechanisms of Pulsed Laser Ablation of Biological Tissues" American Chemical Society vol. 103, pp. 577-644.

McKenzie, A. L. (1990) "Physics of Thermal Processes in Laser-Tissue Interaction" Phys. Med. Biol vol. 35, No. 9, pp. 1175-1209.

Anderson, R. Rox et al. (1983) "Selective Photothermolysis" Precise Microsurgery by Selective Absorption of Pulsed Radiation Science vol. 220, No. 4596, pp. 524-527.

Jacques, Steven L. (1993) "Role of Tissue Optics and Pulse Duration on Tissue Effects During High-Power Laser Irradiation" Applied Optics vol. 32, No. 13, pp. 2447-2454.

Nahen, Kester et al. (1999) "Investigations on Acosustic On-Line Monitoring of IR Laser Ablation of burned Skin" Lasers in Surgery and Medicine vol. 25, pp. 69-78.

Jerath, Maya R. et al. (1993) "Calibrated Real-Time Control of Lesion Size Based on Reflectance Images" Applied Optics vol. 32, No. 7, pp. 1200-1209.

Jerath, Maya R. et al (1992) "Dynamic Optical Property Changes: Implications for Reflectance Feedback Control of Photocoagulation" Journal of Photochemical,.Photobiology. B: Biol vol. 16, pp. 113-126.

Deckelbaum, Lawrence I. (1994) "Coronary Lasers Angioplasty" *Lasers in Surgery and Medicine* vol. 14, pp. 101-110.
Kim, B.M. et al. (1998) "Optical Feedback Signal for Ultrashort Laser Pulse Ablation of Tissue" *Applied Surface Science* vol. 127-129, pp. 857-862.
Brinkman, Ralf et al. (1996) "Analysis of Cavitation Dynamics During Pulsed Laser Tissue Ablation by Optical On-Line Monitoring" *IEEE Journal of Selected Topics in Quantum Electronics* vol. 2, No. 4, pp. 826-835.
Whelan, W.M. et al. (2005) "A novel Strategy for Monitoring Laser Thermal Therapy Based on Changes in Optothermal Properties of Heated Tissues" *International Journal of Thermophysics* vol. 26., No. 1, pp. 233-241.
Thomsen, Sharon et al. (1990) "Microscopic Correlates of Macroscopic Optical Property Changes During Thermal Coagulation of Myocardium" *SPIE* vol. 1202, pp. 2-11.
Khan, Misban Huzaira et al. (2005) "Intradermally Focused Infrared Laser Pulses: Thermal Effects at Defind Tissue Depths" *Lasers in Surgery and Medicine* vol. 36, pp. 270-280.
Neumann, R.A. et al. (1991) "Enzyme Histochemical Analysis of Cell Viability After Argon Laser-Journal-Induced Coagulation Necrosis of the Skin" *Journal of the American Academy of Dermatology* vol. 25, No. 6, pp. 991-998.
Nadkarni, Seemantini K. et al (2005) "Charaterization of Atherosclerotic Plaques by Laser Speckle Imaging" *Circulation* vol. 112, pp. 885-892.
Zimnyakov, Dmitry A. et al (2002) "Speckle-Contrast Monitoring of Tissue Thermal Modification" *Applied Optics* vol. 41, No. 28, pp. 5989-5996.
Morelli, J.G., et al (1986) "Tunable Dye Lasers (577 nm) Treatment of Port Wine Stains" *Lasers in Surgery and Medicine* vol. 6, pp. 94-99.
French, P.M.W. et al. (1993) "Continuous-wave Mode-Locked $Cr^{4+}$: YAG Laser" *Optics Letters* vol. 18, No. 1, pp. 39-41.
Sennaroglu, Alphan at al. (1995) "Efficient Continuous-Wave Chromium-Doped YAG Laser" *Journal of Optical Society of America* vol. 12, No. 5, pp. 930-937.
Bouma, B et al. (1994) "Hybrid Mode Locking of a Flash-Lamp-Pumped Ti: $Al_2O_3$ Laser" *Optics Letters* vol. 19, No. 22, pp. 1858-1860.
Bouma, B et al. (1995) "High Resolution Optical Coherence Tomography Imaging Using a Mode-Locked Ti: $Al_2O_3$ Laser Source" *Optics Letters* vol. 20, No. 13, pp. 1486-1488.
Fernández, Cabrera Delia et al. "Automated detection of retinal layer structures on optical coherence tomography images", *Optics Express* vol. 13, No. 25, Oct. 4, 2005, pp. 10200-10216.
Ishikawa, Hiroshi et al. "Macular Segmentation with optical coherence tomography", Investigative Ophthalmology & Visual Science, vol. 46, No. 6, Jun. 2005, pp. 2012-2017.
Hariri, Lida P. et al. "Endoscopic Optical Coherence Tomography and Laser-Induced Fluorescence Spectroscopy in a Murine Colon Cancer Model", Laser in Surgery and Medicine, vol. 38, 2006, pp. 305-313.
PCT International Search Report and Written Opinion for Application No. PCT/US2006/031905 dated May 3, 2007.
PCT International Search Report and Written Opinion for Application No. PCT/US2007/060481 dated May 23, 2007.
PCT International Search Report and Written Opinion for Application No. PCT/US2007/060717 dated May 24, 2007.
PCT International Search Report and Written Opinion for Application No. PCT/US2007/060319 dated Jun. 6, 2007.
D. Yelin et al., "Three-dimensional imaging using spectral encoding heterodyne interferometry", Optics Letters, Jul. 15, 2005, vol. 30, No. 14, pp. 1794-1796.
Akiba, Masahiro et al. "En-face optical coherence imaging for three-dimensional microscopy", SPIE, 2002, pp. 8-15.
Office Action dated Aug. 10, 2007 for U.S. Appl. No. 10/997,789.
Office Action dated Feb. 2, 2007 for U.S. Appl. No. 11/174,425.
PCT International Search Report and Written Opinion for Application No. PCT/US2007/060657 dated Aug. 13, 2007.
Lewis, Neil E. et al., (2006) "Applications of Fourier Transform Infrared Imaging Microscopy in Neurotoxicity", Annals New York Academy of Sciences, Dec. 17, 2006, vol. 820, pp. 234-246.

Joo, Chulmin et al., Spectral-domain optical coherence phase microscopy for quantitative phase-contrast imaging, Optics Letters, Aug. 15, 2005, vol. 30, No. 16, pp. 2131-2133.
Guo, Bujin et al., "Laser-based mid-infrared reflectance imaging of biological tissues", Optics Express, Jan. 12, 2004, vol. 12, No. 1, pp. 208-219.
Office Action dated Mar. 28, 2007 for U.S. Appl. No. 11/241,907.
Office Action dated May 23, 2007 for U.S. Appl. No. 10/406,751.
Office Action dated May 23, 2007 for U.S. Appl. No. 10/551,735.
PCT International Search Report and Written Opinion for Application No. PCT/US2007/061815 dated Aug. 2, 2007.
Sir Randall, John et al., "Brillouin scattering in systems of biological significance", Phil. Trans. R. Soc. Lond. A 293, 1979, pp. 341-348.
Takagi, Yasunari, "Application of a microscope to Brillouin scattering spectroscopy", Review of Scientific Instruments, No. 12, Dec. 1992, pp. 5552-5555.
Lees, S. et al., "Studies of Compact Hard Tissues and Collagen by Means of Brillouin Light Scattering", Connective Tissue Research, 1990, vol. 24, pp. 187-205.
Berovic, N. "Observation of Brillion scattering from single muscle fibers", European Biophysics Journal, 1989, vol. 17, pp. 69-74.
PCT International Search Report and Written Opinion for Application No. PCT/US2007/062465 dated Aug. 8, 2007.
Pythila John W. et al., "Rapid, depth-resolved light scattering measurements using Fourier domain, angle-resolved low coherence interferometry", Optics Society of America, 2004.
Pyhtila John W. et al., "Determining nuclear morphology using an improved angle-resolved low coherence interferometry system", Optics Express, Dec. 15, 2003, vol. 11, No. 25, pp. 3473-3484.
Desjardins A.E., et al., "Speckle reduction in OCT using massively-parallel detection and frequency-domain ranging", Optics Express, May 15, 2006, vol. 14, No. 11, pp. 4736-4745.
Nadkarni, Seemantini K., et al., "Measurement of fibrous cap thickness in atherosclerotic plaques by spatiotemporal analysis of laser speckle images", Journal of Biomedical Optics, vol. 11 Mar./Apr. 2006, pp. 021006-1-021006-8.
PCT International Search Report and Written Opinion for Application No. PCT/US2007/066017 dated Aug. 30, 2007.
Yamanari M. et al., "Polarization sensitive Fourier domain optical coherence tomography with continuous polarization modulation", Proc. of SPIE, vol. 6079, 2006.
Zhang Jun et al., "Full range polarization-sensitive Fourier domain optical coherence tomography", Optics Express, Nov. 29, 2004, vol. 12, No. 24, pp. 6033-6039.
European Patent Office Search report for Application No. 01991092.6-2305 dated Jan. 12, 2006.
PCT International Search Report and Written Opinion for Application No. PCT/US2007/060670 dated Sep. 21, 2007.
J. M. Schmitt et al., (1999) "Speckle in Optical Coherence Tomography: An Overview", SPIE vol. 3726, pp. 450-461.
Office Action dated Oct. 11, 2007 for U.S. Appl. No. 11/534,095.
Office Action dated Oct. 9, 2007 for U.S. Appl. No. 09/709,162.
Notice of Allowance dated Oct. 3, 2007 for U.S. Appl. No. 11/225,840.
Siavash Yazdanfar et al., "In Vivo imaging in blood flow in human retinal vessels using color Doppler optical coherence tomography", SPIE, 1999 vol. 3598, pp. 177-184.
Office Action dated Oct. 30, 2007 for U.S. Appl. No. 11/670,069.
Tang C. L. et al., "Wide-band electro-optical tuning of semiconductor lasers", Applied Physics Letters, vol. 30, No. 2, Jan. 15, 1977, pp. 113-116.
Tang C. L. et al., "Transient effects in wavelength-modulated dye lasers", Applied Physics Letters, vol. 26, No. 9, May 1, 1975, pp. 534-537.
Telle M. John, et al., "Very rapid tuning of cw dye laser", Applied Physics Letters, vol. 26, No. 10, May 15, 1975, pp. 572-574.
Telle M. John, et al., "New method for electro-optical tuning of tunable lasers", Applied Physics Letters, vol. 24, No. 2, Jan. 15, 1974, pp. 85-87.
Schmitt M. Joseph et al. "OCT elastography: imaging microscopic deformation and strain of tissue", Optics Express, vol. 3, No. 6, Sep. 14, 1998, pp. 199-211.

M. Gualini Muddassir et al., "Recent Advancements of Optical Interferometry Applied to Medicine", IEEE Transactions on Medical Imaging, vol. 23, No. 2, Feb. 2004, pp. 205-212.

Maurice L. Roch et al. "Noninvasive Vascular Elastography: Theoretical Framework", IEEE Transactions on Medical Imaging, vol. 23, No. 2, Feb. 2004, pp. 164-180.

Kirkpatrick J. Sean et al. "Optical Assessment of Tissue Mechanical Properties", Proceedings of the SPIE—The International Society for Optical Engineering SPIE—vol. 4001, 2000, pp. 92-101.

Lisauskas B. Jennifer et al., "Investigation of Plaque Biomechanics from Intravascular Ultrasound Images using Finite Element Modeling", Proceedings of the 19th International Conference—IEEE Oct. 30-Nov. 2, 1997, pp. 887-888.

Parker K. J. et al., "Techniques for Elastic Imaging: A Review", IEEE Engineering in Medicine and Biology, Nov./Dec. 1996, pp. 52-59.

European Patent Office Search Report dated Nov. 20, 2007 for European Application No. 05791226.3.

Dubois Arnaud et al., "Ultrahigh-resolution OCT using white-light interference microscopy", Proceedings of SPIE, 2003, vol. 4956, pp. 14-21.

Office Action dated Jan. 3, 2008 for U.S. Appl. No. 10/997,789.
Office Action dated Dec. 21, 2007 for U.S. Appl. No. 11/264,655.
Office Action dated Dec. 18, 2007 for U.S. Appl. No. 11/288,994.
Office Action dated Jan. 10, 2008 for U.S. Appl. No. 11/435,228.
Office Action dated Jan. 10, 2008 for U.S. Appl. No. 11/410,937.
Office Action dated Jan. 11, 2008 for U.S. Appl. No. 11/445,990.
Office Action dated Feb. 4, 2008 for U.S. Appl. No. 10/861,179.
PCT International Search Report and Written Opinion for Application No. PCT/US2007/061463 dated Jan. 23, 2008.
PCT International Search Report and Written Opinion for Application No. PCT/US2007/061481 dated Mar. 17, 2008.
PCT International Search Report and Written Opinion for Application No. PCT/US2007/078254 dated Mar. 28, 2008.

Sadhwani, Ajay et al., "Determination of Teflon thickness with laser speckle I. Potential for burn depth diagnosis", Optical Society of America, 1996, vol. 35, No. 28, pp. 5727-5735.

C.J. Stewart et al., "A comparison of two laser-based methods for determination of burn scar perfusion: Laser Doppler versus laser speckle imaging", Elsevier Ltd., 2005, vol. 31, pp. 744-752.

G. J. Tearney et al., "Atherosclerotic plaque characterization by spatial and temporal speckle pattern analysis", CLEO 2001, vol. 56, pp. 307-307.

PCT International Search Report for Application No. PCT/US2007/068233 dated Feb. 21, 2008.

PCT International Search Report for Application No. PCT/US2007/060787 dated Mar. 18, 2008.

Statement under Article 19 and Reply to PCT Written Opinion for PCT International Application No. PCT/US2005/043951 dated Jun. 6, 2006.

PCT International Preliminary Report on Patentability for Application No. PCT/US2005/043951 dated Jun. 7, 2007.

R. Haggitt et al., "Barrett's Esophagus Correlation Between Mucin Histochemistry, Flow Cytomerty, and Histological Diagnosis for Predicting Increased Cancer Risk," Apr. 1988, American Journal of Pathology, vol. 131, No. 1, pp. 53-61.

R.H. Hardwick et al., (1995) "c-erbB-2 Overexpression in the Dysplasia/Carcinoma Sequence of Barrett's Oesophagus," Journal of Clinical Pathology, vol. 48, No. 2, pp. 129-132.

W. Polkowski et al, (1998) Clinical Decision making in Barrett's Oesophagus can be supported by Computerized Immunoquantitation and Morphometry of Features Associated with Proliferation and Differentiation, Journal of pathology, vol. 184, pp. 161-168.

J.R. Turner et al., MN Antigen Expression in Normal Preneoplastic and Neoplastic Esophagus: A Clinicopathological Study of a New Cancer-Associated Biomaker,: Jun. 1997, Human Pathology, vol. 28, No. 6, pp. 740-744.

D.J. Bowery et al., (1999) "Patterns of Gastritis in Patients with Gastro-Oesophageal Reflux Disease,", Gut, vol. 45, pp. 798-803.

O'Reich et al., (2000) "Expression of Oestrogen and Progesterone Receptors in Low-Grade Endometrial Stromal Sarcomas,", British Journal of Cancer, vol. 82, No. 5, pp. 1030-1034.

M.I. Canto et al., (1999) "Vital Staining and Barrett's Esophagus," Gastrointestinal Endoscopy, vol. 49, No. 3, Part 2, pp. S12-S16.

S. Jackle et al., (2000) "In Vivo Endoscopic Optical Coherence Tomography of the Human Gastrointestinal Tract-Toward Optical Biopsy," Encoscopy, vol. 32, No. 10, pp. 743-749.

E. Montgomery et al., "Reproducibility of the Diagnosis of Dysplasia in Barrett Esophagus: A Reaffirmation," Apr. 2001, Human Pathology, vol. 32, No. 4, pp. 368-378.

H. Geddert et al. "Expression of Cyclin B1 in the Metaplasia-Dysphasia-Carcinoma Sequence of Barrett Esophagus," Jan. 2002, Cancer, vol. 94, No. 1, pp. 212-218.

P. Pfau et al., (2003) "Criteria for the Diagnosis of Dysphasia by Endoscopic Optical Coherence Tomography," Gastrointestinal Endoscopy, vol. 58, No. 2, pp. 196-2002.

R. Kiesslich at al., (2004) "Confocal Laser Endoscopy for Diagnosing Intraepithelial Neoplasias and Colorectal Cancer in Vivo," Gastroenterology, vol. 127, No. 3, pp. 706-713.

X. Qi et al., (2004) "Computer Aided Diagnosis of Dysphasia in Barrett's Esophagus Using Endoscopic Optical Coherence Tomography," SPIE, Coherence Domain Optical Methods and Optical Coherence Tomography in Biomedicine VIII. Proc. of Conference on., vol. 5316, pp. 33-40.

Seltzer et al., (1991) "160 nm Continuous Tuning of a MQW Laser in an External Cavity Across the Entire 1.3 μm Communications Window," Electronics Letters, vol. 27, pp. 95-96.

Office Action dated Jan. 25, 2010 for U.S. Appl. No. 11/537,048.
International Search Report dated Jan. 27, 2010 for PCT/US2009/050553.
International Search Report dated Jan. 27, 2010 for PCT/US2009/047988.
International Search Report dated Feb. 23, 2010 for U.S. Appl. No. 11/445,131.
Office Action dated Mar. 18, 2010 of U.S. Appl. No. 11/844,454.
Office Action dated Apr. 8, 2010 of U.S. Appl. No. 11/414,564.
Japanese Office Action dated Apr. 13, 2010 for Japanese Patent application No. 2007-515029.
International Search Report dated May 27, 2010 for PCT/US2009/063420.
Office Action dated May 28, 2010 for U.S. Appl. No. 12/015,642.
Office Action dated Jun. 2, 2010 for U.S. Appl. No. 12/112,205.
Office Action dated Jul. 7, 2010 for U.S. Appl. No. 11/624,277.
Montag Ethan D., "Parts of the Eye" online textbook for JIMG 774: Vision & Psychophysics, download on Jun. 23, 2010 from http://www.cis.rit.edu/people/faculty/montag/vandplite/pages/chap_8/ch8p3.html.
Office Action dated Jul. 16, 2010 for U.S. Appl. No. 11/445,990.
Office Action dated Jul. 20, 2010 for U.S. Appl. No. 11/625,135.
Office Action dated Aug. 5, 2010 for U.S. Appl. No. 11/623,852.
Chinese office action dated Aug. 4, 2010 for CN 200780005949.9.
Chinese office action dated Aug. 4, 2010 for CN 200780016266.3.
Zhang et al., "Full Range Polarization-Sensitive Fourier Domain Optical Coherence Tomography" Optics Express, Nov. 29, 2004, vol. 12, No. 24.
Office Action dated Aug. 27, 2010 for U.S. Appl. No. 11/569,790.
Office Action dated Aug. 31, 2010 for U.S. Appl. No. 11/677,278.
Office Action dated Sep. 3, 2010 for U.S. Appl. No. 12/139,314.
Yong Zhao et al: "Virtual Data Grid Middleware Services for Data-Intensive Science", Concurrency and Computation: Practice and Experience, Wiley, London, GB, Jan. 1, 2000, pp. 1-7, pp. 1532-0626.
Swan et al., "Toward Nanometer-Scale Resolution in Fluorescence Microscopy using Spectral Self-Inteference" IEEE Journal. Selected Topics in Quantum Electronics 9 (2) 2003, pp. 294-300.
Moisccv et al., "Spectral Self-Interfence Fluorescence Microscopy", J. Appl. Phys. 96 (9) 2004, pp. 5311-5315.
Hendrik Verschuerenc, "Interference Reflection Microscopy in Cell Biology", J. Cell Sci. 75, 1985, pp. 289-301.
Park et al., "Diffraction Phase and Fluorescence Microscopy", Opt. Expr. 14 (18) 2006, pp. 8263-8268.
Swan et al., "High Resolution Spectral Self-Interference Fluorescence Microscopy", Proc. SPIE 4621, 2002, pp. 77-85.
Sanchez et al., "Near-Field Fluorscence Microscopy Based on Two-Photon Excvitation with Metal Tips", Phys. Rev. Lett. 82 (20) 1999, pp. 4014-4017.

Wojtkowski, Maciej, Ph.D. "Three-Dimensional Retinal Imaging with High-Speed Ultrahigh-Resolution Optical Coherence Tomography" Opthalmology, Oct. 2005, 112(10): 1734-1746.
Vaughan, J.M. et al., "Brillouin Scattering, Density and Elastic Properties of the Lens and Cornea of the Eye", Nature, vol. 284, Apr. 3, 1980, pp. 489-491.
Hess, S.T. et al. "Ultra-high Resolution Imaging by Fluorecence Photoactivation Localization Microscopy" Biophysical Journal vol. 91, Dec. 2006, 4258-4272.
Fernandez-Suarez, M. et al., "Fluorescent Probes for Super-Resolution Imaging in Living Cells" Nature Reviews Molecular Cell Biology vol. 9, Dec. 2008.
Extended European Search Report mailed Dec. 14, 2010 for EP 10182301.1.
S. Hell et al., "Breaking the diffraction resolution limit by stimulated-emission-simulated-emission-depletion fluorescence microscopy," Optics Letters. 19:495 (1995) and Ground State Depletion (GSD).
S. Hell et al. "Ground-State-Depletion fluorescence miscroscopy—a concept for breaking the diffraction resolution limit," Appled Physics B. 60:780 (1994)) fluorescence microscopy, photo-activated localization miscroscopy (PALM).
E. Betzig et al. "Imaging intracellular fluorescent proteins at nanometer resolution," Science 313:1642 (2006), stochastic optical reconstruction microscopy (STORM).
M. Rust et al. "Sub-diffraction-limited imaging by stochastic optical reconstruction microscopy (STORM)," Nature Methods 3:783 (2006), and structed illumination microscopy (SIM).
B. Bailey et al. "Enhancement of Axial Resolution in Fluorescence Microscopy by Standing-Wave Excitation," Nature 366:44 (1993).
M. Gustafsson "Surpassing the lateral resolution limit by a factor of two using structured illumination microscopy," Journal of Miscroscopy 198:82 (2000).
M. Gustafsson "Nonlinear structured ilumination microscopy: Widefield fluorescence imaging with theoretically unlimited resolutions," PNAS 102:13081 (2005)).
R. Thompson et al. "Precise nanometer localization analysis for individual fluorescent probes," Biophysical Journal 82:2775 (2002).
K. Drabe et al. "Localization of Spontaneous Emission in front of a mirror," Optics Communications 73:91 (1989).
Swan et al. "Toward nanometer-scale resolution in fluorecence microscopy using spectral self-interference," IEEE Quantum Electronics 9:294 (2003).
C. Joo, et al. "Spectral Domain optical coherence phase and multiphoton microscopy," Optics Letters 32:623 (2007).
Virmani et al., "Lesions from sudden coronary death: A comprehensive morphological classification scheme for atherosclerotic lesions," Arterioscler. Thromb. Vase. Bio., 20:1262-75 (2000).
Gonzalez, R.C. and Wintz, P., "Digital Image Processing" Addison-Wesley Publishing Company, Reading MA, 1987.
V. Tuchin et al., "Speckle interferometry in the measurements ofbiotissues vibrations," SPIE, 1647: 125 (1992).
A.A. Bednov et al., "Investigation of Statistical Properties of Lymph Flow Dynamics Using Speckle-Microscopy," SPIE, 2981: 181-90 (1997).
Feng et al., "Mesoscopic Conductors and Correlations in Laser Speckle Patters" Science, New Series, vol. 251, No. 4994, pp. 633-639 (Feb. 8, 1991).
Lee et al., "The Unstable Atheroma," Arteriosclerosis, Thrombosis & Vascular Biology, 17:1859-67 (1997).
International Search report dated Apr. 29, 2011 for PCT/US2010/051715.
International Search report dated Sep. 13, 2010 for PCT/US2010/023215.
International Search Report dated Jul. 28, 2011 for PCT/US2010/059534.
International Search Report dated Nov. 18, 2011 for PCT/US2011/027450.
International Search Report dated Nov. 18, 2011 for PCT/US2011/027437.
International Search report dated Nov. 22, 2011 for PCT/US2011/027421.
Liptak David C. et al., (2007) "On the Development of a Confocal Rayleigh-Brillouin Microscope" American Institute of Physics vol. 78, 016106.
Office Action mailed Oct. 1, 2008 for U.S. Appl. No. 11/955,986.
Invitation of Pay Additional Fees mailed Aug. 7, 2008 for International Application No. PCT/US2008/062354.
Invitation of Pay Additional Fees mailed Jul. 20, 2008 for International Application No. PCT/US2007/081982.
International Search Report and Written Opinion mailed Mar. 7, 2006 for PCT/US2005/035711.
International Search Report and Written Opinion mailed Jul. 18, 2008 for PCT/US2008/057533.
Aizu, Y et al. (1991) "Bio-Speckle Phenomena and Their Application to the Evaluation of Blood Flow" Optics and Laser Technology, vol. 23, No. 4, Aug. 1, 1991.
Richards G.J. et al. (1997) "Laser Speckle Contrast Analysis (LASCA): A Technique for Measuring Capillary Blood Flow Using the First Order Statistics of Laser Speckle Patterns" Apr. 2, 1997.
Gonick, Maria M., et al (2002) "Visualization of Blood Microcirculation Parameters in Human Tissues by Time Integrated Dynamic Speckles Analysis" vol. 972, No. 1, Oct. 1, 2002.
International Search Report and Written Opinion mailed Jul. 4, 2008 for PCT/US2008/051432.
Jonathan, Enock (2005) "Dual Reference Arm Low-Coherence Interferometer-Based Reflectometer for Optical Coherence Tomography (OCT) Application" Optics Communications vol. 252.
Motaghian Nezam, S.M.R. (2007) "increased Ranging Depth in optical Frequency Domain Imaging by Frequency Encoding" Optics Letters, vol. 32, No. 19, Oct. 1, 2007.
Office Action dated Jun. 30, 2008 for U.S. Appl. No. 11/670,058.
Office Action dated Jul. 7, 2008 for U.S. Appl. No. 10/551,735.
Australian Examiner's Report mailed May 27, 2008 for Australian patent application No. 2003210669.
Notice of Allowance mailed Jun. 4, 2008 for U.S. Appl. No. 11/174,425.
European communication dated May 15, 2008 for European patent application No. 05819917.5.
International Search Report and Written Opinion mailed Jun. 10, 2008 for PCT/US2008/051335.
Oh. W.Y. et al (2006) "Ultrahigh-Speed Optical Frequency Domain Imaging and Application to laser Ablation Monitoring" Applied Physics Letters, vol. 88.
Office Action dated Aug. 21, 2008 for U.S. Appl. No. 11/505,700.
Sticker, Markus (2002) En Face Imaging of Single Cell layers by Differential Phase-Contrast Optical Coherence Microscopy) Optics Letters, col. 27, No. 13, Jul. 1, 2002.
International Search Report and Written Opinion dated Jul. 17, 2008 for International Application No. PCT/US2008/057450.
International Search Report and Written Opinion dated Aug. 11, 2008 for International Application No. PCT/US2008/058703.
US National Library of Medicine (NLM), Bethesda, MD, US; Oct. 2007, "Abstracts of the 19th Annual Symposium of Transcatheter Cardiovascular Therapeutics, Oct. 20-25, 2007, Washington, DC, USA."
International Search Report and Written Opinion dated May 26, 2008 for International Application No. PCT/US2008/051404.
Office Action dated Aug. 25, 2008 for U.S. Appl. No. 11/264,655.
Office Action dated Sep. 11, 2008 for U.S. Appl. No. 11/624,334.
Office Action dated Aug. 21, 2008 for U.S. Appl. No. 11/956,079.
Gelikono, V. M. et al. Oct. 1, 2004 "Two-Wavelength Optical Coherence Tomography" Radio physics and Quantum Electronics, Kluwer Academic Publishers-Consultants. vol. 47, No. 10-1.
International Search Report and Written Opinion for PCT/US2007/081982 dated Oct. 19, 2007.
Database Compendex Engineering Information, Inc., New York, NY, US; Mar. 5, 2007, Yelin, Dvir et al: "Spectral-Domain Spectrally-Encoded Endoscopy".
Database Biosis Biosciences Information Service, Philadelphia, PA, US; Oct. 2006, Yelin D. et al: "Three-Dimensional Miniature Endoscopy".
International Search Report and Written Opinion mailed Mar. 14, 2005 for PCT/US2004/018045.

Notification of the international Preliminary Report on Patentability mailed Oct. 21, 2005.
Shim M.G. et al., "Study of Fiber-Optic Probes for In vivo Medical Raman Spectroscopy" Applied Spectroscopy. vol. 53, No. 6, Jun. 1999.
Bingid U. et al., "Fibre-Optic Laser-Assisted Infrared Tumour Diagnostics (FLAIR); Infrared Tomour Diagnostics" Journal of Physics D. Applied Physics, vol. 38, No. 15, Aug. 7, 2005.
Jun Zhang et al. "Full Range Polarization-Sensitive Fourier Domain Optical Coherence Tomography" Optics Express, vol. 12, No. 24. Nov. 29, 2004.
Yonghua et al., "Real-Time Phase-Resolved Functional Optical Hilbert Transformation" Optics Letters, vol. 27, No. 2, Jan. 15, 2002.
Siavash et al., "Self-Referenced Doppler Optical Coherence Tomography" Optics Letters, vol. 27, No. 23, Dec. 1, 2002.
International Search Report and Written Opinion dated Dec. 20, 2004 for PCT/US04/10152.
Notification Concerning Transmittal of International Preliminary Report on Patentability dated Oct. 13, 2005 for PCT/US04/10152.
International Search Report and Written Opinion dated Mar. 23, 2006 for PCT/US2005/042408.
International Preliminary Report on Patentability dated Jun. 7, 2007 for PCT/US2005/042408.
International Search Report and Written Opinion dated Feb. 28, 2007 for International Application No. PCT/US2006/038277.
International Search Report and Written Opinion dated Jan. 30, 2009 for International Application No. PCT/US2008/081834.
Fox, J.A. et al; "A New Galvanometric Scanner for Rapid tuning of C02 Lasers" New York, IEEE, US vol. Apr. 7, 1991.
Motaghian Nezam, S.M. et al: "High-speed Wavelength-Swept Semiconductor laser using a Diffrection Grating and a Polygon Scanner in Littro Configuration" *Optical Fiber Communication and the National Fiber Optic Engineers Conference* Mar. 29, 2007.
International Search Report and Written Opinion dated Feb. 2, 2009 for International Application No. PCT/US2008/071786.
Bilenca A et al: "The Role of Amplitude and phase in Fluorescence Coherence Imaging: From Wide Filed to Nanometer Depth Profiling", *Optics IEEE*, May 5, 2007.
Inoue, Yusuke et al: "Varible Phase-Contrast Fluorescence Spectrometry for Fluorescently Strained Cells", *Applied Physics Letters*, Sep. 18, 2006.
Bernet, S et al: "Quantitative Imaging of Complex Samples by Spiral Phase Contrast Microscopy", *Optics Express*, May 9, 2006.
International Search Report and Written Opinion dated Jan. 15, 2009 for International Application No. PCT/US2008/074863.
Office Action dated Feb. 17, 2009 for U.S. Appl. No. 11/211,483.
Notice of Reasons for Rejection mailed Dec. 2, 2008 for Japanese patent application No. 2000-533782.
International Search Report and Written Opinion dated Feb. 24, 2009 for PCT/US2008/076447.
European Official Action dated Dec. 2, 2008 for EP 07718117.0.
Barfuss et al (1989) "Modified Optical Frequency Domain Reflectometry with High spatial Resolution for Components of integrated optic Systems", Journal of Lightwave Technology, IEEE vol. 7., No. 1.
Yun et al., (2004) "Removing the Depth-Degeneracy in Optical Frequency Domain Imaging with Frequency Shifting", Optics Express, vol. 12, No. 20.

International Search Report and Written Opinion dated Jun. 10, 2009 for PCT/US08/075456.
European Search Report issued May 5, 2009 for European Application No. 01991471.2.
Motz, J.T. et al: "Spectral-and Frequency-Encoded Fluorescence Imaging" Optics Letters, OSA, Optical Society of America, Washington, DC, US, vol. 30, No. 20, Oct. 15, 2005, pp. 2760-2762.
Japanese Notice of Reasons for Rejection dated Jul. 14, 2009 for Japanese Patent application No. 2006-503161.
Office Action dated Aug. 18, 2009 for U.S. Appl. No. 12/277,178.
Office Action dated Aug. 13, 2009 for U.S. Appl. No. 10/136,813.
Office Action dated Aug. 6, 2009 for U.S. Appl. No. 11/624,455.
Office Action dated May 15, 2009 for U.S. Appl. No. 11/537,123.
Office Action dated Apr. 17, 2009 for U.S. Appl. No. 11/537,343.
Office Action dated Apr. 15, 2009 for U.S. Appl. No. 12/205,775.
Office Action dated Dec. 9, 2008 for U.S. Appl. No. 09/709,162.
Office Action dated Dec. 23, 2008 for U.S. Appl. No. 11/780,261.
Office Action dated Jan. 9, 2010 for U.S. Appl. No. 11/624,455.
Office Action dated Feb. 18, 2009 for U.S. Appl. No. 11/285,301.
Beddow et al, (May 2002) "Improved Performance Interferomater Designs for Optical Coherence Tomography", IEEE Optical Fiber Sensors Conference, pp. 527-530.
Yacioob et al., (Jun. 2002) "High-Speed Wavelength-Multiplexed Fiber-Optic Sensors for Biomedicine," Sensors Proceedings of the IEEE, pp. 325-330.
Office Action dated Feb. 18, 2009 for U.S. Appl. No. 11/697,012.
Zhang et al, (Sep. 2004), "Fourier Domain Functional Optical Coherence Tomography", Saratov Fall Meeting 2004, pp. 8-14.
Office Action dated Feb. 23, 2009 for U.S. Appl. No. 11/956,129.
Office Action dated Mar. 16, 2009 for U.S. Appl. No. 11/621,694.
Office Action dated Oct. 1, 2009 for U.S. Appl. No. 11/677,278.
Office Action dated Oct. 6, 2009 for U.S. Appl. No. 12/015,642.
Lin, Stollen et al., (1977) "A CW Tunable Near-infrared (1.085-1.175-um) Raman Oscillator," Optics Letters, vol. 1, 96.
Summons to attend Oral Proceedings dated Oct. 9, 2009 for European patent application No. 06813365.1.
Office Action dated Dec. 15, 2009 for U.S. Appl. No. 11/549,397.
Ponesos er al: "Optical Coherence Tomography of the Biliary Tree During ERCP", Gastrointestinal Endoscopy, Elsevier, NL, vol. 55, No. 1, Jan. 1, 2002, pp. 84-88.
Fu L e tal: double-Clad Photon Crystal Fiber Coupler for compact Nonlinear Optical Microscopy Imaging, Optics Letters, OSA, Optical Society of America, vol. 31, No. 10, May 15, 2006, pp. 1471-1473.
Japanese language Appeal Decision dated Jan. 10, 2012 for JP 2006-503161.
Japanese Notice of Grounds for Rejection dated Oct. 28, 2011 for JP2009-294737.
Japanese Notice of Grounds for Rejection dated Dec. 28, 2011 for JP2008-535793.
Japanese Notice of Reasons for Rejection dated Dec. 12, 2011 for JP 2008-533712.
International Search Report and Written Opinion mailed Feb. 9, 2012 based on PCT/US2011/034810.

* cited by examiner

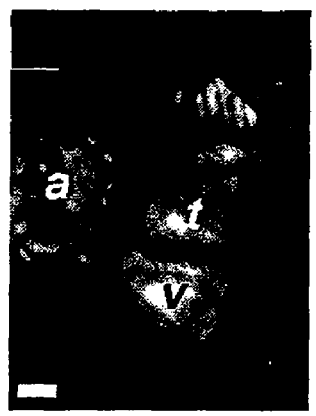
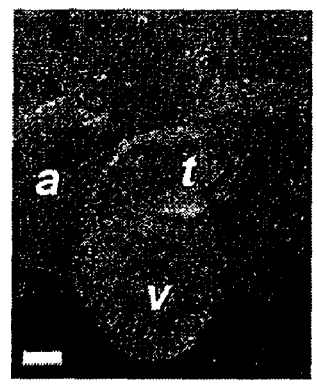
FIG.15g  FIG.15h
FIG.15i  FIG.15j
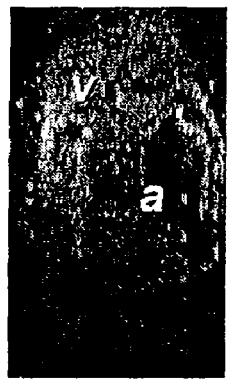
FIG.15k  FIG.15l  FIG.15m

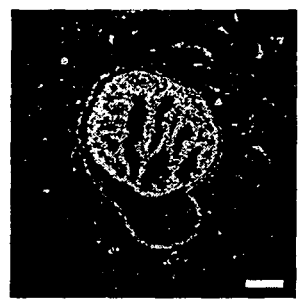
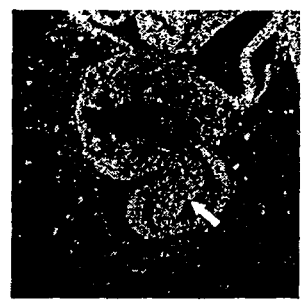
FIG.16a  FIG.16b
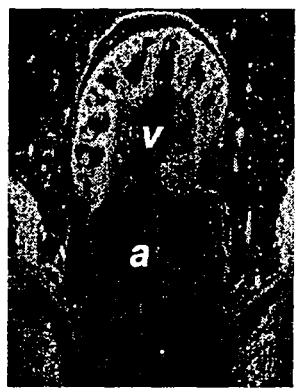
FIG.16c  FIG.16d
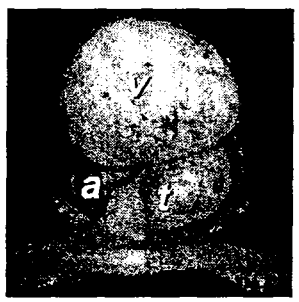
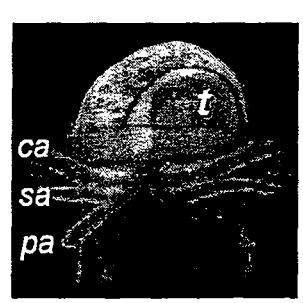
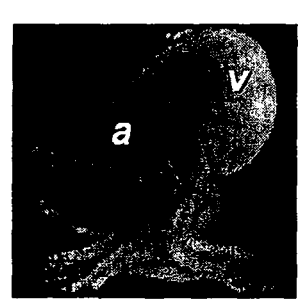
FIG.16e  FIG.16f  FIG.16g

ARRANGEMENTS AND METHODS FOR PROVIDING MULTIMODALITY MICROSCOPIC IMAGING OF ONE OR MORE BIOLOGICAL STRUCTURES

CROSS-REFERENCE TO RELATED APPLICATION(S)

This application is a divisional application of, and therefore claims priority from, U.S. application Ser. No. 11/537,343, filed on Sep. 29, 2006, which is based upon and claims the benefit of priority from U.S. patent application Ser. No. 60/721,802, filed Sep. 29, 2005. The entire disclosures of both applications are incorporated herein by reference.

FIELD OF THE INVENTION

The present invention generally relates to arrangements and methods for providing multimodality microscopic imaging of one or more biological structures, and particularly to, e.g., conducting reflectance and/or fluorescence microscopy of biological specimens using spectrally encoded confocal microscopy ("SECM"), fluorescence SECM, optical coherence tomography ("OCT"), spectral domain ("SD")-OCT, optical frequency domain interferometry ("OFDI"), and optical coherence microscopy ("OCM") procedures.

BACKGROUND OF THE INVENTION

A determination of the relationship between the molecular basis of genetic alterations and phenotype generally utilizes accurate two- and three-dimensional characterization of microstructure of biological specimens. However, motion and small dimensions make many living biological specimens can be more difficult to evaluate.

Optical techniques offer the potential to image the biological specimens at a high resolution. For certain applications, optical imaging based on endogenous contrast can be advantageous over techniques that require exogenous agents, since such beneficial procedures can allow the analysis of the specimen in its native state and at multiple time points, with a small amount of preparation. As an example, several endogenous-contrast imaging modalities are described herein for visualizing embryonic heart microstructure: two exemplary forms of optical coherence tomography ("OCT") as described in D. Huang et al., "Optical coherence tomography," *Science* 254, pp. 1178-1181 (1991), time-domain optical coherence tomography ("TD-OCT") as described in S. A. Boppart et al., "Investigation of developing embryonic morphology using optical coherence tomography," *Dev Biol* 177, pp. 54-63 (1996), and optical frequency domain imaging ("OFDI") as described in M. A. Choma et al., "Sensitivity advantage of swept source and Fourier domain optical coherence tomography," *Optics Express* 11, pp. 2183-2189 (2003); and S. H. Yun et al., "High-speed optical frequency-domain imaging," *Optics Express* 11, pp 2953-2963 (2003).

Additional examples can be provided and utilized including two reflectance microscopy techniques, e.g., full-field optical coherence microscopy ("FFOCM") as described in E. Beaurepaire et al., "Full-field optical coherence microscopy," *Optics Letters* 23, pp. 244-246 (1998); A. Dubois et al., "Ultrahigh-resolution full-field optical coherence tomography," *Appl Opt* 43, pp. 2874-2883 (2004); and G. Moneron et al., "Stroboscopic ultrahigh-resolution full-field optical coherence tomography," *Opt Lett* 30, pp. 1351-1353 (2005), and spectrally encoded confocal microscopy ("SECM") as described in G. J. Tearney et al., "Spectrally encoded confocal microscopy," *Optics Letters* 23, pp. 1152-1154 (1998); and C. Boudoux et al., "Rapid wavelength-swept spectrally encoded confocal microscopy," *Optics Express* 13, pp. 8214-8221 (2005).

For example, the TDOCT techniques can use low-coherence interferometry to obtain cross-sectional images with ~10 μm resolution and at depths of up to 2 mm. (See S. A. Boppart et al., "Noninvasive assessment of the developing Xenopus cardiovascular system using optical coherence tomography," *Proc Natl Acad Sci USA* 94, pp. 4256-4261 (1997); S. Yazdanfar et al., "High resolution imaging of in vivo cardiac dynamics using color Doppler optical coherence tomography," *Optics Express* 1, pp. 424-431 (1997); T. M. Yelbuz et al., "Optical coherence tomography: a new high-resolution imaging technology to study cardiac development in chick embryos," *Circulation* 106, pp. 2771-2774 (2002); V. X. D. Yang et al., "High speed, wide velocity dynamic range Doppler optical coherence tomography (Part II): Imaging in vivo cardiac dynamics of Xenopus laevis," *Optics Express* 11, pp. 1650-1658 (2003); and W. Luo et al., "Three-dimensional optical coherence tomography of the embryonic murine cardiovascular system" *Journal of biomedical optics* 11, 021014 (2006).

The exemplary OFDI technique can be considered as a derivative of the TDOCT techniques that may enable an acquisition of images at significantly higher frame rates as described in R. Huber et al., "Three-dimensional and C-mode OCT imaging with a compact, frequency swept laser source at 1300 nm," *Optics Express* 13, pp. 10523-10538 (2005). The high speed of the OFDI techniques can enable an implementation of a true four-dimensional (4D) microscopy (e.g., three-dimensional microscopy as a function of time). Full-field optical coherence microscopy ("FFOCM") techniques can utilize low-coherence interferometry and higher numerical aperture objective lenses to attain resolution at the sub-cellular level in all three dimensions. Such FFOCM techniques are likely considerably slower than the OFDI techniques. The exemplary SECM techniques can have a form of the reflectance confocal microscopy using which it may be possible to obtain two-dimensional images with micron-level resolution, at significantly higher speeds than possibly obtained using the FFOCM techniques.

While each of these natural-contrast procedures can individually be used for imaging a microstructure of the embryonic heart, when combined, these procedures can provide a powerful set of tools for two-, three-, and four-dimensional characterization of early myocardial morphology and dynamics. A combination of these different modalities into one single microscopy device may have additional advantages such as, e.g., (a) a comparison of images in different formats, different resolutions, and fields of view, (b) a simultaneous acquisition of both structural and function information, and/or (c) these tasks can be accomplished using one instrument without requiring moving or altering the specimen.

OBJECTS AND SUMMARY OF THE INVENTION

One of the objects of the present invention is to overcome certain deficiencies and shortcomings of the prior art systems (including those described herein above), and provide exemplary embodiments of providing multimodality microscopic imaging of one or more biological structures. Such exemplary embodiments can conduct reflectance and/or fluorescence microscopy of biological specimens using spectrally encoded confocal microscopy ("SECM"), fluorescence SECM, optical coherence tomography ("OCT"), spectral domain ("SD")-OCT, optical frequency domain interferometry ("OFDI"), and optical coherence microscopy ("OCM") procedures.

For example, an analysis of biological specimens generally employs a visualization of its microstructure and functions, preferably with small alterations to the specimen. According to one exemplary embodiment of the present invention, a combination of multiple different imaging modalities can be provided in a single microscope device. Each exemplary technique according to certain exemplary embodiments of the present invention can provide distinct and complementary imaging capabilities, including high-speed (e.g., 1000 frames per second) and high axial resolution (4-16 μm) cross-sectional imaging in vivo, true four-dimensional imaging in vivo, three-dimensional microscopy with isotropic cellular (e.g., 1-2 μm) resolution in vitro, and two-dimensional subcellular imaging in vivo. When combined, these exemplary imaging modalities can effectuate a more complete picture of the morphologic and dynamics of biological specimens.

Thus, the exemplary embodiments of the present invention include arrangements and methods for acquiring multimodality microscopic data. For example, according to one exemplary embodiment, it is possible to use a combination of unique broad bandwidth or rapid wavelength swept sources and optics interposed between a scanning mechanism and an imaging lens. Data can be acquired simultaneously and/or serially, e.g., without moving the specimen. For example, data obtained from different modalities can be co-registered so that it can be displayed side-by-side and/or overlaid on top of each other. Quantitative information can be obtained from all of the datasets in a complementary manner.

Thus, in accordance with the exemplary embodiments of the present invention, method and apparatus can be provided. For example, first data associated with a first signal received from at least one region of at least one sample can be provided based on a first modality, and second data associated with a second signal received from the at least one sample can be provided based on a second modality which is different from the first modality. Third data associated with a reference can be received. Further data can be generated based on the first, second and third data. In addition, third data associated with a second signal received from the at least one sample can be obtained. Each of the third data can be based on a further modality which is different from the first modality and the second modality, and the further data can be further determined based on the third data. Further, the first modality can be a spectral-encoded modality, and the second modality can be a non-spectral-encoding modality.

In another exemplary embodiment of the present invention, the first modality can be florescence imaging. A microscope arrangement and/or a beam-scanning arrangement can be provided. The beam-scanning arrangement may be configured to forward electro-magnetic radiation to the at least region. Further, a two-dimensional image and/or a three-dimensional image can be produced as a function of the further data. The first and second data may be obtained substantially simultaneously. In addition, the first and second data may be associated with approximately the same location on the sample, and/or can be obtained using another one of the first and second data.

According to a further exemplary embodiment of the present invention, the apparatus can be provided in a probe and/or a single enclosure. It is also possible to obtain spectral encoding microscopy information using such exemplary apparatus and method, as well as bright field, dark field, phase contrast, polarization, epireflectance and/or reflectance microscopy information. It is further possible to use such exemplary apparatus and method change from the first modality to the second modality. Optical coherence tomography information associated with a signal provided by a source arrangement having a plurality of wavelengths can be obtained. A plurality of detectors can be provided to detect a spectral interference between the second and third signals as a function of the wavelengths.

Optical coherence tomography information associated with a signal provided by a source arrangement can be obtained whose wavelength varies over time. At least one image can be generated based on the first and second data. In addition, a first image can be generated based on the first data and a second image can be generated based on the second data. The first and second images may be associated with one another as a function of the first and second data. It is possible to obtain optical coherence tomography information and/or optical frequency domain interferometry information.

Other features and advantages of the present invention will become apparent upon reading the following detailed description of embodiments of the invention, when taken in conjunction with the appended claims.

BRIEF DESCRIPTION OF THE DRAWINGS

Further objects, features and advantages of the present invention will become apparent from the following detailed description taken in conjunction with the accompanying figures showing illustrative embodiments of the present invention, in which:

FIGS. 16a-16m are various exemplary three-dimensional images of Xenopus heart in vitro using exemplary embodiments of the FFOCM procedure.

Figure 1:
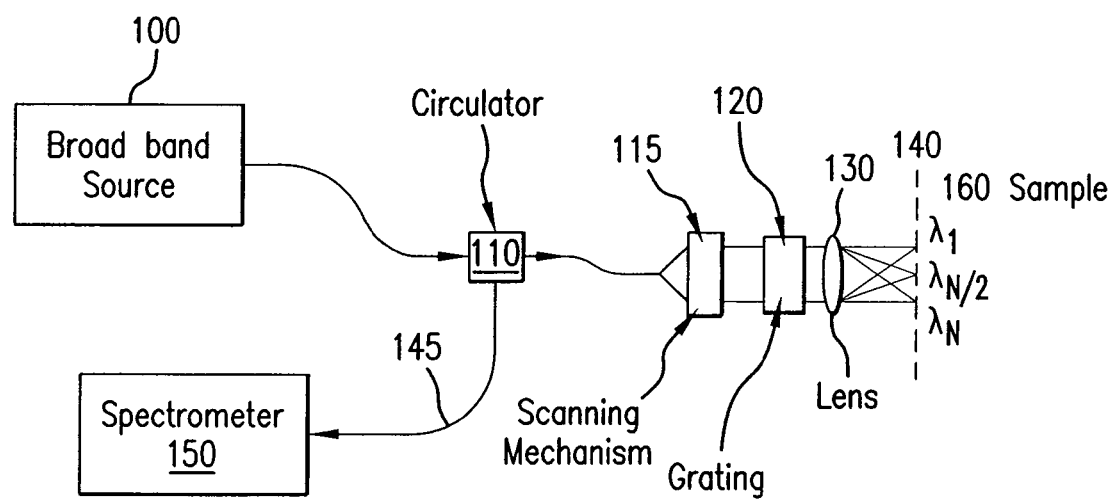
FIG. 1 is a schematic diagram of an exemplary SECM system that utilizes a broad bandwidth source.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF EXEMPLARY EMBODIMENTS

Exemplary SECM techniques are capable of providing subcellular level resolution images in tissue or biological specimens. SECM images can alternatively represent fluorescence from the sample or reflectance from the sample. FIG. 1 depicts a schematic diagram of an exemplary SECM arrangement which utilizes a broadband source. In this exemplary configuration, a quasimonochromatic or broadband light 100 illuminates a circulator 110, which alternatively may be a beam splitter. In one embodiment this circulator or beam splitter is fiber-optic coupled. The core of the optical fiber can serve as the pinhole for the confocal microscope system. The fiber may alternatively have multiple claddings that transmit light such that for example the light exciting the sample is single mode and the collected light is multimode. Light from this element may be incident on a scanning mechanism 115 that scans the angle of the beam so as to produce one or more transverse scans on the sample. The scanning mechanism may alternatively be one of a resonant scanner, galvanometer scanner, polygon scanning mirror, acousto-optic scanner or the like. A telescope apparatus may be used to image the scan axis to the back focal plane of the objective lens 130. Light from the scanning mechanism can then be directed towards a wavelength dispersing element 120 such as a transmission diffraction grating, prism, grating prism, dual prism grating prism (DP-GRISM) or the like. This exemplary element may disperse the different wavelengths in the broad bandwidth source so that it is incident on the objective lens 130 with varying angles that depend on wavelength.

In one exemplary embodiment, the lens can have a numerical aperture that may produce a small focused spot or alternatively the lens has a high NA>0.2. The objective lens 130 focuses each wavelength region onto the sample where each wavelength region on the sample 160 that can be located at a different spatial location. For a diffraction grating and an objective lens, these exemplary elements may form a wavelength encoded line 140 on the sample where each position on the line is encoded by a different wavelength region. Light from the sample 160 can be reflected back through the exemplary system of FIG. 1. Out-of-focus light may be rejected by the cladding of the optical fiber and in focus (e.g., confocal) light is transmitted back through the circulator/beam splitter 110 to a spectrometer that measures the spectral content of the returned light 145. Confocal remittance as a function of spatial location is decoded by measuring this spectrum, forming one line on an image. Successive lines are formed for each angular position of the scanning mechanism 115, forming a spectrally-encoded confocal microscopy image.

Figure 2:
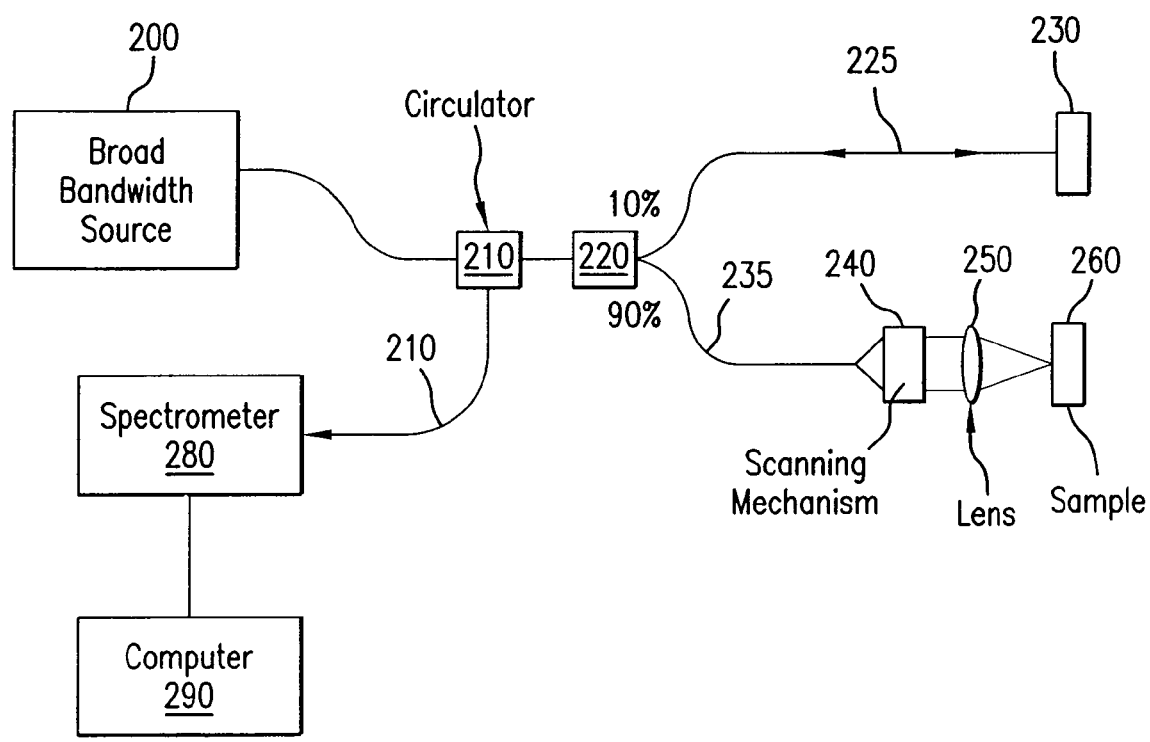
FIG. 2 is a schematic diagram of an exemplary SD-OCT system.

FIG. 2 depicts a schematic diagram of an exemplary spectral-domain OCT system. Contrary to the exemplary SECM system, the exemplary SD-OCT can provide cross-sectional images of a biological specimen by using coherence gating in the Fourier domain. SD-OCT images can typically have a lower resolution (~3-10 µm), and may have a larger field of view (several mm's). In this exemplary SD-OCT system, a broad bandwidth or quasimonochromatic source 200 can be input into an interferometer, which may be fiber optic-based. The fiber-coupled light can be transmitted to a circulator 210 and a beam splitter 220. When coupled into the circulator 210, the light can preferably be subsequently split by a beam splitter 220 so that a portion thereof can be transmitted to a reference arm 225 and a portion is transmitted to a sample arm 235. Light from the reference arm 225 can be reflected off a mirror 230 (e.g., a reference) to the beam splitter 220 or alternatively transmitted back to the beam splitter 220. In one exemplary embodiment, the splitter 220 can be configured so that the majority of light is transmitted to the sample arm 235. Light from the sample arm fiber can then be directed towards a lens and a scanning mechanism 240. The scanning mechanism can scan the light of the sample arm 235 in arbitrary one- or two-dimensional patterns. Light can be transmitted from the scanning mechanism to a lens 250 which, in one exemplary embodiment, can have a NA so that the confocal parameter is sufficiently large to allow cross-sectional imaging in the biological specimen or sample 260.

Light remitted from the sample may be transmitted back through the apparatus to the circulator/beam splitter 210, and directed to a spectrometer 280. The reflectance as a function of depth (A-line) within the tissue may be reconstructed by, e.g., a background subtraction, remapping λ-space to k-space, and inverse Fourier transformation of the spectral interference signal in a central processing unit or computer 290. Successive A-lines are obtained for each scanning mechanism position, thereby reconstructing a cross-sectional image of the sample. Alternative exemplary embodiments known in the art, including the capability to obtain spectral information from the sample by short-time-Fourier transformation ("STFT") of the spectral interference, Doppler-sensitive SD-OCT and polarization-sensitive SD-OCT, may be also utilized to extract additional information from the biological specimen, such as absorption, flow, and birefringence.

Figure 3:
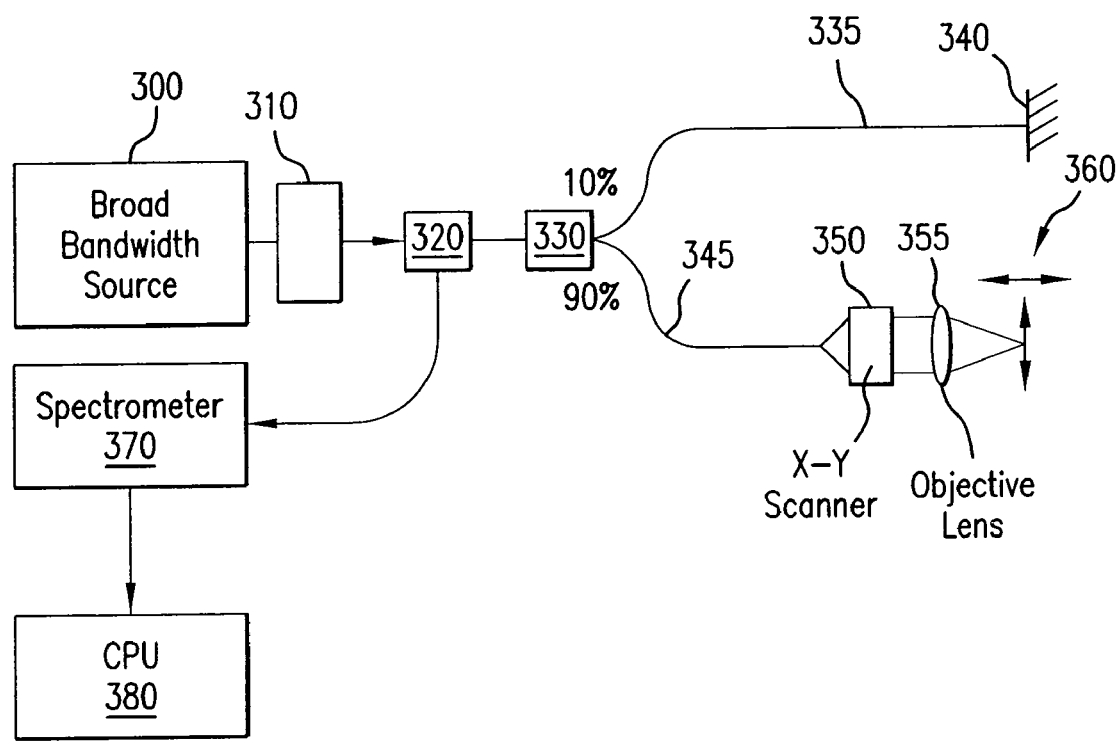
FIG. 3 is a schematic diagram of an exemplary OCM system that utilizes a broad bandwidth source.

FIG. 3 depicts a schematic diagram of an exemplary optical coherence microscopy ("OCM") system. The exemplary OCM system can utilize a combination of confocal microscopy and OCT techniques that may be advantageous, as the axial point spread functions of both such exemplary techniques may be multiplied so as to provide a greater degree of optical sectioning. In one exemplary embodiment of the OCM system, light from a broad bandwidth source can be input into a modulating element 310 so that the modulation frequency approximates that of the spectral interference in the interferometer. This exemplary modulation element may be one of a Michelson interferometer, pulse shaping apparatus, spectral filter, etc. The modulation may also shift the spectral phase by some amount over time so that successive spectra may be subtracted to extract only the spectral interference term. Following the modulating element, the light can be transmitted to a circulator/beam splitter 320 and then, if a circulator is used, to a beam splitter 330. Light can again be transmitted to a reference arm 335 and a sample arm 345. Light from the reference arm 335 is reflected by a mirror 340. Light from the sample arm 345 can be transmitted to an x-y scanner 350, which can alternatively be one of a or a combination of a resonant scanner, galvanometer scanner, polygon scanning mirror, acousto-optic scanner or the like.

Light from the scanner 350 can be directed to an objective lens 355 so that a tightly focused spot can be scanned within the sample. The objective lens or sample 360 may be alternatively scanned in any of three dimensions to facilitate data collection from different portions within the sample. Light is transmitted back from the sample 360 to the circulator/beam splitter 320 and subsequently to a detection apparatus. In one embodiment, the detector is a spectrometer and OCM data is obtained by obtaining A-lines from the sample in a similar manner as performed by the exemplary SD-OCT. In the spectral modulation embodiment the detector can alternatively be a photodiode or other single detector that is synchronized to the source modulation element 310. Exemplary lock-in or subtraction techniques can be utilized to extract the OCM signal.

Figure 4A:
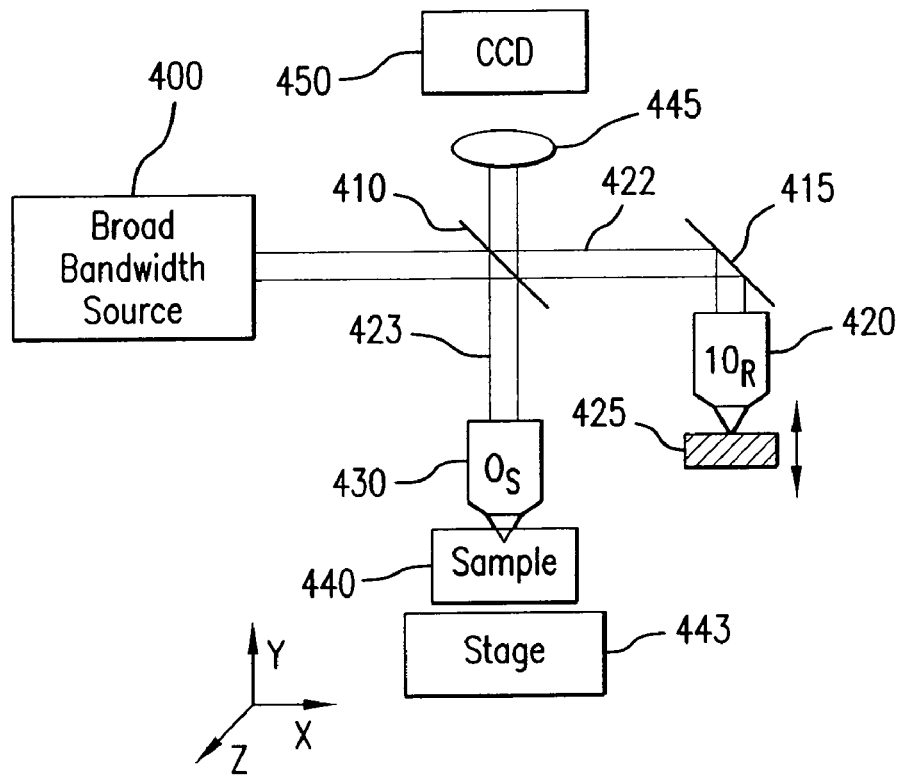
FIG. 4 is a schematic diagram of an exemplary FFOCM system that utilizes a broad bandwidth source.

Full-field optical coherence microscopy is typically a free-space interferometric technique that utilizes a broad bandwidth source to obtain transverse, high-resolution optical sections of biological specimens. FIG. 4A depicts a schematic diagram of an exemplary FFOCM system, where broad bandwidth light 400 is transmitted to a beam splitter 410. Light is split into the sample arm 423 and the reference arm 422. Light in the reference arm 422, according to one exemplary embodiment, may be directed 415 towards a reference objective lens 420 and to a mirror 425, which is capable of an axial motion. Light in the sample arm 423 may be directed towards a sample objective lens 430 and to the sample 440. In one exemplary embodiment, the reference and sample objectives 420, 430 have the similar characteristics.

In another exemplary embodiment, the objective lenses 420, 430 may be optimized for use with immersion fluid that has a refractive index that is similar to the sample. The sample can be coupled to a stage 443 that provides motion in any of three-dimensions. Light from the reference arm 422 and the sample arm 423 can be imaged using a lens 445 onto a CCD camera 450. Fringes are detected by the CCD camera 445 resulting from the interference of the sample arm 422 and the reference arm 423. Multiple images can be typically detected for different positions of the reference arm mirror 425. The exemplary images may be arithmetically combined to extract the information from an optical section within the sample.

Figure 4B:
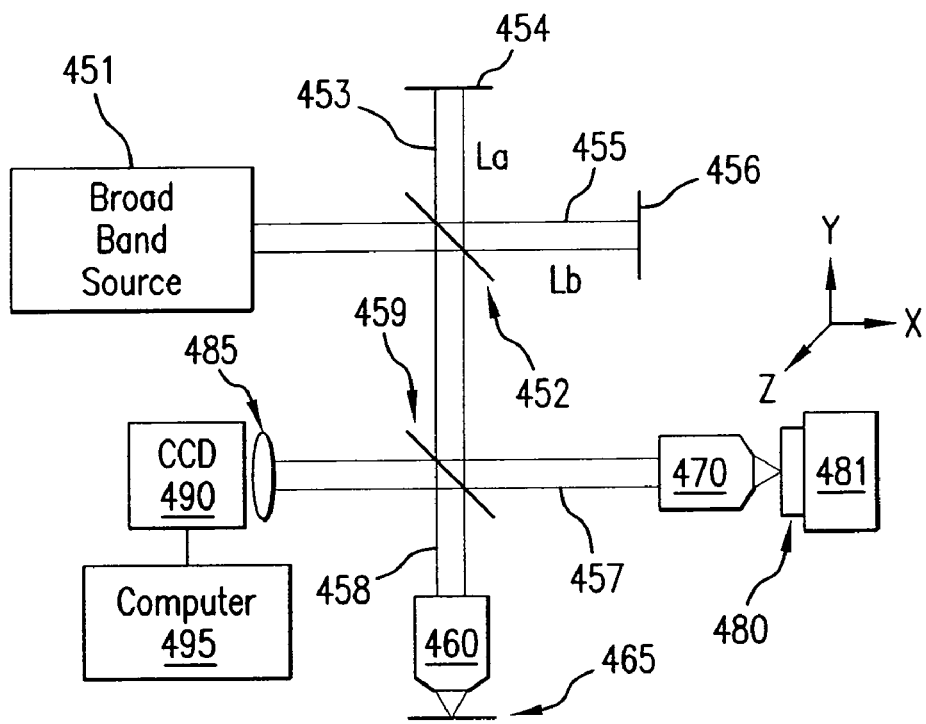

In another exemplary embodiment of the FFOCM system as depicted in FIG. 4B, a broad bandwidth light source 451 can be coupled into a modulating element, such as a Michelson interferometer or other interferometer (e.g. Mach-Zehnder, Sagnac) or spectrum altering unit. For the Michelson interferometer case, light from the source 451 can be transmitted to a beam splitter 452. Light may then be split into two arms for exemplary arm A 453 and arm B 455. Light from arm A 453 is transmitted to a mirror and backreflected back to a beam splitter. Light from arm B 455 is likewise transmitted to a mirror 456, and backreflected back to a beam splitter 452. The difference between the path length $L_a$ in arm A and the path length $L_b$ in arm B, $|L_a-L_b|$, can be set to be substantially equal to the path length difference between the reference and sample arms in the second interferometer. At least one of the arms A or B can be configured to change path lengths or produce a phase shift in the light therein. In one exemplary embodiment, the path length may be changed by a motion of one of the mirrors or a rapidly scanning optical delay line. The motion may be actuated by a piezoelectric transducer, galvanometer, linear motor or the like. Alternatively, path length changes may be generated by one of an acousto-optic modulator or electro optic modulator.

Both reference and sample arm light may be combined at the beam splitter, and transmitted to another static interferometer with beam splitter 459, separating light into a reference arm 458 and a sample arm 457, respectively. Light from both arms 457, 458 can illuminate objective lenses 460, 470, respectively, which are substantially similar. In the reference arm 458, the reference objective lens 460 can be brought to a focus on a reflector 465, which is typically not moving, whereas in the sample arm the sample objective lens 470 focuses the sample arm light on or within the sample 480. The sample 480 or the sample objective lens 470 may be mounted to a stage 481, capable of moving the sample 480 in any of three-dimensions, under manual control or computer control.

The path length difference between the path lengths of the reference arm 458 and the sample arm 457 may be substantially equal to $|L_a-L_b|$ of the first interferometer. Light from reference and sample arms 458, 457, respectively, can be combined at a beam splitter 459, and imaged onto a CCD array 490 or array of detectors via a lens 485. A FFOCM image or data can be generated by a linear combination of images acquired by CCD 490 and while moving or at different positions of mirror 456. Processing, display and storage of FFOCM images is provided by a CPU 495. Accumulations or averages are utilized to increase signal to noise ratio.

Figure 5:
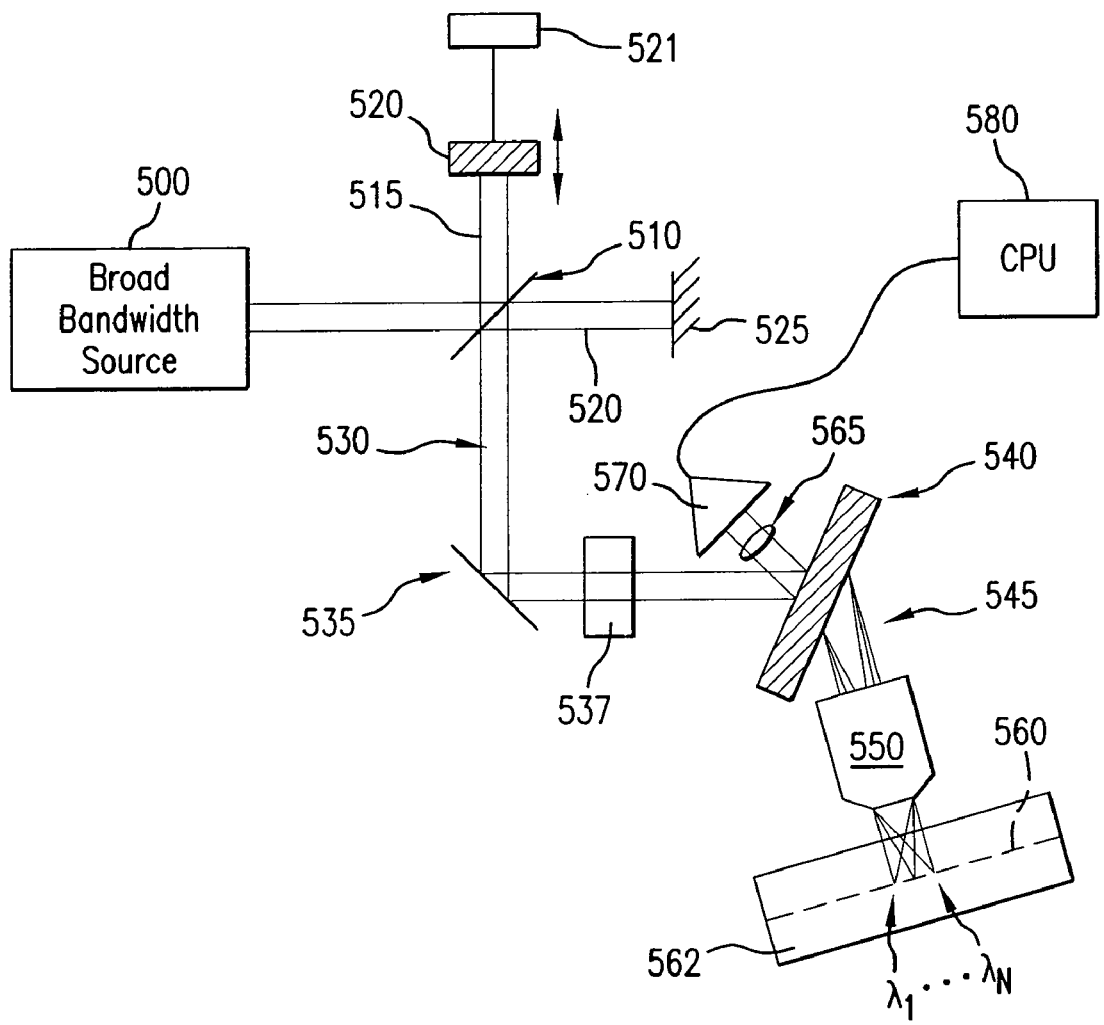
FIG. 5 is a schematic diagram of an exemplary fluorescence SECM system that utilizes a broad bandwidth source.

FIG. 5 depicts an exemplary embodiment of a SECM system configured for a fluorescence detection and using a broad bandwidth source. For example, light from the source 500 can be transmitted to a beam splitter 510, which splits light into two paths 515 and 520. Both arms/paths terminate on mirrors 520 and 525, with at least one arm having a path length or phase that changes over time. Light returned from both arms 530 can be coupled to the beam splitter 510 and directed 535 towards a SECM probe containing a grating or dispersive element 540, an objective lens 550. As discussed herein, the arrangement of the grating and the objective lens 550 focuses a spectrally encoded line 560 on or within the specimen 562 which may be mounted to a three-dimensional stage. Fluorescent light within the sample can be excited by the illuminating light, transmitted back through the objective lens 550, imaged by another lens 565 onto a detector 570. Detected light can be digitized and converted to a line in an image by a processing arrangement (e.g., CPU) 580. Additional lines in the image may be generated at different positions of the beam scanning mechanism 537. Nonlinearities in the moving mirror can be corrected by an exemplary interferometer 521 that has a narrow bandwidth source that illuminates the same moving mirror 520.\

Figure 6:
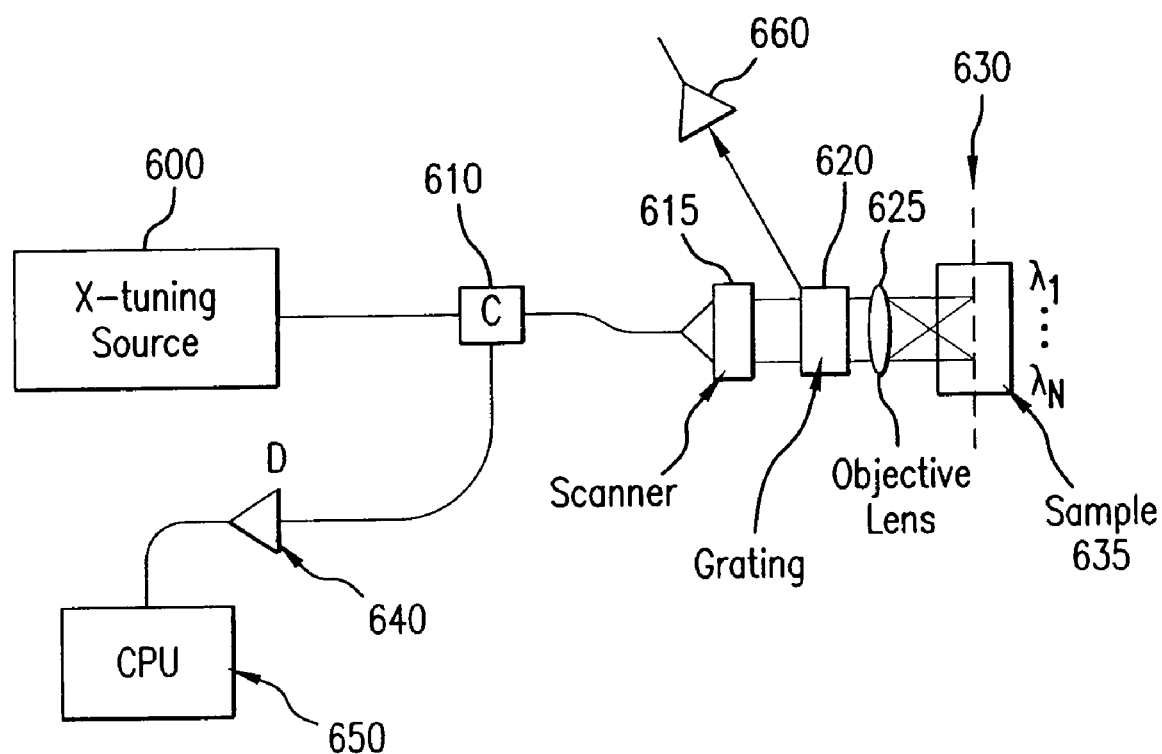
FIG. 6 is a schematic diagram of an exemplary SECM system that utilizes a wavelength tuning source.

FIG. 6 depicts a schematic diagram of an exemplary embodiment of an SECM system that uses a wavelength tuning source 600. For example, the source 600 can be coupled into a circulator/beam splitter 610. According to one exemplary embodiment, light from the splitter 610 is transmitted via an optical fiber to a scanner, which alternatively may also contain a telescope lens imaging system that projects the scan axis to the back focal plane of the objective lens 625. Light from the scanning mechanism is transmitted to a dispersive element 620 (such as a diffraction grating, prism, GRISM, or DP-GRISM, etc.). Light from 620 is transmitted to an objective lens 625, with preferably a high NA, which can focus the beam within the sample 635. At any point in time, one wavelength from the wavelength swept source 600 can illuminate a distinct portion of the sample. As the wavelength of the swept source 600 changes over time, the beam can be scanned along a line 630 within the sample 635. Remitted light from the sample 635 can be transmitted back through the elements 625, 620, and 615, respectively, spatially filtered by the optical fiber or a pinhole and transmitted back to the circulator beam splitter 610. Light from the splitter 610 can be directed to a detector 640, and digitized by a processing arrangement (e.g., CPU) 650, displayed and digitally stored. A single line in the image is obtained following one full sweep of the wavelength-tuning source. Lines may be acquired at different positions of the scanning mechanism to form the image. Fluorescent light excited by the wavelength-tuning source 600 remitted from the sample can be alternatively detected by a detector 660 to form a fluorescent image.

Figure 7:
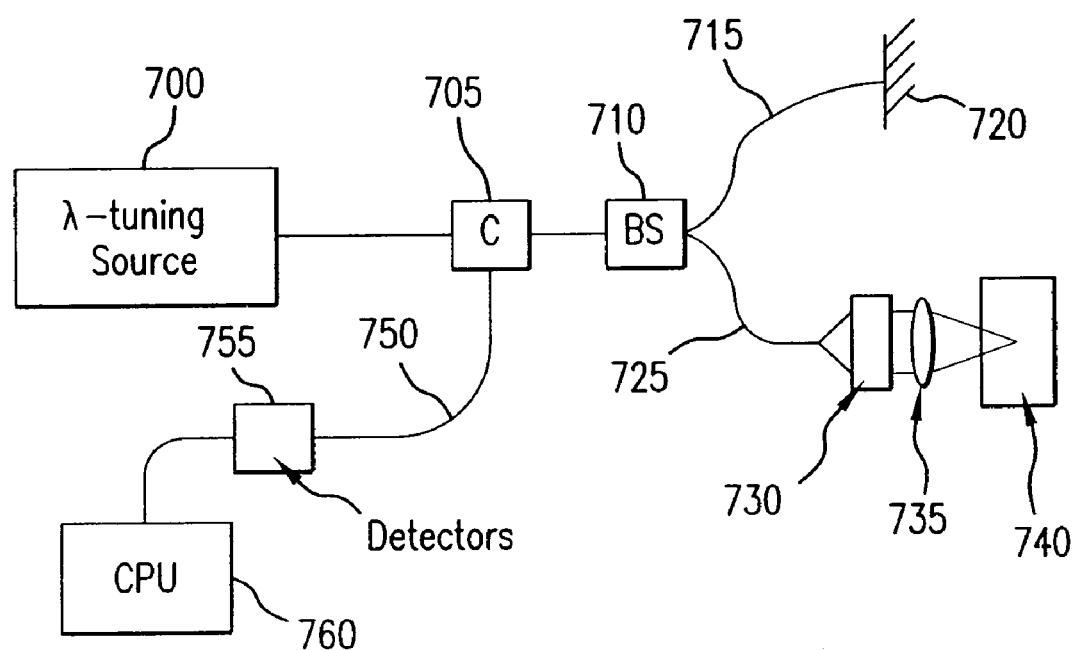
FIG. 7 is a schematic diagram of an exemplary OFDI system that utilizes a wavelength tuning/modulated source.

FIG. 7 depicts a schematic diagram of an exemplary OFDI system. In one exemplary embodiment of this exemplary OFDI system, a wavelength tuning source may be coupled to an optical fiber-based circulator 705 and a beam splitter 705. Light from the circulator 705 can be transmitted to the beam splitter 705, configured to send a majority of light, in the preferred embodiment, to the sample arm 725. Such split light forwarded to the reference arm 715 can be terminated by a reflector 720, and sent back to the beam splitter 710 and the circulator 705. Light in the sample arm 725 is transmitted to a scanning mechanism 730 and an imaging lens 735 that has a NA sufficiently low to allow cross-sectional imaging of the biological specimen 740. Light is reflected from the reference mirror 720 and the sample 740, recombined at the circulator 705, and directed by an optical fiber 750 to a detector apparatus 755, which in an exemplary embodiment can contain dual-balanced detectors.

Light is digitized by the detector apparatus 755 and the digital signal is transmitted to a CPU 760. Spectral interference is processed in a manner similar to the processing using the exemplary SD-OCT system/procedure, e.g., the background is subtracted, λ-space is converted to k-space, and an inverse Fourier transform is performed to produce an A-line. A-lines can be acquired as a function of scanning mechanism position, creating a cross-sectional OFDI image. Alternative exemplary embodiments known in the art, including the capability to obtain spectral information from the sample by short-time-Fourier transformation (STFT) of the spectral interference, complex spectral domain processing, Doppler-sensitive OFDI and polarization-sensitive OFDI, may be also utilized to extract additional information from the biological specimen, such as absorption, flow, and birefringence.

Figure 8:
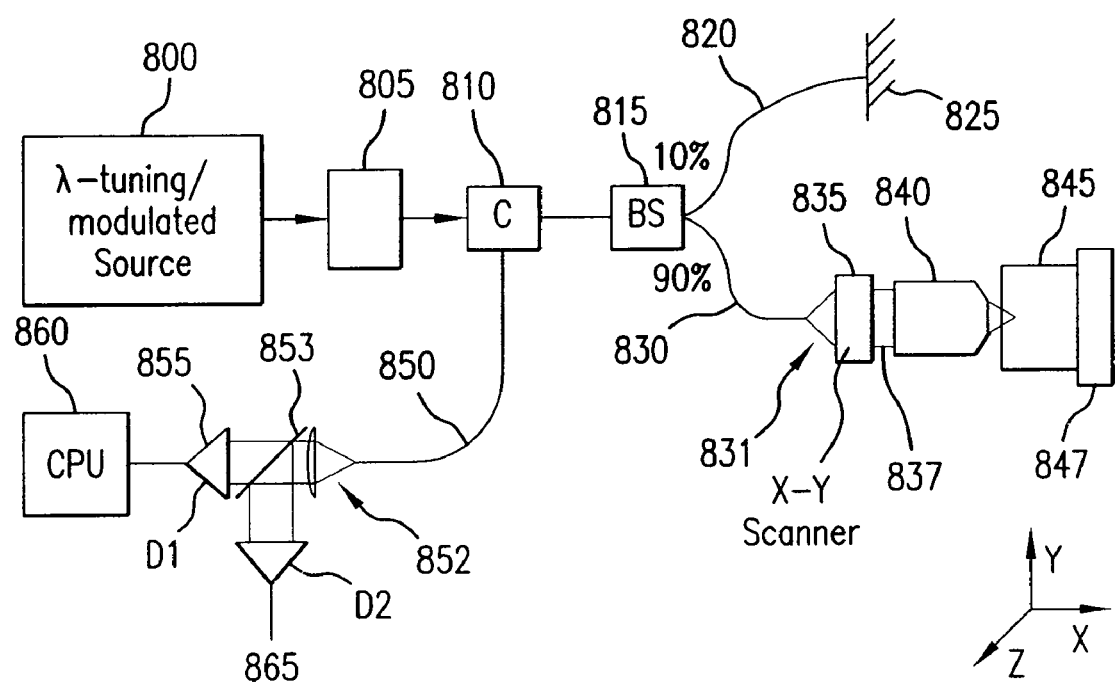
FIG. 8 is a schematic diagram of an exemplary OCM system that utilizes a wavelength modulated/tuning source.

FIG. 8 depicts a schematic diagram of an exemplary embodiment of an OCM system which utilizes a wavelength tuning/modulated source. For example, a wavelength modulation arrangement 805 may produce a spectral pattern on the source, for example, a sinusoidal modulation of the spectrum, which may be altered over time to correspond to spectral interference modulation produced by interference between the sample and reference arms. Light from the source 800 and/or the modulation arrangement 805 can be coupled into a fiber-optic circulator/beam splitter 810, and subsequently transmitted to a beam splitter 815 which preferably directs a majority of light to the sample arm 830.

Light in the reference arm 820 is directed towards a reference reflector 825 or a transmission element. Light in the sample arm 830 can be transmitted to an x-y scanner, which may comprise one or more of galvanometers, resonant scanners, polygon scanners, acousto-optic scanners, electro optic scanners, etc. Light from the scanner can be alternatively transmitted to a telescope 837 and an objective lens 840 with preferably a high NA. The objective lens 840 focuses the light within the sample 845, which is alternatively affixed to a three-dimensional stage 847. Light is returned from the sample back through the elements 840, 837 and 835 and coupled back into preferable the core of an optical fiber or pinhole in the sample arm 831 to reject out-of-focus light. Light is directed to the circulator 810 and transmitted to a detector 855, digitized and transmitted to a CPU 860.

In one exemplary embodiment, OCM data can be obtained by obtaining A-lines from the sample in a similar manner to the way it is performed using the exemplary OFDI system and procedure. For example, in the exemplary spectral modulation system and procedure, the detector can be synchronized to the source modulation element 805. Lock-in or subtraction techniques can be utilized to extract the OCM signal in this case. An exemplary image can be generated by acquiring data for each position of the x-y scanning mechanism 835. Fluorescent light remitted from the sample can be further detected by use of a dichroic mirror or filter 853 and a second detector 865.

Figure 9:
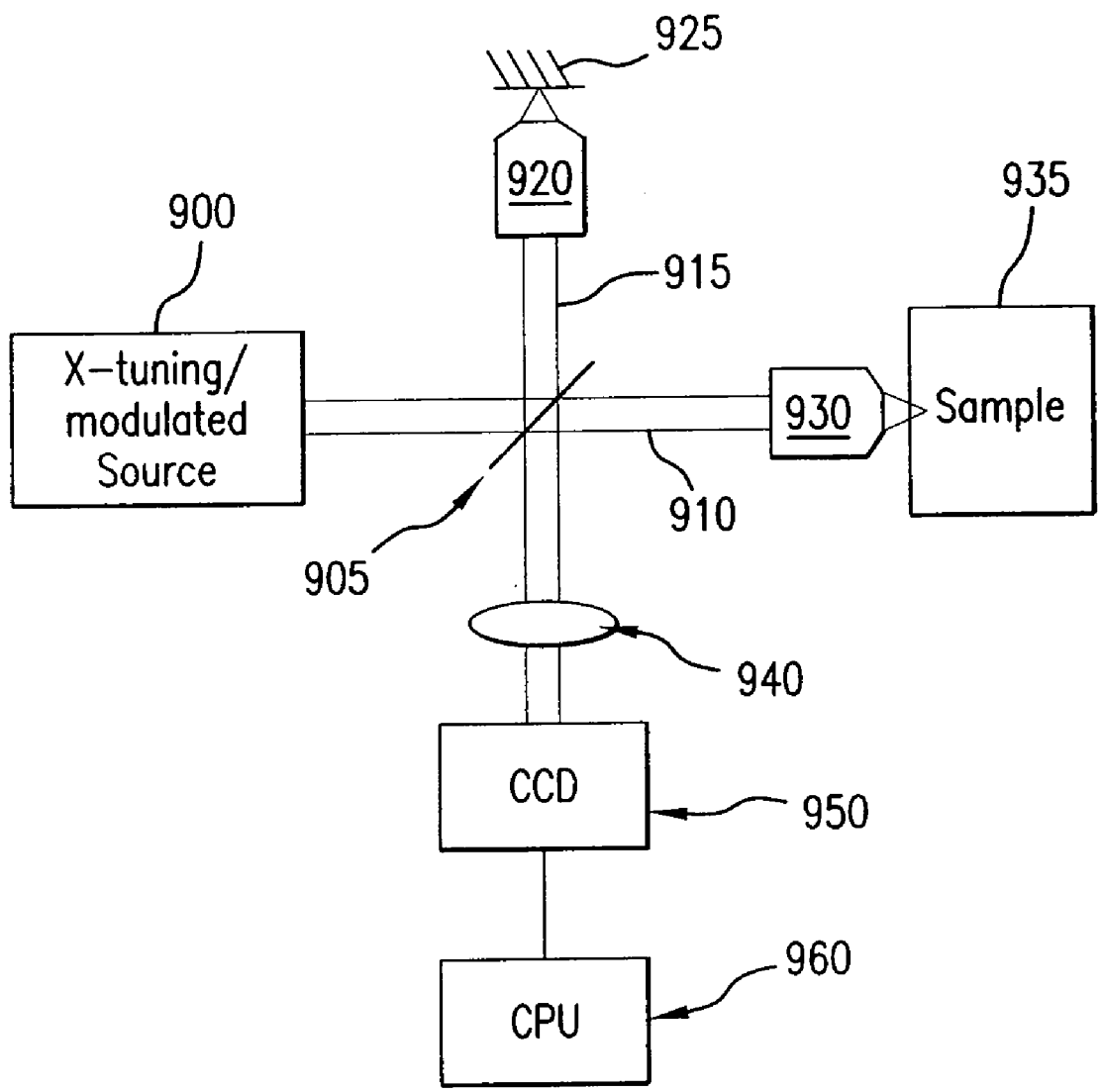
FIG. 9 is a schematic diagram of an exemplary FFOCM system that utilizes a wavelength modulated/tuning source.

FIG. 9 depicts an exemplary embodiment of an FFOCM system that utilizes a wavelength-tuning/modulated source 900. The light source may be tuned over its bandwidth or alternatively be modulated to contain a spectral modulation frequency substantially similar the frequency provided by spectral interference modulation of the interferometer. Light from the source 900 may be coupled into a beam splitter 905, and directed to a sample arm 910 and a reference arm 915, respectively, which are terminated by respective objectives 920, 930. The reference arm objective lens 920 focuses reference arm light onto a reflector, which is subsequently returned to the beam splitter 905. Sample arm light is focused by 930 onto or within the specimen 935. Light remitted from the sample is combined with the reference arm light at 905, and imaged by a lens 940 onto a CCD array 950. Images can be obtained for each wavelength of the wavelength swept source or different modulation patterns of the source and arithmetically combined by a CPU 960 to reconstruct an exemplary FFOCM optical section.

According to one exemplary embodiment of the present invention, the exemplary systems described above and alternative exemplary embodiments thereof may be combined to form a multimodality imaging system. This exemplary combination of systems and/or devices can be provided by creating separate systems, and configuring their optics so that they can obtain images from the same portions of the biological specimen. Different wavelength, scanning, and detection mechanisms may be provided in such combined modality system. Alternatively, the different devices can be implemented using many common components, which they share to provide a more efficient, cost-effective apparatus.

Figure 10:
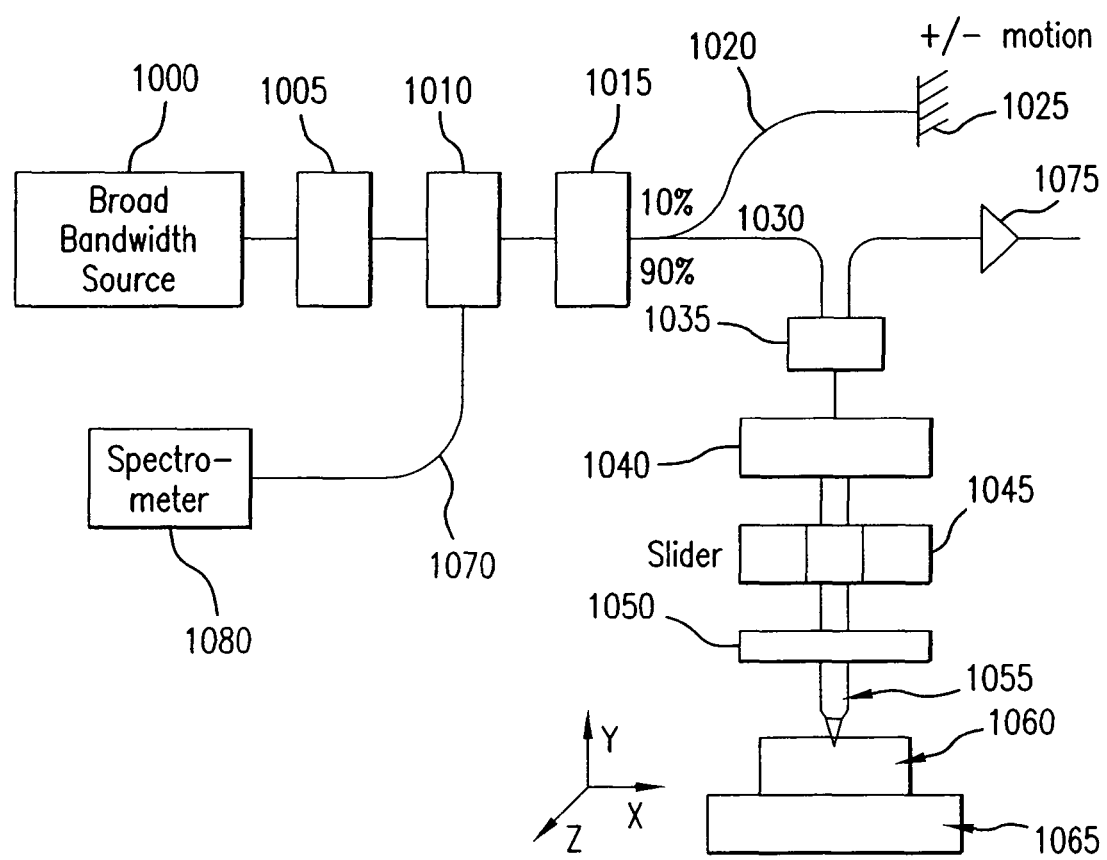
FIG. 10 is a schematic diagram of an exemplary combined SECM/SD-OCT/OCM system that utilizes a broad bandwidth source according to a first exemplary embodiment of the present invention.

FIG. 10 depicts a schematic diagram of a multimodality system according to an exemplary embodiment of the present invention that utilizes a broad bandwidth source 1000 and spectrometer 1080 to provide simultaneous and co-registered SD-OCT, OCM, SECM, and fluorescence SECM data and/or images. For example, light from the broad bandwidth source 1000 can be coupled alternatively to a spectral modulation unit 1005. Light from the spectral modulation unit 1005 is coupled into a circulator 1010 and a beam splitter 1015. If a circulator is utilized, light from the circulator 1010 is transmitted to the beam splitter 1015 that preferably directs a majority of light to the sample. Light in the reference arm 1020 is transmitted to a reference reflector 1025 that may move or otherwise change the path length of 1020, and/or which can be non-movable. If the reference arm is allowed to move, conventional time-domain OCT (e.g., TD-OCT) arrangement and/or procedures may be implemented or complex spectral domain may be obtained using the exemplary SD-OCT arrangement and/or procedures using processes that are known in the art.

Light in the sample arm 1030 is transmitted to a filter/dichroic/WDM apparatus 1035 that transmits the sample arm light in the direction from the beam splitter to the sample. Light from 1035 is directed to a beam scanning mechanism 1040 that is capable of scanning the beam in two directions at high or slow speeds. The beam scanning mechanism 1040 may also contain a telescope for imaging the scanners onto the back focal plane of the lens 1055. Light from the scanning mechanism 1040 can be transmitted to a slider 1045 that contains multiple optical elements. For example, when the slider 1045 is positioned at a distinct position, either one or more or a combination of SD-OCT, OCM, SECM and/or fluorescence OCM arrangements/procedures can be implemented. Light from the slider 1045 can be transmitted to an objective lens 1055 mounted to a lens turret in one embodiment that is capable of changing objective lenses. The slider 1045 and/or turret 1050 may be under computer control for automatic selection of imaging modality. Light is focused by objective lens 1055 onto or within the sample 1060, which may be mounted to a computer-controlled three-dimensional translation stage 1065. Reflected light is transmitted back through the apparatus to 1010, which redirects the light to a spectrometer. Detected reflected light is processed to form exemplary SD-OCT, OCM, SECM images using the arrangements and/or procedures described herein.

As shown in FIG. 10, fluorescent light may be redirected to a second detector via the filter/dichroic mirror/WDM apparatus 1035 to a second detector 1075. Fluorescent light from 1075 is utilized to reconstruct a fluorescent confocal image of the biological sample 1060. In the case where invisible near-infrared light is utilized, a visible aiming beam may be coupled into the exemplary system, coincident with the near-infrared light, to allow visualization of the locations of imaging. Alternatively or in addition, a white light image of the specimen under investigation may be provided by use of an alternative imaging port on the microscope. Alternative exemplary embodiments known in the art, including the capability to obtain spectral information from the sample by short-time-Fourier transformation (STFT) of the spectral interference, Doppler-sensitive SD-OCT and polarization-sensitive SD-OCT, may be also utilized to obtain additional information from the biological specimen, such as, e.g., absorption, flow, and birefringence.

Figure 11:
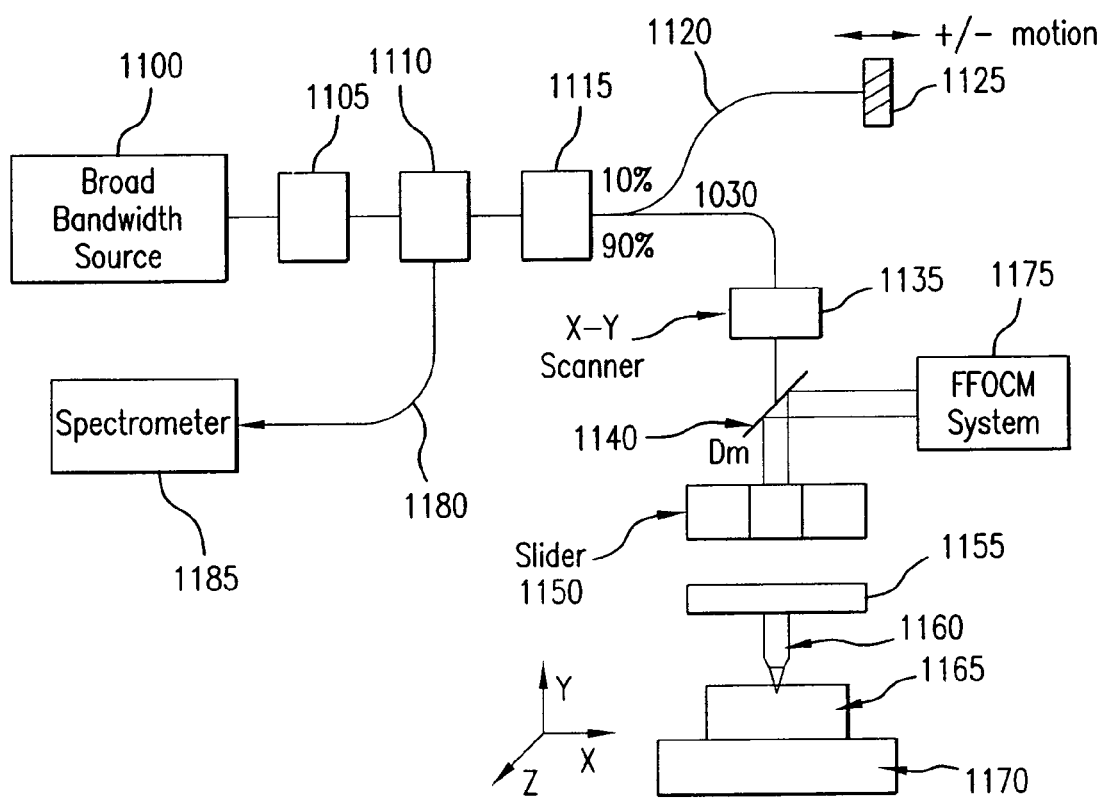
FIG. 11 is a schematic diagram of an exemplary combined SECM/SD-OCT/FFOCM system that utilizes a broad bandwidth source according to a second exemplary embodiment of the present invention.

An alternative exemplary multimodality embodiment configured to provide SD-OCT, OCM, SECM, and FFOCM images and data according to the present invention at a different wavelength from the other three modalities is depicted in FIG. 11. In this exemplary embodiment a broad bandwidth source 1100 is coupled alternatively to a spectral modulation unit 1105. Light from the spectral modulation unit 1105 is coupled into a circulator 1110 and a beam splitter 1115. If the circulator 1110 is utilized, light from the circulator 1110 can be transmitted to the beam splitter 1115 that preferably directs a majority of light to the sample. Light in the reference arm 1120 is transmitted to a reference reflector 1125 that can be stationary and/or may or otherwise change the path length of the reference arm 1120. In case the reference arm 1120 is allowed to more, exemplary conventional time-domain OCT (TD-OCT) procedures or complex spectral domain may be utilized for SD-OCT by methods known in the art. Light in the sample arm 1130 is transmitted a beam scanning mechanism 1135 that is capable of scanning the beam in two directions at high or slow speeds. The beam scanning mechanism 1135 may also include a telescope for imaging the scanners onto the back focal plane of the lens 1160. Light from the scanning mechanism 1135 is transmitted to a dichroic splitter/WDM 1140 that transmits the excitation light for SD-OCT, OCM, and SECM modalities, and can reflect FFOCM light.

For example, an exemplary FFOCM system similar to that shown in FIG. 3 can be coupled into the beam path via 1140. Light from 1140 is directed to a slider 1150 that contains multiple optical elements; when the slider may be positioned at a distinct position, either one or a combination of SD-OCT, OCM, SECM or FFOCM is provided. Light from the slider 1150 is transmitted to an objective lens 1160 mounted to a lens turret 1155 in one embodiment that is capable of changing objective lenses. The slider 1150 and/or turret 1155 may be under computer control for automatic selection of imaging modality. Light is focused by the objective lens 1160 onto or within the sample 1165, which may be mounted to a computer-controlled three-dimensional translation stage 1170. Reflected light is transmitted back through the apparatus to the circulator 1110, which redirects the light to a spectrometer. Detected reflected light may be processed to form exemplary SD-OCT, OCM, SECM images by methods described herein. FFOCM light may be redirected to the FFOCM system 1175 via the filter/dichroic mirror/WDM apparatus 1140.

In the case where invisible near-infrared light is utilized, a visible aiming beam may be coupled into the exemplary system shown in FIG. 11, coincident with the near-infrared light, to allow visualization of the locations of imaging. Alternatively or in addition, a white light image of the specimen under investigation may be provided by use of an alternative imaging port on the microscope. Alternative exemplary embodiments known in the art, including the capability to obtain spectral information from the sample by short-time-Fourier transformation (STFT) of the spectral interference, Doppler-sensitive SD-OCT and polarization-sensitive SD-OCT, may be also utilized to extract additional information from the biological specimen, such as, e.g., absorption, flow, and birefringence.

Figure 12:
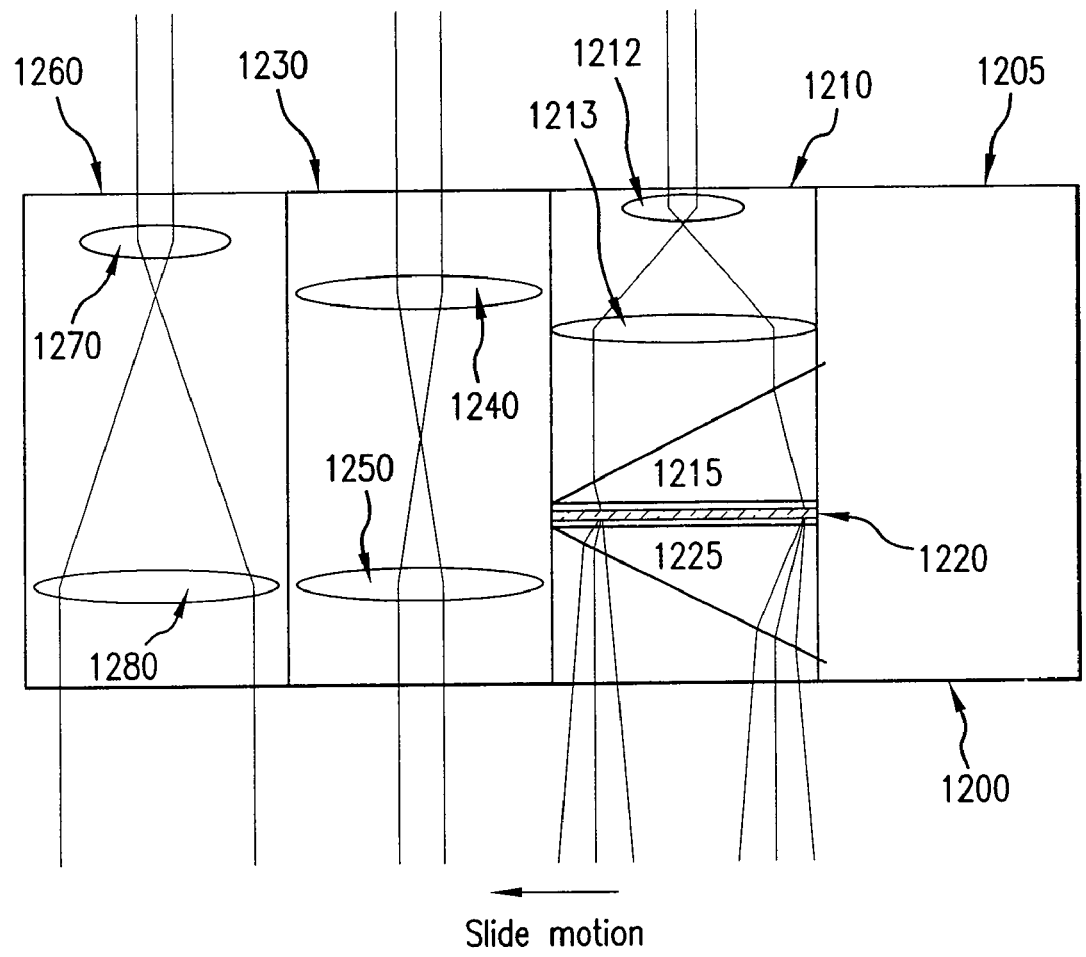
FIG. 12 is a schematic diagram of exemplary multimodality microscope sliders according to a particular exemplary embodiment of the present invention.

FIG. 12 depicts an exemplary embodiment of an arrangement of sliders that may be utilized for the multimodality imaging according to the present invention. For example, optical elements can be contained in a housing 1200 that may be translated manually, or under computer or automatic control. Each slider position can terminate in different slider positions 1205, 1210, 1230, 1260 that provide one or more imaging modalities. The slider position 1205, 1210, 1230, 1260 may be coupled to the objective lens turret. In one exemplary embodiment, the slider position 1205 contains no optical elements (air) or optical element windows. In this exemplary configuration, the microscope is configured to perform FFOCM. For the slider position 1210, a lens apparatus 1212 and 1213 can be configured to expand the beam and illuminate a DP-GRISM containing two prisms 1215 and 1225 that surround a transmission grating 1220. This exemplary configuration provides an ability to perform the SECM imaging. Exemplary OCM procedures can also be conducted in this position using a scanning mechanism that scans the spectrally-encoded line across the sample. For the slider position 1230, a lens apparatus 1240, 1250 can be configured to image beam angle, with or without beam magnification. This slider position 1230 can provide imaging using exemplary SDOCT procedures. For the slider position 1260, a lens apparatus 1270, 1280 is configured to expand the scanned beam to allow imaging using the exemplary OCM procedures.

Figure 13:
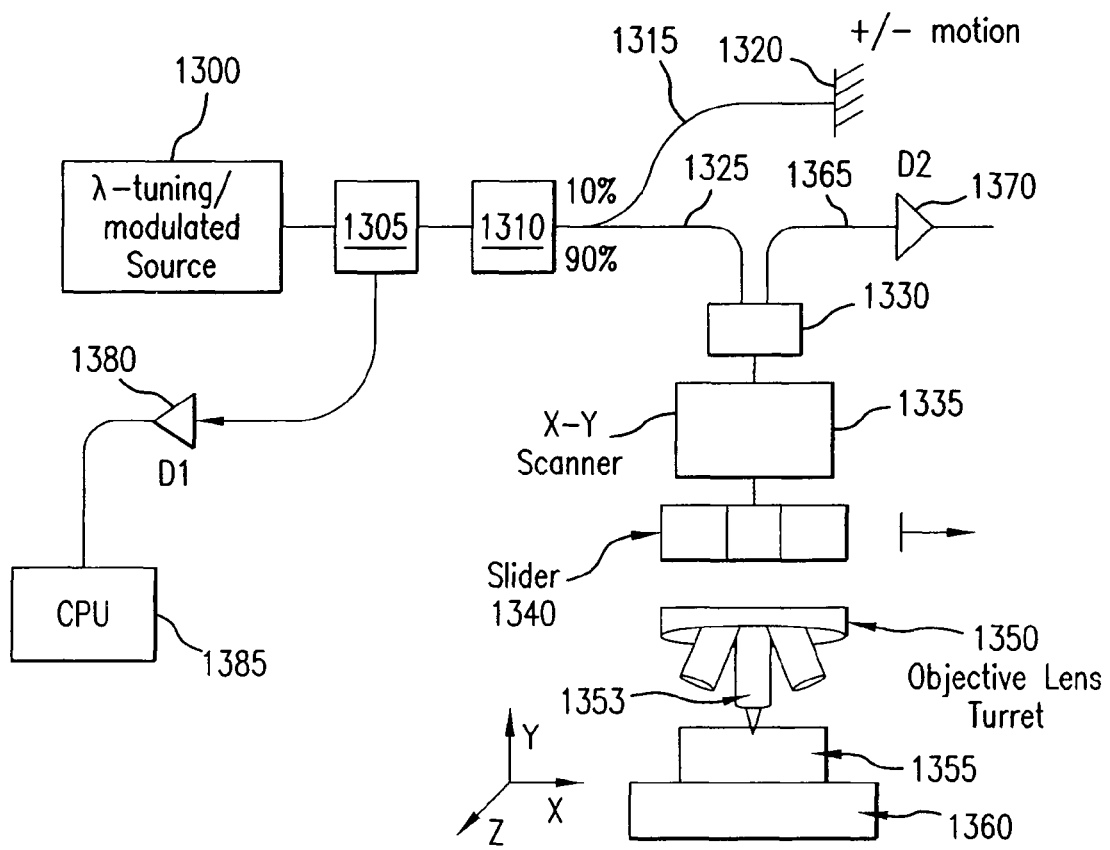
FIG. 13 is a schematic diagram of an exemplary combined SECM/OFDI/OCM system that utilizes a wavelength tuning source according to a third exemplary embodiment of the present invention.

While certain embodiments of the multimodality imaging systems have utilized a broad bandwidth source, exemplary embodiments of combined systems can also include wavelength tuning/modulated sources and single or multiple detector configurations, and such exemplary embodiment is shown in FIG. 13. For example, in FIG. 13, a wavelength tuning/modulated source 1300 is coupled into a circulator 1305 and a beam splitter 1310. If a circulator is utilized, light from the circulator 1305 is transmitted to a beam splitter 1310 that preferably directs a majority of light to the sample. Light in the reference arm 1315 is transmitted to a reference reflector 1320 that may be stationary, and may or otherwise change the path length of 1315. In case the reference arm is allowed to move, conventional exemplary time-domain OCT (TD-OCT) procedures may be provided or complex spectral domain may be utilized for implementing OFDI modalities by methods known in the art. Light in the sample arm 1325 is transmitted to a filter/dichroic/WDM apparatus 1330 that transmits the sample arm light in the direction from the beam splitter to the sample. Light from 1330 is directed to a x-y beam scanning mechanism 1335 that is capable of scanning the beam in two directions at high or slow speeds.

The beam scanning mechanism 1335 may also include a telescope for imaging the scanners onto the back focal plane of the lens 1353. Light from the scanning mechanism 1335 is transmitted to a slider 1340 that contains multiple optical elements; when the slider is positioned at a distinct position, either one or a combination of OFDI, OCM, SECM or fluorescence OCM modalities can be provided. Light from the slider 1340 is transmitted to an objective lens 1353 mounted to a lens turret 1350 in one embodiment that is capable of changing objective lenses. The slider 1340 and/or turret 1350 may be manual, under computer control for automatic selection of imaging modality. Light is focused by objective lens 1353 onto or within the sample 1355, which may be mounted to a computer-controlled three-dimensional translation stage 1360.

Reflected light is transmitted back through the apparatus to 1305, which redirects the light to a detector apparatus 1380 suitable for detecting OFDI, wavelength tuning OCM or SECM signals, images and/or data. Detected reflected light is processed by a CPU 1385 to form exemplary OFDI, OCM, SECM images by methods described above.

Fluorescent light may be redirected to a second detector via the filter/dichroic mirror/WDM apparatus 1330 to a second detector 1370. Fluorescent light from 1370 is utilized to reconstruct a fluorescent confocal image of the biological sample 1355. In the case where invisible near-infrared light is utilized, a visible aiming beam may be coupled into the system, coincident with the near-infrared light, to allow visualization of the locations of imaging. Alternatively or in addition, a white light image of the specimen under investigation may be provided by use of an alternative imaging port on the microscope. Alternative embodiments known in the art, including the capability to obtain spectral information from the sample by short-time-Fourier transformation (STFT) of the spectral interference, Doppler-sensitive SD-OCT and polarization-sensitive SD-OCT, may be also utilized to extract additional information from the biological specimen, such as absorption, flow, and birefringence.

Figure 14:
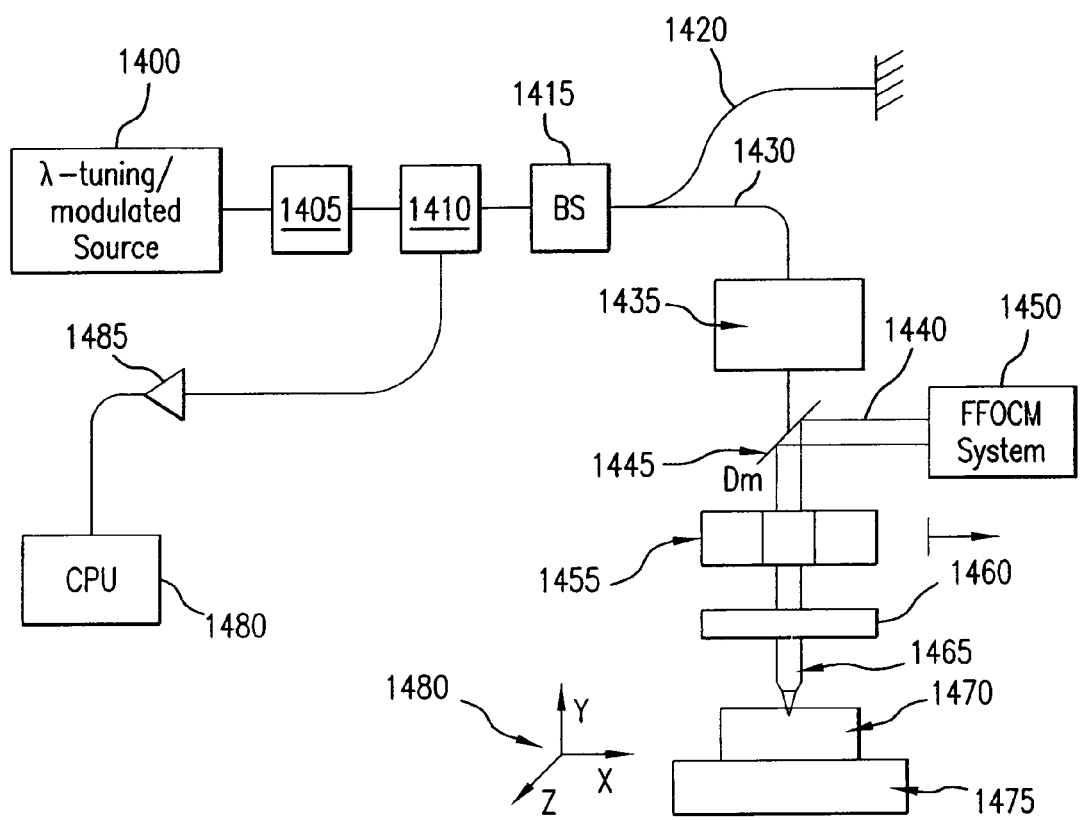
FIG. 14 is a schematic diagram of an exemplary combined SECM/OFDI/FFOCM system that utilizes a wavelength tuning source according to a third exemplary embodiment of the present invention.

Another exemplary multimodality embodiment of a system according to the present invention which is configured to provide OFDI, OCM, SECM, and FFOCM images, data and other information, where FFOCM signal is provided at a different wavelength from the other three modalities, is depicted in FIG. 14. In this exemplary embodiment, a wavelength tuning source 1400 is coupled alternatively to a spectral modulation unit 1405. Light from the modulation unit 1405 is coupled into a circulator 1410 and a beam splitter 1415. If the circulator 1410 is utilized, light from the circulator 1410 is transmitted to the beam splitter 1415 that preferably directs a majority of light to the sample. Light in the reference arm 1420 is transmitted to a reference reflector 1425 that may be stationary, or can move or otherwise change the path length of 1420. In case the reference arm 1420 is allowed to move, conventional time-domain OCT (TD-OCT) procedures and modalities may be provided or complex spectral domain may be obtained for the OFDI data by methods known in the art. Light in the sample arm 1430 is transmitted a beam scanning mechanism 1435 that is capable of scanning the beam in two directions at high or slow speeds. The beam scanning mechanism 1435 may also contain a telescope for imaging the scanners onto the back focal plane of the lens 1465. Light from the scanning mechanism 1435 is transmitted to a dichroic splitter/WDM 1445 that transmits the excitation light for OFDI, OCM, and SECM, but reflects FFOCM light.

An exemplary FFOCM system similar to the system(s) of FIG. 3 and/or FIG. 4 can be coupled into the beam path via the dichroic splitter/WDM 1445. Light from the dichroic splitter/WDM 1445 is directed to a slider 1455 that contains multiple optical elements; when the slider 1455 is positioned at a distinct position, either one or a combination of OFDI, OCM, SECM or FFOCM data and/or images is provided. Light from the slider 1455 is transmitted to an objective lens 1465 mounted to a lens turret 1460 in one exemplary embodiment that is capable of changing the objective lenses. The slider 1455 and/or a turret 1460 may be under computer control for an automatic selection of imaging modality. Light can be focused by objective lens 1465 onto or within the sample 1470, which may be mounted to a computer-controlled three-dimensional translation stage 1475.

Reflected light is transmitted back through the apparatus to 1410, which redirects the light to a spectrometer. Detected reflected light is processed to form OFDI, OCM, SECM images by methods described herein. FFOCM light may be redirected to the FFOCM system 1450 via the filter/dichroic mirror/WDM apparatus 1445. In the case where invisible near-infrared light is utilized, a visible aiming beam may be coupled into the exemplary system, coincident with the near-infrared light, to allow visualization of the locations of imaging. Alternatively or in addition, a white light image of the specimen under investigation may be provided by use of an alternative imaging port on the microscope. Alternative exemplary embodiments known in the art, including the capability to obtain spectral information from the sample by short-time-Fourier transformation (STFT) of the spectral interference, Doppler-sensitive OFDI and polarization-sensitive OFDI may be also utilized to extract additional information from the biological specimen, such as absorption, flow, and birefringence.

In another exemplary embodiment of the present invention, the microscope can be configured to allow imaging from both sides of the sample. For example, SDOCT, SECM and OCM procedures can be performed from above the sample, and FFOCM procedures may be performed with the imaging lens illuminates the sample from below. In such exemplary configuration, the sample can be mounted between a microscope slide and a thin cover glass, to allow imaging from both sides.

The exemplary systems described herein can provide a multimodality imaging of biological specimens in a variety of different formats, speeds, resolutions, fields of view, and contrast mechanisms. Each image data set may be two- or three-dimensional, and may be co-registered to the data sets of the other respective imaging modalities. Computer processing methods known in the art may be utilized to display the different data sets in a variety of different imaging formats including three-dimensional volume visualization, four-dimensional representations, and processed two-, three- and four-dimensional data sets, where the processing apparatus is configured to highlight important areas of interest. Any one or more datasets may be displayed with respect to the other and a comprehensive, all-inclusive dataset may be derived from a combination of the individual data sets. Quantitative information may be derived from the data sets in their two-, three-, and four-dimensional contexts. Image data may also be combined with conventional fluorescent or brightfield images of the biological specimen.

EXAMPLES

Provided below are examples conducted to investigate using exemplary multiple imaging modalities according to the present invention to image the developing Xenopus laevis heart.

Exemplary Methods

Bench-Top Exemplary OCT and OFDI Systems

In the exemplary TDOCT configuration, axial ranging is performed by use of low coherence reflectometry where the individual depth points are probed sequentially in time. A broad bandwidth (50 nm) source centered at 1.3 μm was used, providing an axial resolution of ~10 μm in tissue (n=1.4). The frame rate was 20 per second (2 kHz A-line rate, 100×500 pixels).

Exemplary OFDI procedures and systems can use a frequency domain reflectometry in which all depth points are acquired simultaneously. This technique provides a several-hundred-fold improvement in signal-to-noise ratio (SNR) as described in M. A. Choma et al. "Sensitivity advantage of swept source and Fourier domain optical coherence tomography," *Optics Express* 11, pp 2183-2189 (2003); and S. H. Yun et al., "High-speed optical frequency-domain imaging," *Optics Express* 11, pp. 2953-2963 (2003). The exemplary OFDI systems and procedures can use a rapidly swept, wavelength tunable laser as a light source. An extended-cavity semiconductor laser employing an intracavity spectral filter, as described in M. A. Choma et al. "Sensitivity advantage of swept source and Fourier domain optical coherence tomography," *Optics Express* 11, pp 2183-2189 (2003), C. Boudoux et al., "Rapid wavelength-swept spectrally encoded confocal microscopy," *Optics Express* 13, pp. 8214-8221 (2005).

The laser featured a sweep repetition rate of up to 64 kHz, a wide tuning range of 111 nm centered at 1320 nm, and a high average output power of 30 mW (7 mW on the tissue). The axial resolution was 10 μm in tissue. The system further comprised an acousto-optic frequency shifter (25 MHz) to remove the depth degeneracy inherent in the frequency-domain reflectometry, as described in S. H. Yun et al., "Removing the depth-degeneracy in optical frequency domain imaging with frequency shifting," *Optics Express* 12, pp. 4822-4828 (2004). Polarization-diversity detection was implemented to eliminate polarization artifacts in the fiber-based OFDI system. Dual-balanced photoreceivers were used to improve imaging sensitivity through the reduction of laser intensity noise. The photoreceiver outputs were digitized with a 2-channel analog-to-digital converter at a sampling rate of 100 MHz with 14-bit resolution.

Exemplary TDOCT and high-speed OFDI configuration were incorporated into a dissecting light microscope. The scanning system was comprised of a collimating lens (5 mm beam diameter), two synchronized galvanometric scanners for transverse scanning, a focusing lens (50 mm focal length), and a small mirror that deflected the beam downward toward the sample. For exemplary TDOCT and OFDI configuration, the transverse resolution was 16 μm with a confocal parameter of 330 μm.

Displacements associated with local cardiac motion were determined directly from the volumetric data by subtracting the heart surface locations at end diastole from those at end systole on a frame-by-frame basis. Displacement was displayed using a color look up table. Volumetric rendering and three-dimensional visualization was accomplished by using OsiriX software.

High-resolution OFDI procedure was performed using a laser source with 200 nm tuning range, centered at 1250 nm, in which two semiconductor optical amplifiers were utilized as the gain media, as described in W. Y. Oh et al., "Wide tuning range wavelength-swept laser with two semiconductor optical amplifiers," *IEEE Photonics Technology Letters* 17, pp. 678-680 (2005). An axial resolution of 4 μm in tissue was achieved. The transverse resolution was 2 μm with NA=0.2 objective lens. The imaging rate was 40 frames per second with an A-line rate of 20 kHz (500 A-lines per frame). Polarization-diversity and dual-balanced detection was performed and the photoreceiver outputs were digitized with a 2-channel analog-to-digital converter at a sampling rate of 10 MHz with 12-bit resolution.

Exemplary FFOCM System

For example, FFOCM is an interferometric technique that utilizes two-dimensional parallel detection to provide subcellular resolution images of reflected light within biological specimens, as described in A. Dubois et al., "Ultrahigh-resolution full-field optical coherence tomography," *Appl Opt* 43, pp. 2874-2883 (2004), and A. Dubois et al., "Three-dimensional cellular-level imaging using full-field optical coherence tomography," *Phys Med Biol* 49, pp. 1227-1234 (2004). The exemplary FFOCM system used spatially incoherent broadband light from a xenon arc lamp to illuminate the sample and the reference mirror of a Linnik interference microscope using two identical NA=0.3 water-immersion microscope objective lenses. Interference images were captured with a CMOS area scan camera with spectral response centered at 650 nm. The transverse resolutions were 2 μm and axial resolution, 1.1 μm. Acquisition time was 2 seconds per frame for a transverse field of view of approximately 700 μm×700 μm. Three-dimensional data was obtained by moving the sample through the focus at 1 μm increments. Volumetric rendering and visualization was accomplished by using OsiriX software.

Exemplary SECM System

For example, SECM is a reflectance confocal microscopy technique, which uses near-infrared light that allows deeper penetration into tissue, as described in R. R. Anderson et al., "The optics of human skin," *J Invest Dermatol* 77, pp. 13-19 (1981), compared with confocal microscopes that utilize visible light. Exemplary SECM technique differs from conventional laser scanning confocal microscopy in that it projects different wavelengths onto distinct locations on the sample, as described in G. J. Tearney et al., "Spectrally encoded confocal microscopy," *Optics Letters* 23, pp. 1152-1154 (1998). Rapid acquisition of spectra returned from the sample enables high-speed reconstruction of the image. In the SECM system, as described in C. Boudoux et al., "Rapid wavelength-swept spectrally encoded confocal microscopy," *Optics Express* 13, pp. 8214-8221 (2005), light from a rapid wavelength tuning source in the near-infrared (center wavelength=1.32 μm, instantaneous line width=0.1 nm, total bandwidth=70 nm, repetition rate up to 15.7 kHz), was collimated onto a diffraction grating (1100 lines per mm) and focused using a 1.2 NA, 60× objective (Olympus UPlanApo/

IR 60X/1.20W). A multimode fiber was used for signal collection, resulting in 0.9 µm transverse and 2.5 µm axial resolutions. Images comprised of 500×500 pixels were acquired at 10 frames per second. The maximum imaging depth was limited to the 280 µm working distance of the objective lens.

Specimen Preparation, Ethanol Treatment and Histology

Xenopus laevis frogs were purchased from Nasco (Fort Atkinson, Wisconsin). Animal procedures were performed according to the approved protocols of Massachusetts General Hospital Subcommittee on Research Animal Care. Embryos were obtained by in vitro fertilization, incubated in 0.1× Marc's modified Ringer's medium (MMR)(as described in J. Newport et al., "A major development transition in early Xenopus embryos: 1. Characterization and timing of cellular changes at the midblastula stage," *Cell* 30, pp. 675-686, 1982), and staged according to Nieuwkoop and Faber tables. (see P. D. Nieuwkoop and J. Faber, *Normal table of Xenopus laevis, Daudin*, North-Holland Publishing Company, Amsterdam, 1967).

Ethanol treatments were performed in 0.1×MMR (vol/vol), soon after Mid Blastula Transition (stage 8.5) (as described in R. Yelin et al., "Ethanol exposure affects gene expression in the embryonic organizer and reduces retinoic acid levels," *Dev Biol* 279, pp. 193-204 (2005).) until imaging. Prior to in vivo imaging, embryos were anesthetized using 0.02% 3-aminobenzoic acid ethyl ester (A-5040, Sigma). For TDOCT and OFDI imaging techniques and systems, embryos were positioned on a 1.5% agarose gel plate with their ventral side facing up, covered by the anesthesia working solution. For imaging with the exemplary SECM system, embryos were placed on a cover slip, lying on their ventral side in an anesthesia buffer, and imaged from below. In vitro imaging by the exemplary FFOCM procedures and/or systems commenced following fixation in MEMFA (0.1M MOPS [pH7.4], 2 mM EGTA, 1 mM MgSO4 and 3.7% formaldehyde) for greater than one hour. Prior to imaging, the fixed embryos were transferred into a Petri dish with 1×PBS (8 gr NaCl, 0.2 gr KCl, 1.44 gr Na2HPO4, 0.24 gr KH2PO4), with its ventral side facing up, supported by clay.

Plastic Histology sections (as described in A. M. Glauert, *Fixation, Dehydration and Embedding of Biological Specimens.*, North-Holland Publishing Company Amsterdam, 1986) were obtained after additional fixation in Karnovsky's Fixative (KII) and embedding in tEpon-812 (Tousimis). Sections of 1 µm thick were cut on a Reichert Ultracut Microtome and stained with methylene blue/toluidine blue in borate buffer (Tousimis). Paraffin sections (5 µm thickness) were stained with Hematoxylin & Eosin.

Exemplary Results

Four-dimensional Imaging of Embryonic Heart with OFDI Techniques In Vivo

Figure 15A:
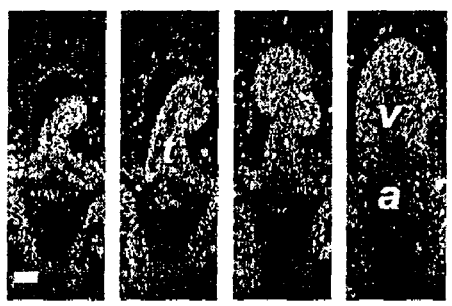
FIGS. 15a-15m are various exemplary images of Xenopus laevis hearts (stage 49) in vivo using exemplary embodiments of the TDOCT and OFDI procedures.
Figure 15B:
Figure 15:
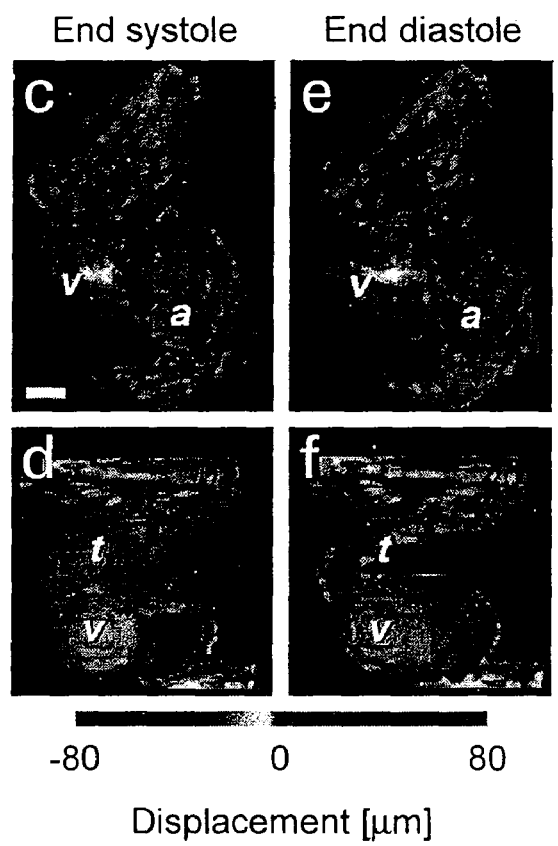

Rapid volumetric imaging of the beating heart enables the evaluation of three-dimensional morphology and function during the cardiac cycle. Compared with TDOCT, which provides cross-sectional imaging in vivo (as shown in FIGS. 15a and 15b), the exemplary OFDI system and procedure can image at much higher frame rates, making four-dimensional imaging of the beating heart without cardiac gating possible. Volumetric OFDI images of the Xenopus heart (stage 49) were acquired at a rate of 20 three-dimensional data sets per second (as shown in FIGS. 15c-15g). At end systole, the use of the OFDI procedure demonstrated that the ventricle was at its smallest volume; the volumes of the atrium and truncus arteriosus (TA) were conversely at their maxima (as shown in FIGS. 15c and 15d). At end diastole, the ventricle was dilated to its greatest volume, whereas the volumes of the atrium and TA were at their minima (as shown in FIGS. 15e and 15f). A three-dimensional rendering of the heart (as shown in FIG. 15g), taken from the four-dimensional data set, corresponds to a brightfield photograph of the same heart following its dissection (as shown in FIG. 15h).

High-resolution OFDI Procedure on Embryonic Heart In Vivo

While the exemplary OFDI system was capable of four-dimensional imaging, there are cases where higher resolution is required to identify subtle morphological and functional abnormalities. In order to increase resolution, OFDI cross-sections of a stage 49 Xenopus heart were obtained in vivo (as shown in FIGS. 15i-15m) using a broadband (e.g., 200 nm) wavelength-swept source, as described in W. Y. Oh et al., "Wide tuning range wavelength-swept laser with two semiconductor optical amplifiers," *IEEE Photonics Technology Letters* 17, pp. 678-680 (2005) Compared to the 16 µm transverse and 10 µm axial resolutions of the previously described TDOCT and OFDI procedures and systems, the transverse and axial resolutions of high resolution OFDI results were 2 µm and 4 µm, respectively. Details within the three-chamber Xenopus heart can be clearly resolved with the high-resolution OFDI procedures and systems, including atrioventricular valve dynamics (as shown in FIGS. 15i-15k), ventricular contractions, and trabecular dynamics (FIG. 15m). Individual blood cells can also be seen, flowing from the atrium to the ventricle through the atrioventricular valve (as shown in FIG. 15k).

Figure 16H:
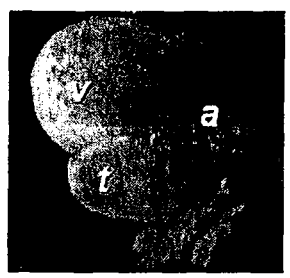
Figure 16I:
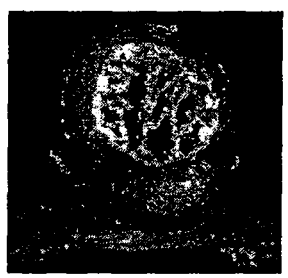
Figure 16J:
Figure 16K:
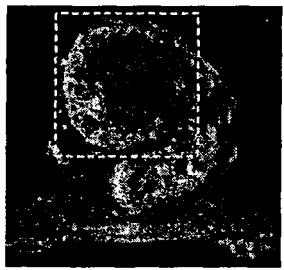
Figure 16L:
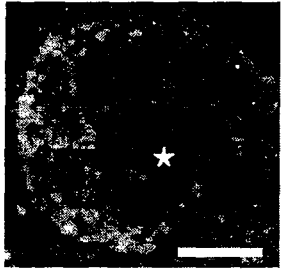
Figure 16M:
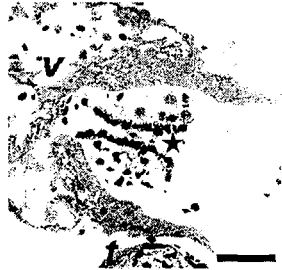

High-resolution Three-dimensional Imaging of Embryonic Heart Using FFOCM Procedures In Vitro Exemplary FFOCM procedures and systems offer the capability to image microstructure of the embryonic heat with nearly isotropic cellular level resolution. Volumetric FFOCM images spanned a field of view of 700×700×1000 µm (axial). The transverse and axial resolutions were 2 µm and 1.1 µm, respectively. Acquisition time was 2 seconds for a single en face section, and 33 minutes for the entire volume. Exemplary FFOCM sections of the Xenopus heart (stage 49) allow visualization of ventricular trabeculae (as shown in FIGS. 16a and 16c), the spiral valve (as shown in FIGS. 16b and 16d, see arrows), and the partial atrial septum (as shown in FIG. 16d, see arrow head) with greater detail than generated using the exemplary TDOCT or OFDI procedures or systems. Partially transparent volumetric rendering of the heart (as shown in FIGS. 16e-16h), reveals the looping-compression structure with the angled TA (as shown in FIG. 16e), the aortic arches (as shown in FIGS. 16f and 16g), and the thin wall of the atrium (as shown in FIGS. 16g and 16h), in their three-dimensional context. Cut-away views of (as shown in FIG. 16e) show fine three-dimensional internal structures, including the trabeculae (as shown in FIGS. 16i and 16j) and the atrioventricular valve (as shown in FIG. 16k). A magnified view of the atrioventricular valve shown (as shown in FIG. 16l) next to a corresponding histology section of the same embryo (as shown in FIG. 16m), demonstrates its bicuspid morphology.

High-speed Imaging of Embryonic Heart with SECM Procedures In Vivo

Figure 17A:
FIGS. 17a-17h are exemplary high-resolution confocal images obtained in vivo using the exemplary embodiments of the SECM procedure.
Figure 17B:
Figure 17C:
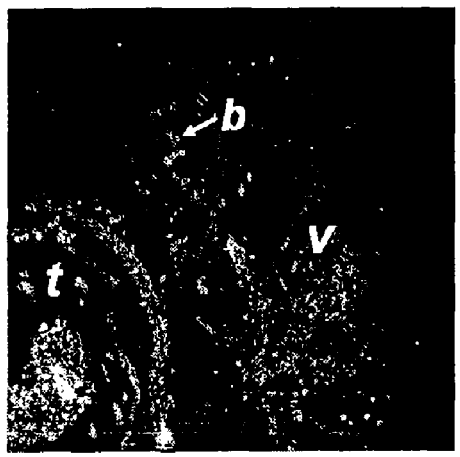
Figure 17D:
Figure 17E:
Figure 17F:
Figure 17G:
Figure 17H:
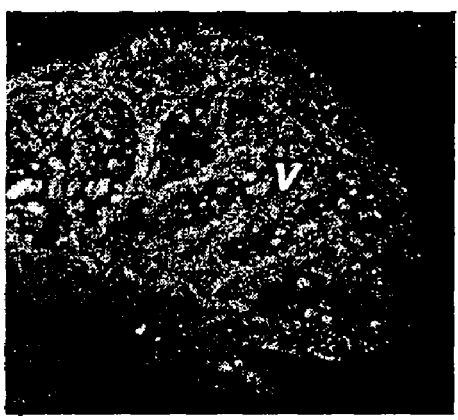

Exemplary SECM procedures and systems provide a transverse resolution comparable to those associated with FFOCM, but at higher frame rates, enabling microscopy of the heart in vivo. The Xenopus myocardium (stage 49) was imaged in vivo using the exemplary SECM procedures and systems at a frame rate of 10/s, a field of view of 220×220 µm, and transverse and axial resolutions of 1.2 and 6 µm, respectively. The maximum penetration depth was 280 µm. Exemplary of the same tadpole (stage 49) visualized by TD-OCT (as shown in FIGS. 15a and 15b) and FFOCM (as shown in FIGS. 16*a*-16*m*) procedures and systems, show the thin cusps of the atrioventricular valve (as shown in FIG. 17*a*), approximately 280 μm below the ventral surface, and parts of the ventricle and TA (as shown in FIG. 17*c*), containing individual blood cells within the intratrabecular spaces. SECM images correlated well with corresponding histology sections (as shown in FIGS. 17*b* and 17*d*). A series of frames from a different tadpole (stage 47), demonstrates the spiral valve as it closes (as shown in FIG. 17*e*) and opens (as shown in FIGS. 17*f* and 17*g*), regulating blood flow, seen at the single-cell level, from the TA to the aortic bifurcation. Blood cells are also apparent within the trabeculae (as shown in as shown in FIG. 17*h*). Intracellular features within individual myocytes that may represent nuclei and organelles can be observed.

Aneurismal Dilatation in the Xenopus Embryo

Figure 18A:
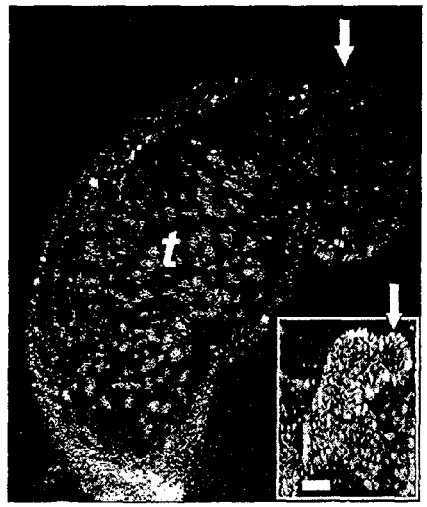
FIGS. 18a-18e are exemplary images of an aneurismal dilatation in the Xenopus heart obtained using the exemplary embodiments of the method and arrangements according to the present invention.
Figure 18B:
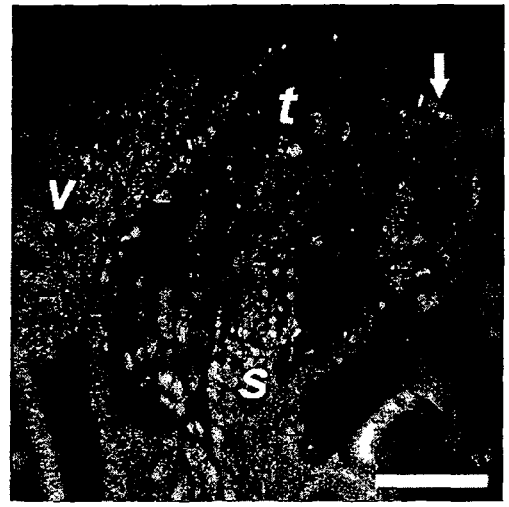
Figure 18C:
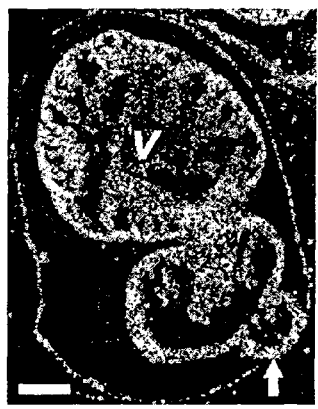
Figure 18D:
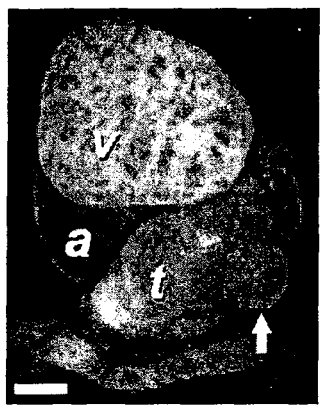
Figure 18E:
Figure 19:
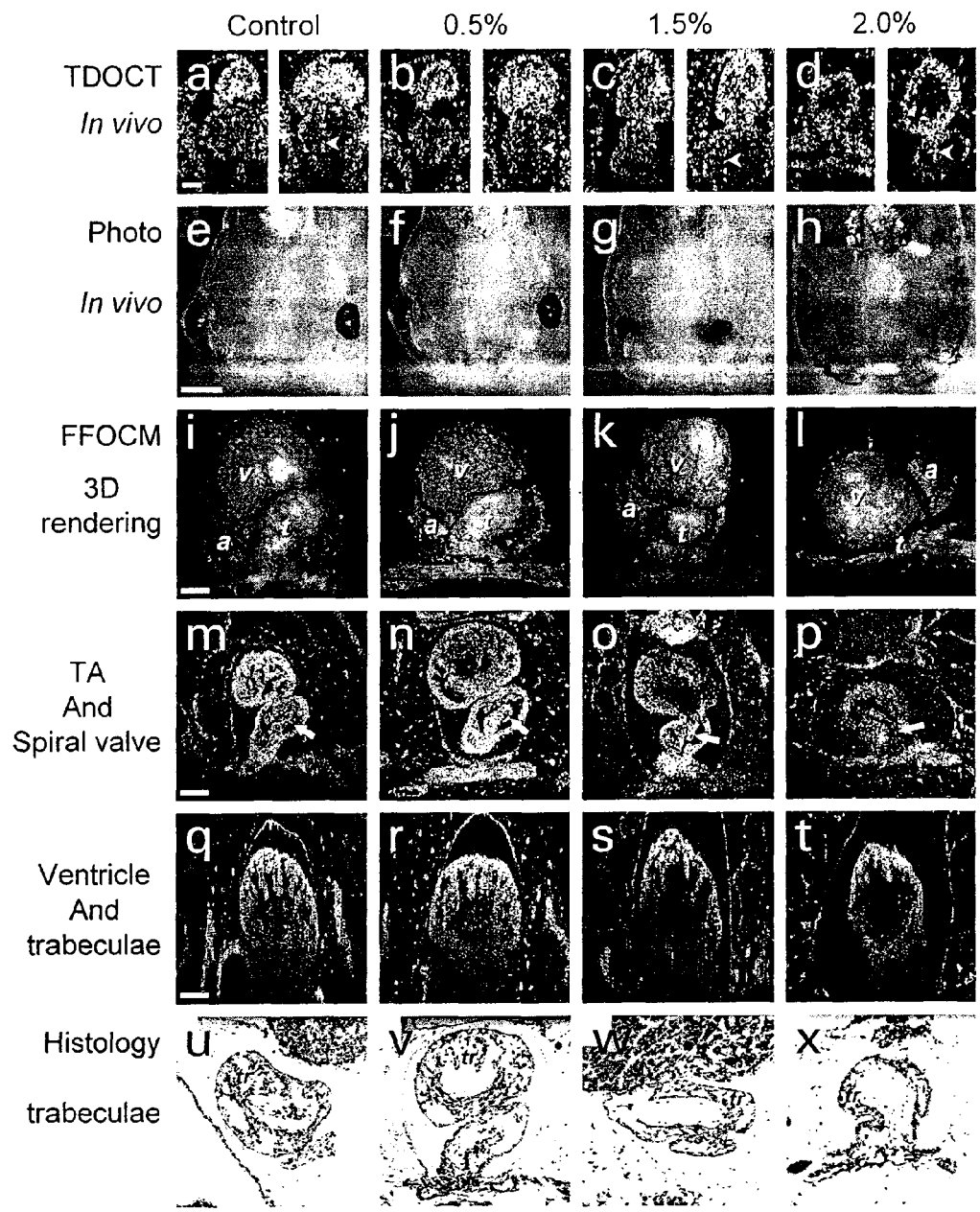
FIGS. 19a-19x are exemplary images of abnormal heart formation due to ethanol exposure using the exemplary embodiments of the method and arrangements according to the present invention.

In one of the embryos (stage 47), a protrusion emanating from the TA wall has been identified. SECM sections obtained in vivo at two different depths (as shown in FIGS. 18*a* and 18*b*), reveal its saccular shape, its location with respect to spiral valve, as well the flow of individual blood cells through the defect. This abnormality was also FIG. 18*a*, see inset). The embryo was then fixed and imaged with the exemplary FFOCM procedures and systems. An FFOCM section (as shown in FIG. 18*c*) and a three-dimensional rendering of the FFOCM volumetric data set (as shown in FIG. 18*d*) show the dilatation in the context of the entire heart. Difficult to see under conventional brightfield microscopy (as shown in FIG. 18*e*), but clearly visualized using exemplary TDOCT, FFOCM and SECM procedures and systems, this protrusion may represent a saccular aneurismal dilatation of the TA, in a heart that otherwise appeared to have a normal phenotype.

Heart Abnormalities Due to Ethanol Exposure

Cardiovascular malformation can be caused by genetic (as described in K. L. Clark et al., "Transcription factors and congenital heart defects," *Annu Rev Physiol* 68, pp. 97-121 (2006)) and teratogenic factors (as described in S. M. Mone et al., "Effects of environmental exposures on the cardiovascular system: prenatal period through adolescence," *Pediatrics* 113, pp. 1058-1069 (2004)). Ethanol is a well-known teratogen; exposure of human embryo during pregnancy to alcohol (ethanol) is associated with Fetal Alcohol Syndrome (FAS). (See K. L. Jones et al., "Recognition of the fetal alcohol syndrome in early infancy," *Lancet* 2, pp. 999-1001 (1973), and J. D. Chaudhuri, "Alcohol and the developing fetus—a review," *Med Sci Monit* 6, pp. 1031-1041 (2000)). One estimate indicates that 54% of the children with FAS have heart defects. (See E. L. Abel, *Fetal Alcohol Syndrome, Medical Economics Books, Oradell, N.J.,* 1990).

In order to study the teratogenic effect of ethanol on Xenopus heart development, embryos were exposed to different concentrations of ethanol (0.5%-2.5%) from the mid blastula transition (stage 8.5). (See R. Yelin et al., "Ethanol exposure affects gene expression in the embryonic organizer and reduces retinoic acid levels," *Dev Biol* 279, pp. 193-204 (2005)). Siblings developing under the same conditions, but not exposed to ethanol were used as controls. During the developmental process we screened the heart area of the embryos using the exemplary TDOCT procedures and systems to identify and qualitatively evaluate the extent of the teratogenic effect. We did not observe morphologic differences between the 0.5% ethanol treated group (n=16) and the control group (n=42). Moderate teratogenic effects, defined as complete maturation with a substantial change in morphology compared to the controls, was found in a minority (25%) of embryos that were exposed to 1% ethanol (n=28), and in a majority (74%) of embryos that were exposed to 1.5% ethanol (n=27). Severe effect, defined as grossly abnormal rotation of the heart tube and/or incomplete maturation, was found in all the embryos in the 2.0% and 2.5% groups (n=17, n=7, respectively). Cardiac motion was evident in all embryos, even those with the most severe malformations.

Using the exemplary TDOCT procedures and systems, a tadpole (stage 48) has been selected from each of the control, 0.5%, 1.5%, and 2.0% ethanol treated groups to demonstrate typical phenotypes (as shown in FIGS. 19*a*-19*d*). It was determined that the four tadpoles' hearts were in advanced developmental stages by identifying the existence of a partial atrial septum (as shown in FIGS. 19*a*-19*d*, see right images, septa marked by arrows) and an atrioventricular valve. The TDOCT images provided the first indication of damaged looping in the 1.5% and 2.0% groups. Further observed were lower TDOCT signal from within the ventricle in the 1.5% and 2.0% groups, which may be attributed to diminished blood flow in these embryos. Photographs of the tadpoles, taken in vivo from the ventral aspect, are shown in FIGS. 19*e*-19*h*.

Three-dimensional rendering of data acquired with the exemplary FFOCM systems and procedures in vitro allowed evaluation of myocardial structure at high-resolution, revealing the similarity between the control and the 0.5% tadpoles and clearly showing defective heart tube looping in the tadpoles from the 1.5% and 2.0% groups (as shown in FIGS. 19*i*-19*l*). Sections through the FFOCM volumetric data sets demonstrated smaller, distorted TA's and spiral valves (marked by arrows) in the 1.5% (as shown in FIG. 19*o*) and 2.0% embryos (as shown in FIG. 19*p*) compared with the control (as shown in FIG. 19*m*) and the 0.5% (as shown in FIG. 19*n*) embryos. Pericardial edema was present in the 1.5% and 2.0% groups (as shown in FIGS. 19*o*, 19*p*, 19*s* and 19*t*), compared with control and 0.5% groups. Ethanol also affected the ventricle; the developed trabeculae in the control (as shown in FIG. 19*q*) and 0.5% (as shown in FIG. 19*r*) hearts contrast the less developed trabeculae in the 1.5% group (as shown in FIG. 19*s*) and the large ventricular cavity with sparse, stunted trabeculae in embryos exposed to 2.0% ethanol (as shown in FIG. 19*t*). Corresponding histological sections confirmed some of our findings, including the less developed trabeculae (as shown in FIGS. 19*u*-19*x*) in embryos with the greater ethanol exposure.

Discussion of Exemplary Results

A common paradigm in developmental biology research is to manipulate the genotype and monitor the phenotype. Morphology is an important aspect of the phenotype. In the heart, even slight morphological and dynamical abnormalities may be critical for proper myocardial function. An ability to identify subtle morphological and dynamical variations in two and three dimensions can significantly improve the sensitivity of this paradigm.

In the Xenopus tadpole, heart structures such as the myocardium wall, septum and valves may only be a few cells thick. Evaluating the morphological phenotype not only requires resolving such fine structures, but also the capability to visualize these microscopic features within the beating heart, where typical displacement velocities are on the order of 1 mm/sec. If the imaging speed is sufficiently high, three-dimensional images of the embryo heart can be obtained at different times within the cardiac cycle. This exemplary four-dimensional imaging could allow reliable measurements of dynamic physiological parameters, such as stroke volume and ejection fraction, as well as valve opposition, stiffness and modularity, which have close analogs in human pathophysiology. High resolution and high speed are not the only requirements for effective imaging of the heart. In the Xenopus embryo, the heart extends from between 200 μm and 800

µm beneath the ventral surface. An effective imaging method should therefore also be capable of imaging at these depths without substantial loss of signal and resolution.

The morphology of the developing Xenopus laevis heart has been studied in vitro and described in detail, using three-dimensional rendering of histology sections. (See T. J. Mohun et al., "The morphology of heart development in Xenopus laevis," Dev Biol 218, 74-88 (2000)). For histologic studies, however, sample preparation and sectioning make preserving structural fidelity difficult. As a result, imaging of intact embryos in their natural environment is preferred. Structural imaging of the heart in vivo has been demonstrated using a variety of non-invasive imaging modalities such as micro-MRI (see D. L. Kraitchman et al., "In vivo magnetic resonance imaging of mesenchymal stem cells in myocardial infarction," Circulation 107, pp. 2290-2293 (2003), and F. Wiesmann et al., "Developmental changes of cardiac function and mass assessed with MRI in neonatal, juvenile, and adult mice," Am J Physiol Heart Circ Physiol 278, pp. H652-657 (2000)), micro-CT (see M. Malyar et al., "Relationship between arterial diameter and perfused tissue volume in myocardial microcirculation: a micro-CT-based analysis," Am J Physiol Heart Circ Physiol 286, pp. H2386-2392 (2004), and C. T. Badea et al., "4-D micro-CT of the mouse heart," Mol Imaging 4, pp. 110-116 (2005)), ultrasound (see S. Srinivasan et al., "Noninvasive, in utero imaging of mouse embryonic heart development with 40-MHz echocardiography," Circulation 98, pp. 912-918 (1998)), and PET (see L. W. Dobrucki et al., "Molecular cardiovascular imaging," Curr Cardiol Rep 7, pp. 130-135 (2005), and L. Stegger et al., "Monitoring left ventricular dilation in mice with PET," J Nucl Med 46, pp. 1516-1521 (2005)).

Optical techniques enable imaging of the embryonic heart at higher resolution. Confocal microscopy has been used to image early Xenopus heart development, in vitro (as described in S. J. Kolker et al., "Confocal imaging of early heart development in Xenopus laevis," Dev Biol 218, pp. 64-73 (2000)), and to study the role of intracardiac fluid forces in zebrafish embryonic cardiogenesis, in vivo (as described in J. R. Hove et al., "Intracardiac fluid forces are an essential epigenetic factor for embryonic cardiogenesis," Nature 421, pp. 172-177 (2003)). Doppler TDOCT procedures and systems were used to study blood flow in the Xenopus tadpole, allowing quantitative velocity measurements under the tissue surface. (See J. R. Hove et al., "Intracardiac fluid forces are an essential epigenetic factor for embryonic cardiogenesis," Nature 421, pp. 172-177 (2003), and V. X. D. Yang, M. L. Gordon, E. Seng-Yue et al., "High speed, wide velocity dynamic range Doppler optical coherence tomography (Part II): Imaging in vivo cardiac dynamics of Xenopus laevis," Optics Express 11, pp. 1650-1658 (2003)). Due to its limited imaging speed, three-dimensional heart imaging using TDOCT has primarily only been previously demonstrated in vitro. (See S. A. Boppart et al., "Noninvasive assessment of the developing Xenopus cardiovascular system using optical coherence tomography," Proc Natl Acad Sci USA 94, pp. 4256-4261 (1997), T. M. Yelbuz et al., "Optical coherence tomography: a new high-resolution imaging technology to study cardiac development in chick embryos," Circulation 106, pp. 2771-2774 (2002), and W. Luo et al., "Three-dimensional optical coherence tomography of the embryonic murine cardiovascular system" Journal of biomedical optics 11, 021014 (2006).

Gating or post-acquisition synchronization techniques have been employed to circumvent the limited speed of conventional imaging methods, enabling the reconstruction of three-dimensional images of embryo hearts at different stages in the cardiac cycle. (See M. W. Jenkins et al., "4D embryonic cardiography using gated optical coherence tomography," Optics Express 14, pp. 736-748 (2006). M. Liebling et al., "Four-dimensional cardiac imaging in living embryos via postacquisition synchronization of nongated slice sequences," J Biomed Opt 10, 054001 (2005). For some of the experiments, we utilized TDOCT as it was more readily available in our laboratory, however the exemplary OFDI procedures and systems were capable of providing all of the functionality of the exemplary TDOCT procedures and systems at much higher speeds. The exemplary OFDI procedures and systems provided real-time, true four-dimensional imaging of a beating heart without requiring cardiac gating and was found to be useful for assessing myocardial wall displacement during the cardiac cycle (as shown in FIGS. 15c-15f).

By modifying the OFDI light source, we were also able to conduct real-time cross-sectional imaging with higher axial resolution (4 µm), enabling visualization of valve dynamics (as shown in FIGS. 15i-15k) and single-cell blood flow. For subcellular-level resolution imaging of the embryonic heart, we investigated the use of the exemplary FFOCM and SECM procedures and systems. The FFOCM modality was found to be capable of providing high quality three-dimensional imaging with isotropic cellular (1-2 µm) resolution. The SECM modality demonstrated comparable resolution to the FFOCM modality, but was capable of imaging at higher speeds, enabling visualization of myocyte, blood, and valve motion in vivo at the subcellular level. Table 1 summarizes the different capabilities of each procedure, highlighting their complementary nature.

TABLE 1

Comparison of endogenous-contrast modalities for optical imaging of the embryonic heart. Cells shaded in gray denote the imaging technologies with the best transverse resolution, axial resolution, and frame rate characteristics.

|  | OCT* | FFOCM | SECM |
| --- | --- | --- | --- |
| Transverse resolution | 2-16 µm | 2 µm | 0.9 µm |
| Axial resolution | 4-10 µm | 1.1 µm | 2.5 µm |
| Speed [frames per second] | 10-1000 | 0.5 | 10 |
| Three dimension in vivo (4D) | Yes | No | No |
| Applications | Architectural dynamics | Whole organ microscopic morphology | Subcellular dynamics |

*Includes TDOCT and OFDI modalities.

The large penetration depth of the exemplary TDOCT and FFOCM procedures and systems allowed imaging of the heart through pericardial edema that developed as part of the ethanol teratogenic phenotype. Our preliminary results suggest that ethanol interferes with the process of heart looping (FIGS. 19i-l), in agreement with a study in quail. (See W. O. Twal et al., "Retinoic acid reverses ethanol-induced cardiovascular abnormalities in quail embryos," Alcohol Clin Exp Res 21, pp. 1137-1143 (1997)). The reduction in TA size that is reported in this work was predicted by Cavierres and Smith, (see M. F. Cavieres et al., "Genetic and developmental modulation of cardiac deficits in prenatal alcohol exposure," Alcohol Clin Exp Res 24, pp. 102-109 (2000)), but not observed. It is believed that the less developed ventricular trabeculae described here (as shown in FIGS. 19q-t) have not been previously developed. Since in Xenopus and zebrafish (Danio rerio), the ventricular trabeculae serve as a functional equivalent of the His-Purkinje system (see D. Sedmera et al., "Functional and morphological evidence for a ventricular conduction system in zebrafish and Xenopus hearts," *Am J Physiol Heart Circ Physiol* 284, pp. H1152-1160 (2003)), .a determination of less developed trabeculae could be associated with the slower heart rate that has been reported in ethanol treated quail (see W. O. Twal et al., "Retinoic acid reverses ethanol-induced cardiovascular abnormalities in quail embryos," *Alcohol Clin Exp Res* 21, pp. 1137-1143 (1997)), and zebrafish embryos (see J. Bilotta et al., "Ethanol exposure alters zebrafish development: a novel model of fetal alcohol syndrome," *Neurotoxicol Teratol* 26, pp. 737-743 (2004)). Interruption of active blood circulation due to ethanol treatment (W. O. Twal et al., "Retinoic acid reverses ethanol-induced cardiovascular abnormalities in quail embryos," *Alcohol Clin Exp Res* 21, pp. 1137-1143 (1997), and X. Wang et al., "Japanese medaka (Oryzias latipes): developmental model for the study of alcohol teratology," *Birth Defects Res B Dev Reprod Toxicol* 77, pp. 29-39 (2006)) may explain the loss of signal from within the heart cavities, which is also consistent with the determinations.

Despite their relatively high penetration depth, none of the conventional optical imaging procedures could image the heart at the onset of cardiac organogensis (heart tube formation, stage 29), due to high scattering at these earlier stages. The initiation of cardiac movements (stage 35), however, was observed and detailed structural images at the onset of chamber formation (around stage 40) were obtained as the embryo became optically transparent. Especially for the FFOCM and SECM modalities, it was difficult to match histology to the microscopy data sets. The embryos were quite fragile when processed and embedded, making preservation of morphology challenging. Furthermore, images should be registered to histology with a precision on the order of 10 μm, which is difficult to achieve with conventional sectioning techniques.

For the imaging procedures according to exemplary embodiments of the present invention, contrast was generated by endogenous scattering. Still, molecular imaging may be important for relating gene and protein expression to phenotype. Thus, the exemplary systems and methods described herein can be used for imaging fluorescent labels and molecular species. It has been described that fluorescence imaging can be conducted via spectral encoding by modification of the source and detection electronics. (See J. T. Motz et al., "Spectral- and frequency-encoded fluorescence imaging," *Opt Lett* 30, pp. 2760-2762 (2005)). The same principles used in fluorescence SECM procedures and systems can likewise be utilized for endoscopic two-photon and second harmonic imaging. With the coherent detection used in the exemplary TDOCT, OFDI, and FFOCM procedures and systems, it may be difficult to directly detect fluorescence. However, several molecular contrast methods have already been described for the OCT modality. (See C. Yang, "Molecular contrast optical coherence tomography: a review," *Photochem Photobiol* 81, pp. 215-237 (2005) and S. A. Boppart, et al., "Optical probes and techniques for molecular contrast enhancement in coherence imaging," *J Biomed Opt* 10, 41208 (2005)).

The natural contrast optical imaging modalities presented in this work allow evaluation of the embryonic heart from different vantage points. Combining OFDI, SECM, and FFOCM modalities can leverage their strengths (see Table 1), and provide a ability for obtaining a more comprehensive morphological and functional myocardial phenotype. This multi-modality paradigm can be extended to other systems and animal models as well. Since these non-invasive imaging techniques do not alter the specimen, they can be used sequentially or in parallel. Furthermore, while we have used separate imaging systems in this work, there is no fundamental barrier preventing their combination into one imaging system that uses a single wavelength swept source. (See S. H. Yun et al., "High-speed optical frequency-domain imaging," *Optics Express* 11, pp. 2953-2963 (2003); C. Boudoux et al., "Rapid wavelength-swept spectrally encoded confocal microscopy," *Optics Express* 13, pp. 8214-8221 (2005); and W. Y. Oh et al., "Wide tuning range wavelength-swept laser with two semiconductor optical amplifiers," *IEEE Photonics Technology Letters* 17, pp. 678-680 (2005)).

The foregoing merely illustrates the principles of the invention. Various modifications and alterations to the described embodiments will be apparent to those skilled in the art in view of the teachings herein. Indeed, the arrangements, systems and methods according to the exemplary embodiments of the present invention can be used with any OCT system, OFDI system, SD-OCT system or other imaging systems, and for example with those described in International Patent Application PCT/US2004/029148, filed Sep. 8, 2004, U.S. patent application Ser. No. 11/266,779, filed Nov. 2, 2005, and U.S. patent application Ser. No. 10/501,276, filed Jul. 9, 2004, the disclosures of which are incorporated by reference herein in their entireties. It will thus be appreciated that those skilled in the art will be able to devise numerous systems, arrangements and methods which, although not explicitly shown or described herein, embody the principles of the invention and are thus within the spirit and scope of the present invention. In addition, to the extent that the prior art knowledge has not been explicitly incorporated by reference herein above, it is explicitly being incorporated herein in its entirety. All publications referenced herein above are incorporated herein by reference in their entireties.

What is claimed is:

1. An apparatus comprising:
   a light source emitting an electro-magnetic radiation; and
   at least one arrangement configured to provide (i) first data associated with a first signal received from at least one region of at least one sample based on a first modality, (ii) second data associated with a second signal received from the at least one sample based on a second modality which is different from the first modality, and (iii) at least one third data associated with a third signal received from the at least one sample, wherein each of the at least one third data is based on a third modality which is different from the first modality and the second modality,
   wherein the first, second and third signals are generated by the electro-magnetic radiation emitted by the light source.

2. The apparatus according to claim 1, further comprising at least one second arrangement which is configured to obtain optical coherence tomography information based on the first, second and third data.

3. The apparatus according to claim 2, further comprising:
   at least one third arrangement configured to control at least one of the light source or the at least one second arrangement based on at least one of the previously-obtained first data or the second data.

4. The apparatus according to claim 1, wherein the at least one arrangement is configured to obtain optical coherence microscopy information.

5. The apparatus according to claim 1, wherein the at least one arrangement is configured to obtain full field optical coherence microscopy information.

6. The apparatus according to claim 1, wherein the first and second data are provided substantially simultaneously by the at least one arrangement.

7. The apparatus according to claim 1, wherein the light source and arrangement are provided in at least one of a probe or a single enclosure.

8. The apparatus according to claim 1, wherein the light source and arrangement include common components which are provided in a wavelength swept-source arrangement.

9. The apparatus according to claim 1, wherein the at least one arrangement is further configured to obtain optical coherence tomography information associated with a signal provided by a source arrangement whose wavelength varies over time.

10. The apparatus according to claim 1, wherein the at least one arrangement is provided in at least one of a probe or a single enclosure, and further comprising:
at least one positioning arrangement configured to position the at least one of the probe or the single enclosure at a particular location relative to the sample based on at least one of the first data or the second data.

11. The apparatus according to claim 1, wherein the light source is a sole source of a generated radiation in the apparatus.

12. The apparatus according to claim 1, wherein one of the first, second and third modalities is a optical coherence tomography modality, and another one of the first, second and third modalities is a spectral encoding modality.

13. An apparatus comprising:
a light source emitting an electro-magnetic radiation; and
at least one arrangement configured to provide (i) first data associated with a first signal received from at least one region of at least one sample based on a spectral-encoding first modality, and (ii) second data associated with a second signal received from the at least one sample based on a non-spectral-encoding second modality,
wherein the first and second signals are generated by the electro-magnetic radiation emitted by the light source.

14. The apparatus according to claim 13, wherein the first and second data are provided substantially simultaneously by the at least one arrangement.

15. The apparatus according to claim 13, wherein the at least one arrangement is provided in at least one of a probe or a single enclosure.

16. The apparatus according to claim 13, wherein the light source and the at least one arrangement include common components which are provided in a wavelength swept-source arrangement.

17. The apparatus according to claim 13, wherein the at least one arrangement is further configured to obtain optical coherence tomography information associated with a signal provided by a source arrangement whose wavelength varies over time.

18. The apparatus according to claim 13, further comprising:
at least one second arrangement configured to control at least one of the light source or the at least one arrangement based on at least one of the previously-obtained first data or the second data.

19. The apparatus according to claim 13, wherein the light source is provided in at least one of a probe or a single enclosure, and further comprising:
at least one positioning second arrangement configured to position the at least one of the probe or the single enclosure at a particular location relative to the sample based on at least one of the first data or the second data.

20. The apparatus according to claim 13, wherein the light source is a sole source of a generated radiation in the apparatus.

21. A method comprising:
emitting an electro-magnetic radiation using a light source arrangement; and
providing (i) first data associated with a first signal received from at least one region of at least one sample based on a first modality, (ii) second data associated with a second signal received from the at least one sample based on a second modality which is different from the first modality, and (iii) at least one third data associated with a third signal received from the at least one sample, wherein each of the at least one third data is based on a third modality which is different from the first modality and the second modality,
wherein the first and second signals are generated by the electro-magnetic radiation emitted by the light source.

22. A method comprising:
emitting an electro-magnetic radiation using a light source arrangement; and
providing (i) first data associated with a first signal received from at least one region of at least one sample based on a spectral-encoding first modality, and (ii) second data associated with a second signal received from the at least one sample based on a non-spectral-encoding second modality,
wherein the first and second signals are generated by the electro-magnetic radiation emitted by the light source.

* * * * *